(12) United States Patent
Campbell et al.

(10) Patent No.: US 11,311,419 B2
(45) Date of Patent: Apr. 26, 2022

(54) EUSTACHIAN TUBE DILATION BALLOON WITH VENTILATION PATH

(71) Applicant: Acclarent, Inc., Irvine, CA (US)

(72) Inventors: Peter F. Campbell, San Jose, CA (US); Daniel T. Harfe, Los Altos, CA (US); Hung V. Ha, San Jose, CA (US); Ketan P. Muni, San Jose, CA (US); Andy Nguyen, San Jose, CA (US); Sivette Lam, Milpitas, CA (US); John Y. Chang, Los Altos, CA (US); Eric Goldfarb, Belmont, CA (US)

(73) Assignee: Acclarent, Inc., Irvine, CA (US)

( * ) Notice: Subject to any disclaimer, the term of this patent is extended or adjusted under 35 U.S.C. 154(b) by 143 days.

(21) Appl. No.: 16/207,373

(22) Filed: Dec. 3, 2018

(65) Prior Publication Data

US 2019/0175413 A1    Jun. 13, 2019

Related U.S. Application Data

(63) Continuation of application No. 14/674,639, filed on Mar. 31, 2015, now Pat. No. 10,206,821, which is a
(Continued)

(51) Int. Cl.
*A61F 11/00* (2022.01)
*A61F 11/20* (2022.01)
(Continued)

(52) U.S. Cl.
CPC .............. *A61F 11/202* (2022.01); *A61B 1/07* (2013.01); *A61B 1/227* (2013.01); *A61B 1/233* (2013.01);
(Continued)

(58) Field of Classification Search
CPC .................. A61F 11/002; A61F 11/004; A61F 2250/0067; A61B 1/227; A61B 1/07;
(Continued)

(56) References Cited

U.S. PATENT DOCUMENTS

| 446,173 A | 2/1891 | Hancock |
| 504,424 A | 9/1893 | De Pezzer |

(Continued)

FOREIGN PATENT DOCUMENTS

| CH | 668188 | 12/1988 |
| CN | 2151720 | 1/1994 |

(Continued)

OTHER PUBLICATIONS

Canadian Office Action dated Dec. 2, 2016 for Application No. 2,785,652, 3 pages.

(Continued)

*Primary Examiner* — Richard G Louis
(74) *Attorney, Agent, or Firm* — Frost Brown Todd LLC

(57) ABSTRACT

An apparatus comprises a shaft, an expandable dilator, and at least one ventilation pathway. The shaft defines a longitudinal axis and comprises a distal and proximal ends with at least one shaft lumen. The expandable dilator comprises body with its own proximal and distal ends. The body is configured to transition between a contracted state and an expanded state. The body is configured to dilate a Eustachian tube of a patient in the expanded state. The at least one ventilation pathway is configured to provide ventilation from the distal end of the body to the proximal end of the body when the body is in the expanded state. In some examples, the ventilation pathway comprises a set of transversely oriented vent openings formed through the shaft. In some other examples, the ventilation pathway comprises a
(Continued)

space defined between one or more radially outwardly protruding features of the expandable dilator.

18 Claims, 40 Drawing Sheets

Related U.S. Application Data continuation-in-part of application No. 12/777,856, filed on May 11, 2010, now abandoned, which is a continuation-in-part of application No. 12/649,078, filed on Dec. 29, 2009, now abandoned, which is a continuation-in-part of application No. 12/340,226, filed on Dec. 19, 2008, now abandoned.

(60) Provisional application No. 61/015,647, filed on Dec. 20, 2007.

(51) Int. Cl.

| | | |
|---|---|---|
| *A61M 25/09* | (2006.01) | |
| *A61B 1/07* | (2006.01) | |
| *A61B 1/233* | (2006.01) | |
| *A61B 5/00* | (2006.01) | |
| *A61B 17/12* | (2006.01) | |
| *A61B 17/00* | (2006.01) | |
| *A61B 1/227* | (2006.01) | |
| *A61B 8/12* | (2006.01) | |
| *A61N 7/02* | (2006.01) | |
| *A61B 5/03* | (2006.01) | |
| *A61M 25/00* | (2006.01) | |
| *A61M 25/10* | (2013.01) | |
| *A61M 29/02* | (2006.01) | |
| *A61M 31/00* | (2006.01) | |
| A61B 18/20 | (2006.01) | |
| A61M 25/01 | (2006.01) | |
| A61N 1/30 | (2006.01) | |
| A61B 18/00 | (2006.01) | |
| A61B 18/14 | (2006.01) | |

(52) U.S. Cl.
CPC .............. *A61B 5/036* (2013.01); *A61B 5/411* (2013.01); *A61B 5/415* (2013.01); *A61B 5/6852* (2013.01); *A61B 8/12* (2013.01); *A61B 17/00234* (2013.01); *A61B 17/12104* (2013.01); *A61B 17/12131* (2013.01); *A61M 25/0041* (2013.01); *A61M 25/0068* (2013.01); *A61M 25/09* (2013.01); *A61M 25/10* (2013.01); *A61M 29/02* (2013.01); *A61M 31/00* (2013.01); *A61M 31/002* (2013.01); *A61N 7/02* (2013.01); A61B 18/20 (2013.01); A61B 2017/00296 (2013.01); A61B 2017/00787 (2013.01); A61B 2018/00327 (2013.01); A61B 2018/144 (2013.01); A61F 11/20 (2022.01); A61F 2250/0067 (2013.01); A61M 25/007 (2013.01); A61M 25/0032 (2013.01); A61M 25/0054 (2013.01); A61M 25/01 (2013.01); A61M 25/0102 (2013.01); A61M 25/0105 (2013.01); A61M 25/0147 (2013.01); A61M 2025/0008 (2013.01); A61M 2025/0166 (2013.01); A61M 2025/09008 (2013.01); A61M 2025/09183 (2013.01); A61M 2025/105 (2013.01); A61M 2025/1075 (2013.01); A61M 2210/0681 (2013.01); A61N 1/30 (2013.01)

(58) Field of Classification Search
CPC ......... A61B 1/233; A61B 5/411; A61B 5/415; A61B 5/6852; A61B 17/00234; A61B 17/12104; A61B 17/12131; A61B 18/20; A61B 2017/00296; A61B 2017/00787; A61B 2018/00327; A61B 2018/144; A61M 29/02; A61M 25/0041; A61M 25/0068; A61M 25/09; A61M 25/10; A61M 31/00; A61M 31/002; A61M 25/0032; A61M 25/0054; A61M 25/007; A61M 25/01; A61M 25/0102; A61M 25/0105; A61M 25/0147; A61M 2025/0008; A61M 2025/0166; A61M 2025/09008; A61M 2025/105; A61M 2025/1075; A61M 2210/0681; A61N 7/02; A61N 1/30

See application file for complete search history.

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,792,391 A | 2/1974 | Ewing |
| 3,802,096 A | 4/1974 | Matern |
| 3,804,081 A | 4/1974 | Kinoshita |
| 3,800,788 A | 7/1974 | White |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |

(56) References Cited

U.S. PATENT DOCUMENTS

| | | |
|---|---|---|
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Reidhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,777,951 A | 10/1988 | Cribier et al. |
| 4,784,117 A | 11/1988 | Miyazaki |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,878,495 A | 11/1989 | Grayzel |
| 4,883,465 A | 11/1989 | Brennan |
| 4,884,573 A | 12/1989 | Wijay et al. |
| 4,888,017 A | 12/1989 | De Vore et al. |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gambale et al. |
| 5,067,489 A | 11/1991 | Lind |
| 5,069,226 A | 12/1991 | Tamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,099,845 A | 3/1992 | Besz et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Olivier |
| 5,156,595 A | 10/1992 | Adams |
| 5,163,905 A * | 11/1992 | Don Michael ..... A61M 25/1011 604/101.03 |
| 5,163,989 A | 11/1992 | Campbell et al. |
| 5,167,220 A | 12/1992 | Brown |
| 5,168,864 A | 12/1992 | Shockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deneiga |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |

(56) References Cited

U.S. PATENT DOCUMENTS

| | | |
|---|---|---|
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,408 A | 5/1994 | Salmon et al. |
| 5,314,417 A | 5/1994 | Stephens et al. |
| 5,315,618 A | 5/1994 | Yoshida |
| 5,324,306 A | 6/1994 | Makower et al. |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wang |
| 5,538,008 A | 7/1996 | Crowe |
| 5,545,200 A | 8/1996 | West et al. |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,690,642 A * | 11/1997 | Osborne ............... A61F 2/958 604/103.04 |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,730,724 A | 3/1998 | Plishka et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterweck et al. |
| 5,902,247 A | 5/1999 | Coe et al. |
| 5,902,333 A | 5/1999 | Roberts et al. |

(56) References Cited

U.S. PATENT DOCUMENTS

| | | | |
|---|---|---|---|
| 5,904,701 A | 5/1999 | Daneshvar | |
| 5,908,407 A | 6/1999 | Frazee et al. | |
| 5,916,193 A | 6/1999 | Stevens et al. | |
| 5,928,192 A | 7/1999 | Maahs | |
| 5,931,811 A | 8/1999 | Haissaguerre et al. | |
| 5,931,818 A | 8/1999 | Werp et al. | |
| 5,932,035 A | 8/1999 | Koger et al. | |
| 5,935,061 A | 8/1999 | Acker et al. | |
| 5,941,816 A | 8/1999 | Barthel et al. | |
| D413,629 S | 9/1999 | Wolff et al. | |
| 5,947,988 A | 9/1999 | Smith | |
| 5,949,929 A | 9/1999 | Hamm | |
| 5,954,693 A | 9/1999 | Barry | |
| 5,954,694 A | 9/1999 | Sunseri | |
| 5,957,842 A | 9/1999 | Littmann et al. | |
| 5,968,085 A | 10/1999 | Morris et al. | |
| 5,971,975 A | 10/1999 | Mills et al. | |
| 5,979,290 A | 11/1999 | Simeone | |
| 5,980,503 A | 11/1999 | Chin | |
| 5,980,551 A | 11/1999 | Summers et al. | |
| 5,984,945 A | 11/1999 | Sirhan | |
| 5,985,307 A | 11/1999 | Hanson et al. | |
| 5,997,562 A | 12/1999 | Zadno-Azizi et al. | |
| 6,006,126 A | 12/1999 | Cosman | |
| 6,006,130 A | 12/1999 | Higo et al. | |
| 6,007,516 A | 12/1999 | Burbank et al. | |
| 6,007,991 A | 12/1999 | Sivaraman et al. | |
| 6,010,511 A | 1/2000 | Murphy | |
| 6,013,019 A | 1/2000 | Fischell et al. | |
| 6,015,414 A | 1/2000 | Werp et al. | |
| 6,016,429 A | 1/2000 | Khafizov et al. | |
| 6,016,439 A | 1/2000 | Acker | |
| 6,019,736 A | 2/2000 | Avellanet et al. | |
| 6,019,777 A | 2/2000 | Mackenzie | |
| 6,021,340 A | 2/2000 | Randolph et al. | |
| 6,022,313 A | 2/2000 | Ginn et al. | |
| 6,027,461 A | 2/2000 | Walker et al. | |
| 6,027,478 A | 2/2000 | Katz | |
| 6,039,699 A | 3/2000 | Viera | |
| 6,042,561 A | 3/2000 | Ash et al. | |
| 6,048,299 A | 4/2000 | von Hoffmann | |
| 6,048,358 A | 4/2000 | Barak | |
| 6,053,172 A | 4/2000 | Hovda et al. | |
| 6,056,702 A | 5/2000 | Lorenzo | |
| 6,059,752 A | 5/2000 | Segal | |
| 6,071,233 A | 6/2000 | Ishikawa et al. | |
| 6,079,755 A | 6/2000 | Chang | |
| 6,080,190 A | 6/2000 | Schwartz | |
| 6,083,148 A | 7/2000 | Williams | |
| 6,083,188 A | 7/2000 | Becker et al. | |
| 6,086,585 A | 7/2000 | Hovda et al. | |
| 6,092,846 A | 7/2000 | Fuss et al. | |
| 6,093,150 A | 7/2000 | Chandler et al. | |
| 6,093,195 A | 7/2000 | Ouchi | |
| 6,109,268 A | 8/2000 | Thapliyal et al. | |
| 6,113,567 A | 9/2000 | Becker | |
| 6,117,105 A | 9/2000 | Bresnaham et al. | |
| 6,122,541 A | 9/2000 | Cosman et al. | |
| 6,123,697 A | 9/2000 | Shippert | |
| 6,136,006 A | 10/2000 | Johnson et al. | |
| 6,139,510 A | 10/2000 | Palermo | |
| 6,142,957 A | 11/2000 | Diamond et al. | |
| 6,148,823 A | 11/2000 | Hastings | |
| 6,149,213 A | 11/2000 | Sokurenko et al. | |
| 6,159,170 A | 12/2000 | Borodulin et al. | |
| 6,171,298 B1 | 1/2001 | Matsuura et al. | |
| 6,171,303 B1 | 1/2001 | Ben-Haim | |
| 6,174,280 B1 | 1/2001 | Oneda et al. | |
| 6,176,829 B1 | 1/2001 | Vilkomerson | |
| 6,179,788 B1 | 1/2001 | Sullivan | |
| 6,179,811 B1 | 1/2001 | Fugoso et al. | |
| 6,183,461 B1 | 2/2001 | Matsuura et al. | |
| 6,183,464 B1 | 2/2001 | Sharp et al. | |
| 6,190,353 B1 | 2/2001 | Makower et al. | |
| 6,190,381 B1 | 2/2001 | Olsen et al. | |
| 6,193,650 B1 | 2/2001 | Ryan, Jr. | |
| 6,195,225 B1 | 2/2001 | Komatsu et al. | |
| 6,197,013 B1 | 3/2001 | Reed et al. | |
| 6,200,257 B1 | 3/2001 | Winkler | |
| 6,206,870 B1 | 3/2001 | Kanner | |
| 6,213,975 B1 | 4/2001 | Laksin | |
| 6,221,042 B1 | 4/2001 | Adams | |
| 6,231,543 B1 | 5/2001 | Hegde et al. | |
| 6,234,958 B1 | 5/2001 | Snoke et al. | |
| 6,238,364 B1 | 5/2001 | Becker | |
| 6,238,391 B1 | 5/2001 | Olsen et al. | |
| 6,241,519 B1 | 6/2001 | Sedleemayer | |
| 6,245,040 B1* | 6/2001 | Inderbitzen | A61M 25/104 |
| | | | 604/103.07 |
| 6,249,180 B1 | 6/2001 | Maalej et al. | |
| 6,254,550 B1 | 7/2001 | McNamara et al. | |
| 6,268,574 B1 | 7/2001 | Edens | |
| 6,293,957 B1 | 9/2001 | Peters et al. | |
| 6,302,875 B1 | 10/2001 | Makower et al. | |
| 6,306,105 B1 | 10/2001 | Rooney et al. | |
| 6,306,124 B1 | 10/2001 | Jones et al. | |
| D450,382 S | 11/2001 | Nestenborg | |
| 6,322,495 B1 | 11/2001 | Snow et al. | |
| 6,328,564 B1 | 12/2001 | Thurow | |
| 6,332,089 B1 | 12/2001 | Acker et al. | |
| 6,332,891 B1 | 12/2001 | Himes | |
| 6,340,360 B1 | 1/2002 | Lyles et al. | |
| 6,348,041 B1 | 2/2002 | Klint | |
| 6,352,503 B1 | 3/2002 | Matsui et al. | |
| 6,375,615 B1 | 4/2002 | Flaherty et al. | |
| 6,375,629 B1 | 4/2002 | Muni et al. | |
| 6,383,146 B1 | 5/2002 | Klint | |
| 6,386,197 B1 | 5/2002 | Miller | |
| 6,389,313 B1 | 5/2002 | Marchitto et al. | |
| 6,390,993 B1 | 5/2002 | Cornish et al. | |
| 6,394,093 B1 | 5/2002 | Lethi | |
| 6,398,758 B1 | 6/2002 | Jacobsen et al. | |
| 6,409,863 B1 | 6/2002 | Williams et al. | |
| 6,419,653 B2 | 7/2002 | Edwards et al. | |
| 6,423,012 B1 | 7/2002 | Kato et al. | |
| 6,425,853 B1 | 7/2002 | Edwards | |
| 6,425,877 B1 | 7/2002 | Edwards | |
| 6,432,986 B2 | 8/2002 | Levin | |
| 6,440,061 B1 | 8/2002 | Wenner et al. | |
| 6,443,947 B1 | 9/2002 | Marko et al. | |
| 6,445,939 B1 | 9/2002 | Swanson et al. | |
| 6,450,975 B1 | 9/2002 | Brennan et al. | |
| 6,450,989 B2 | 9/2002 | Dubrul et al. | |
| 6,464,650 B2 | 10/2002 | Jafari et al. | |
| 6,468,202 B1 | 10/2002 | Irion et al. | |
| 6,468,297 B1 | 10/2002 | Williams et al. | |
| 6,485,475 B1 | 11/2002 | Chelly | |
| 6,491,940 B1 | 12/2002 | Levin | |
| 6,494,894 B2 | 12/2002 | Mirarchi | |
| 6,500,130 B2 | 12/2002 | Kinsella et al. | |
| 6,500,189 B1 | 12/2002 | Lang et al. | |
| 6,503,087 B1 | 1/2003 | Eggert et al. | |
| 6,503,185 B1 | 1/2003 | Waksman et al. | |
| 6,503,263 B2 | 1/2003 | Adams | |
| 6,511,418 B2 | 1/2003 | Shahidi et al. | |
| 6,514,249 B1 | 2/2003 | Maguire et al. | |
| 6,517,478 B2 | 2/2003 | Khadem | |
| 6,524,299 B1 | 2/2003 | Tran et al. | |
| 6,526,302 B2 | 2/2003 | Hassett | |
| 6,527,753 B2 | 3/2003 | Sekine et al. | |
| 6,529,756 B1 | 3/2003 | Phan et al. | |
| 6,533,754 B1 | 3/2003 | Hisamatsu et al. | |
| 6,536,437 B1 | 3/2003 | Dragisic | |
| 6,537,294 B1 | 3/2003 | Boyle et al. | |
| 6,543,452 B1 | 4/2003 | Lavigne | |
| 6,544,230 B1 | 4/2003 | Flaherty et al. | |
| 6,549,800 B1 | 4/2003 | Atalar et al. | |
| 6,551,239 B2 | 4/2003 | Renner et al. | |
| 6,569,146 B1 | 5/2003 | Werner et al. | |
| 6,569,147 B1 | 5/2003 | Evans et al. | |
| 6,571,131 B1 | 5/2003 | Nguyen | |
| 6,572,538 B2 | 6/2003 | Takase | |
| 6,572,590 B1 | 6/2003 | Stevens et al. | |
| 6,578,581 B1 | 6/2003 | Khalsa | |

(56) References Cited

U.S. PATENT DOCUMENTS

| | | |
|---|---|---|
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,612,999 B2 | 9/2003 | Brennan et al. |
| 6,613,066 B1 | 9/2003 | Fukaya et al. |
| 6,613,077 B2 | 9/2003 | Gilligan et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,682,556 B1 * | 1/2004 | Ischinger ............... A61F 2/88 604/103.04 |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,743,208 B1 | 6/2004 | Coyle |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |

(56) References Cited

U.S. PATENT DOCUMENTS

| | | |
|---|---|---|
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,799,048 B2 | 9/2010 | Hudson et al. |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,883,717 B2 | 2/2011 | Varner et al. |
| 7,896,891 B2 | 3/2011 | Catanese, III et al. |
| 7,914,467 B2 | 3/2011 | Layman et al. |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,075,573 B2 | 12/2011 | Gabmale et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,142,468 B2 | 3/2012 | Inderbitzen et al. |
| 8,146,400 B2 | 4/2012 | Goldfarb et al. |
| 8,147,545 B2 | 4/2012 | Avior |
| 8,167,821 B2 | 5/2012 | Sharrow |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,439,687 B1 | 5/2013 | Morriss et al. |
| 8,509,916 B2 | 8/2013 | Byrd et al. |
| 8,535,707 B2 | 9/2013 | Arensdorf et al. |
| 8,585,753 B2 | 11/2013 | Scanlon et al. |
| 8,608,360 B2 | 12/2013 | Nath |
| 8,642,631 B2 | 2/2014 | Anderson et al. |
| 8,715,169 B2 | 5/2014 | Chang et al. |
| 8,718,786 B2 | 5/2014 | Shalev |
| 8,747,389 B2 | 6/2014 | Goldfarb et al. |
| 8,764,726 B2 | 7/2014 | Chang et al. |
| 8,764,729 B2 | 7/2014 | Muni et al. |
| 8,828,041 B2 | 9/2014 | Chang et al. |
| 9,155,492 B2 | 10/2015 | Jenkins et al. |
| 9,913,964 B2 | 3/2018 | Muni et al. |
| 10,206,821 B2 | 2/2019 | Campbell et al. |
| 2001/0000350 A1* | 4/2001 | Durcan ............... A61F 2/958 623/1.11 |
| 2001/0004644 A1 | 6/2001 | Levin |
| 2001/0034530 A1 | 10/2001 | Malackowski et al. |
| 2002/0006961 A1 | 1/2002 | Katz et al. |
| 2002/0055746 A1 | 5/2002 | Burke et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0083608 A1 | 5/2003 | Evans et al. |
| 2003/0114732 A1 | 6/2003 | Webler et al. |
| 2003/0114915 A1 | 6/2003 | Mareiro et al. |
| 2003/0163154 A1 | 8/2003 | Miyata et al. |
| 2003/0181923 A1* | 9/2003 | Vardi ............... A61M 25/09 606/108 |
| 2003/0208250 A1 | 11/2003 | Edwards et al. |
| 2004/0015150 A1 | 1/2004 | Zadno-Azizi |
| 2004/0018980 A1 | 1/2004 | Gurney et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0055077 A1 | 3/2005 | Marco |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0234507 A1 | 10/2005 | Geske et al. |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0025840 A1 | 2/2006 | Willard |
| 2006/0063973 A1 | 3/2006 | Makower et al. |
| 2006/0095066 A1 | 5/2006 | Chang et al. |
| 2006/0106448 A1 | 5/2006 | Shaked |
| 2006/0173382 A1 | 8/2006 | Schreiner |
| 2006/0190022 A1 | 8/2006 | Beyar et al. |
| 2006/0211752 A1 | 9/2006 | Kohn et al. |
| 2006/0247756 A1* | 11/2006 | Richter ............... A61F 2/856 623/1.11 |
| 2006/0271024 A1 | 11/2006 | Gertner et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0208252 A1 | 9/2007 | Makower |
| 2007/0208301 A1 | 9/2007 | Evard et al. |
| 2007/0244501 A1 | 10/2007 | Horn et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293929 A1 | 12/2007 | Aoba et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0033525 A1* | 2/2008 | Shaked ............... A61B 17/1214 623/1.11 |
| 2008/0051804 A1 | 2/2008 | Cottler et al. |
| 2008/0103521 A1 | 5/2008 | Makower et al. |
| 2008/0119693 A1 | 5/2008 | Makower et al. |
| 2008/0132938 A1 | 6/2008 | Chang et al. |
| 2008/0154343 A1 | 6/2008 | Li et al. |
| 2008/0183128 A1 | 7/2008 | Morriss et al. |

(56) References Cited

U.S. PATENT DOCUMENTS

| | | |
|---|---|---|
| 2008/0188870 A1 | 8/2008 | Andre et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0105641 A1* | 4/2009 | Nissl .......... A61M 25/104 604/97.02 |
| 2009/0125002 A1* | 5/2009 | Totz .......... A61J 15/0003 604/528 |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0187144 A1 | 7/2009 | Jayaraman |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0042046 A1 | 2/2010 | Chang et al. |
| 2010/0087811 A1 | 4/2010 | Herrin et al. |
| 2010/0114066 A1 | 5/2010 | Makower et al. |
| 2010/0198191 A1 | 8/2010 | Clifford et al. |
| 2010/0274188 A1 | 10/2010 | Chang et al. |
| 2015/0202089 A1 | 7/2015 | Campbell et al. |
| 2015/0250992 A1 | 9/2015 | Morriss et al. |

FOREIGN PATENT DOCUMENTS

| | | |
|---|---|---|
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 257605 | 3/1988 |
| EP | 355996 | 2/1990 |
| EP | 418391 | 3/1991 |
| EP | 427852 | 5/1991 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | S 53-67935 | 6/1978 |
| JP | H 10-24098 | 1/1989 |
| JP | H 03-503011 | 7/1991 |
| JP | H 03-504935 | 10/1991 |
| JP | H 04-221313 | 8/1992 |
| JP | H 04-224766 | 8/1992 |
| JP | H 05-211985 | 8/1993 |
| JP | H06-233823 A | 8/1994 |
| JP | H 06-277296 | 10/1994 |
| JP | H 07-327916 | 12/1995 |
| JP | H 08-317989 | 12/1996 |
| JP | H10-179751 A | 7/1998 |
| JP | H 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-523138 A | 7/2002 |
| JP | 2002-537908 | 11/2002 |
| JP | 2002-538850 | 11/2002 |
| JP | 2002-539888 A | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| JP | 2005-538945 A | 12/2005 |
| JP | 2006-514855 A | 5/2006 |
| JP | 2007-301062 A | 11/2007 |
| JP | 2007-537784 A | 12/2007 |
| JP | 2008-508938 A | 3/2008 |
| JP | 2008-531086 A | 8/2008 |
| JP | 2009-500051 A | 1/2009 |
| JP | 2013-176504 A | 9/2013 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 96/029071 | 9/1996 |
| WO | WO 97/021461 | 6/1997 |
| WO | WO 99/024106 | 5/1999 |
| WO | WO 99/030655 | 6/1999 |
| WO | WO 99/032041 | 7/1999 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 01/045572 | 6/2001 |
| WO | WO 01/054558 | 8/2001 |
| WO | WO 01/056481 | 8/2001 |
| WO | WO 01/070325 | 9/2001 |
| WO | WO 01/074266 | 10/2001 |
| WO | WO 01/097895 | 12/2001 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

European Communication dated Nov. 8, 2018 for Application No. 10801347.5, 5 pages.

Argon Medical. Maxxim Medical. Ad for Sniper Elite™ Hydrophilic Ni—Ti Alloy Guidewire (2001).

Aust, R., et al. 'The Functional Size of the Human Maxillary Ostium in Vivo' Acta. Otolaryn. (9178) vol. 78 pp. 432-435.

(56) References Cited

OTHER PUBLICATIONS

Baim, D.S., MD 'Grossman's Cardiac Catheterization, Angiography, and Intervention' (2000) Lippincott Williams & Wilkins pp. 76, 84 & 214.

Barrett, S. 'Be Wary of Neurocranial Restructuring (NCR)' Chirobase; Jul. 2003; www.chirobase.org/06DD/ncr.html.

Bartal, N. 'An Improved stent for Use in the Surgical Management of Congential Posterior Choanal Atresia' J. Laryngol. Otol (1988) vol. 102 pp. 146-147.

Becker, A.E. 'Restenosis After Angioplasty' The Lancet (1988) vol. 331, No. 8584 p. 532.

Bellis, M. History of the Catheter-Balloon Catheter—Thomas Fogarty. Www.inventors.about.com/library/inventors/blcatheter.htm?p=1.

Benninger et al.; Adult Chronic Rhinosinusitis: Definitions, Diagnosis, Epidemiology, and Pathophysiology Arch Otolarygol Head and Neck Surg. vol. 129 (Sep. 2003) pp. A1-S32.

Bent et al. 'The Frontal Cell as a Cause of Frontal Sinus Obstruction' American Journal of Rhinology, vol. 8, No. 4 (1994) pp. 185-191.

Binner et al. 'Fibre-Optic Transillumination of the Sinuses: A Comparison of the Value of Radiography and Transillumination in Antral Disease' Clinical Otolaryngology. vol. 3 (1978) pp. 1-11.

Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.

Casiano et al. 'Endoscopic Lothrop Procedure: The University of Miami Experience' American Journal of Rhinology, vol. 12, No. 5 (1998) pp. 335-339.

Casserly, I.P. et al., Chapter 7. 'Guides and Wires in Percutaneous Coronary Intervention' Strategic Approaches in Coronary Intervention (2006) Lippincott Williams & Wilkins pp. 91-99.

Chien, Y.W. et al. 'Nasal Systemic Drug Delivery' Drugs and Pharmaceutical Sciences, vol. 39, pp. 60-63.

Cohen et al. 'Endoscopic Sinus Surgery: Where we are and where we're going' Current Opinion in Otolaryngology & Head and Neck Surgery, vol. 13 (2005) pp. 32-38.

Colla, A. et al., 'Trihaloacetylated Enol Ethers—General Synthetic Procedure and Heterocyclic Ring Closure Reactions with Hydroxylamine' Synthesis, (Jun. 1991) pp. 483-486.

Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.

Cussler, E.L. 'Diffusion: Mass transfer in Fluid Systems' Cambridge University Press (1996).

Davis, G.E. et al. 'A Complication from Neurocranial Restructuring' Arch Otolaryngol Head Neck Surg. vol. 129 (Apr. 2003) pp. 472-474.

Deutschmann, R. et al. 'A Contribution to the Topical Treatment of [Maxillary] Sinusitis Preliminary Communication' Stomat DDR 26, (1976) pp. 585-592.

Domb, A. et al. 'Handbook of Biodegradable Polymers' Harwood Academic Publishers (1997).

Doyle Nasal Splints, Jan. 25, 2007; www.doylemedical.com/nasalsplints.htm.

Draf, W. 'Endonasal Micro-Endoscopic Frontal Sinus Surgery: the Fulda Concept' Op Tech Otolaryngol Head Neck Surg. vol. 2 (1991) pp. 234-240.

Edmond, C. et al. 'ENT Surgical Stimulator' Nov. 1989.

ENT Checklist; Physical Examination Performance Checklist [date of publication unknown].

Eremychev, V.A. 'Needles for Puncture and Drainage of the Maxillary Sinus' Meditsinskaya Tekhnika, No. 5 (1974) pp. 54.55.

Feldman, R.L. et al., 'New Steerable, Ultra-Low-Profile, Fixed Wire Angioplasty Catheter: Initial Experience with the Cordis OrionTM Steerable PTCA Balloon Catheter' Cathet. Cardiovasc. Diagn. (1990) vol. 19, No. 2 pp. 142-145.

Ford, C.N. 'A Multipurpose Laryngeal Injector Device' Otolaryngol. Head Neck Surg. (1990) vol. 103, No. 1 pp. 135-137.

Friedman, M., M.D., et al. A Safe, Alternative Technique for Inferior Turbine Reduction. Nov. 1999. The Laryngoscope, 109. p. 1834-37 (4 pages).

Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.

Friedman, et al. 'Intraoperative and Postoperative Assessment of Frontal Sinus Patency by Transillumination' Laryngoscope. vol. 110 (Apr. 2000) pp. 683-684.

Friedman, et al 'Middle Turbinate Medialization and Preservation in Endoscopic Surgery' Otolaryngology—Head and Neck Surgery. (2000) vol. 123, No. 1, part 1, pp. 76-80.

Fung, M.K.T. 'Template for Frontal Osteoplastic Flap' Laryngoscope. vol. 96 (1986) pp. 578-579.

Gatot, A. et al. 'Early treatment of Orbital Floor Fractures with Catheter Balloon in Children' Int J. Pediatric Otorhinolaryngol (1991) vol. 21 pp. 97-101.

Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elsevier Science S.A.

Good, R.H. 'An Intranasal Method for Opening the Frontal Sinus Establishing the Largest Possible Drainage' Laryngoscope. vol. 18 (1908) pp. 266-274.

Gopferich 'Polymer Degradation and Erosion: Mechanisms and Application' Eur. J. Parm. Biophar. vol. 42 (1996) pp. 1-11.

Gorlov, D.V. et al 'Acylation of 2-Methoxypropene with Anhydrides and Halides of Perflurocarboxylic Acids in the Presence of Tertiary Amines' Russian Chemical Bulletin. vol. 48 No. 9 (Sep. 1999) pp. 1791-1792. Kluwer Academic/Plenum Publishers.

Gottmann, et al. 'Balloon Dilatation in the Nasal Cavity and Paranasal Sinuses' CIRSE. (Sep. 25, 2004) pp. 1-27.

Gottmann, et al. 'Balloon Dilatation of Recurrent Ostial Occlusion of the Frontal Sinus' CIRSE Abstract (Mar. 2001) B-04353.

Gottmann, et al. 'Successful Treatment of Recurrent Post-Operative Frontal Sinus Stenoses by Balloon Dilatation' CIRSE. (Oct. 5, 2002).

Gottmann, D. 'Treatment of Stenoses of Upper Air Routes by Balloon Dilation' Proceeding of the 83rd Annual Convention of Association of West German ENT Physicians (1999).

Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.

Hashim, et al. 'Balloon Compression of the Intermaxillary Sinus for Intractable Post Traumatic Bleeding from the Maxillary Artery' Scandinavian Journal of Plastic and reconstruction Surgery and Hand Surgery (1999) vol. 33 pp. 321-324.

Hojo, M. et al, 'Electrophilic Substitutions of Olefinic Hydrogens II. Acylation of Vinyl Ethers and N Vinyl Amides Chemistry Letters' (1976) pp. 499-502. Chemical Society of Japan.

Hopf, J.U.G. et al. 'Miniature Endoscopes in Otorhinolaryngologic Applications' Min Invas Ther & Allied Technol. (1998) vol. 7, No. 3 pp. 209-218.

Hosemann, W. et al. A Dissection Course on Endoscopic Endonasal Sinus Surgery (2005) Endo-Press, Tuttlingen pp. 4-37.

Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.

Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.

Hosemann, W.G. et al. 'Minimally Invasive Endonasal Sinus Surgery' Thieme, Stuttgart, New York (2000).

Hosemann, M.E. et al. 'Normal Wound Healing of the Paranasal Sinuses—Clinical and Experimental Investigations' Eur Arch Otorhinolarygol. vol. 248, (1991) pp. 390-394.

Hosemann, W. et al. 'Behandlung nach Nasennebenhohleneingriffen, part 2: Theapeutische Maßnahem' HNO akutell 7 (1999) pp. 291-302.

(56) References Cited

OTHER PUBLICATIONS

Hospital Corpsman Sickcall Screener's Handbook. Naval Hospital Great Lakes (Apr. 1999) www.brooksidepress.org/Products/Operationa.Medicine/DATA. 2001 pp. 1-6.
Hybels, R.L. 'Transillumination During Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' The Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kaneko, Akihiro, et al., "Direct Measurement of Eustachian Tube Compliance", 1996, Acta Otolaryngol, Scandinavian University Press, vol. 116, p. 594-598 (5 pages).
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 ( Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' International Advanced Sinus Symposium Jul. 21-24, 1993.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com—MicroFrance Catalog Browser. Www.xomcat.com/xomfrance/index.php?zone=both&cat=18&sub=58&prodline-1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al. 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Metson, R. et al. Microdebrider eustachian tuboplasty: A preliminary report. Available online Mar. 2007. Otolaryngology—Head and neck Surgery. vol. 136. p. 422-27 (6 pages).
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxillary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.
Park, K. et al. 'Biodegradable Hydrogels for Drug Delivery' (1993) Technomic Publishing Inc. Lancaster.
Piccirillo, J.F. et al. 'Psychometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Poe, D. S. et al. Laser Eustachian Tuboplasty: A Preliminary Report. Apr. 2003. The Laryngoscope, 113. p. 583-91 (9 pages).
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluoroscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.

(56) References Cited

OTHER PUBLICATIONS

Single-Pole and Multi-Pole Lightguides for UV Spot Light Curing Systems.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steroid Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow, [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying copy of poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile Monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action, Patent Examination Report No. 1, dated Feb. 17, 2015 for Application No. AU 2010339585, 2 pgs.
Australian Office Action, Patent Examination Report No. 2, dated Feb. 1, 2016 for Application No. AU 2010339585, 3 pgs.
Chinese Office Action, First Office Action, and Search Report dated Apr. 9, 2014 for Application No. CN 201080060564.4, 6 pgs.
Chinese Office Action, Second Office Action, dated Mar. 2, 2015 for Application No. CN 201080060564.4, 3 pgs.
Chinese Office Action, Third Office Action, dated Dec. 2, 2015 for Application No. CN 201080060564.4, 3 pgs.
European Communication dated Sep. 4, 2008 for Application No. EP 05773189.
European Communication dated Jun. 19, 2009 for Application No. EP 05773189.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report and Written Opinion dated Sep. 27, 2011 for Application No. EP 10182961.
European Search Report and Written Opinion dated Sep. 29, 2011 for Application No. EP 10182893.
Partial European Search Report dated Sep. 20, 2007 for Application No. EP 07252018.
Partial European Search Report dated Mar. 25, 2008 for Application No. EP 07252018.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jun. 2, 2008 for Application No. EP 05773189.
Supplemental European Search Report dated Jan. 29, 2010 for Application No. EP 07836108.
Supplemental European Search Report dated Feb. 2, 2010 for Application No. EP 07836109.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
International Preliminary Report on Patentability and Written Opinion dated Aug. 7, 2006 for Application No. PCT/US2005/25371.
International Preliminary Report on Patentability and Written Opinion dated Sep. 25, 2007 for Application No. PCT/US2006/002004.
International Preliminary Report on Patentability and Written Opinion dated Nov. 18, 2008 for Application No. PCT/US2007/11449.
International Preliminary Report on Patentability and Written Opinion dated Apr. 7, 2009 for Application No. PCT/US2007/021170.
International Preliminary Report on Patentability and Written Opinion dated May 5, 2009 for Application No. PCT/US2006/036960.
International Preliminary Report on Patentability and Written Opinion dated Oct. 13, 2009 for Application No. PCT/US2008/059786.
International Preliminary Report on Patentability and Written Opinion dated Oct. 27, 2009 for Application No. PCT/US2008/061343.
International Preliminary Report on Patentability and Written Opinion dated Mar. 26, 2013 for Application No. PCT/US2011/052321.
International Search Report dated Jun. 3, 2002 for Application No. PCT/EP02/01228.
International Search Report and Written Opinion dated Apr. 10, 2006 for Application No. PCT/US2005/25371.
International Search Report and Written Opinion dated May 8, 2007 for Application No. PCT/US2006/016026.
International Search Report and Written Opinion dated Aug. 17, 2007 for Application No. PCT/US2005/013617.

(56) References Cited

OTHER PUBLICATIONS

International Search Report and Written Opinion dated Aug. 29, 2007 for Application No. PCT/US2006/002004.
International Search Report and Written Opinion dated Sep. 25, 2007 for Application No. PCT/US2006/037167.
International Search Report and Written Opinion dated Oct. 19, 2007 for Application No. PCT/US2007/003394.
International Search Report and Written Opinion dated May 29, 2008 for Application No. PCT/US2007/021170.
International Search Report and Written Opinion dated May 29, 2008 for Application No. PCT/US2007/021922.
International Search Report and Written Opinion dated Jul. 1, 2008 for Application No. PCT/US2006/022745.
International Search Report and Written Opinion dated Jul. 3, 2008 for Application No. PCT/US2006/029695.
International Search Report and Written Opinion dated Jul. 7, 2008 for Application No. PCT/US2007/016213.
International Search Report and Written Opinion dated Jul. 8, 2008 for Application No. PCT/US2007/011474.
International Search Report and Written Opinion dated Jul. 17, 2008 for Application No. PCT/US2006/036960.
International Search Report and Written Opinion dated Jul. 21, 2008 for Application No. PCT/US2005/033090.
International Search Report and Written Opinion dated Aug. 25, 2008 for Application No. PCT/US2008/000911.
International Search Report and Written Opinion dated Sep. 10, 2008 for Application No. PCT/US2007/016212.
International Search Report and Written Opinion dated Sep. 12, 2008 for Application No. PCT/US2007/016214.
International Search Report and Written Opinion dated Sep. 17, 2008 for Application No. PCT/US2008/059786.
International Search Report and Written Opinion dated Sep. 17, 2008 for Application No. PCT/US2008/061343.
International Search Report and Written Opinion dated Oct. 1, 2008 for Application No. PCT/US2007/011449.
International Search Report and Written Opinion dated Oct. 15, 2008 for Application No. PCT/US2008/061048.
International Search Report and Written Opinion dated Nov. 30, 2009 for Application No. PCT/US2009/057203.
International Search Report and Written Opinion dated Dec. 10, 2009 for Application No. PCT/US2009/052236.
International Search Report and Written Opinion dated Dec. 16, 2009 for Application No. PCT/US2009/050800.
International Search Report and Written Opinion dated Mar. 31, 2010 for Application No. PCT/US2009/069143.
International Search Report and Written Opinion dated Jul. 8, 2010 for Application No. PCT/US2010/027837.
International Search Report and Written Opinion dated Oct. 6, 2010 for Application No. PCT/US2010/040548.
International Search Report and Written Opinion dated Mar. 25, 2011 for Application No. PCT/US2010/062161.
International Search Report and Written Opinion dated Mar. 28, 2011 for Application No. PCT/US2010/061850.
International Search Report and Written Opinion dated Mar. 31, 2011 for Application No. PCT/US2010/060898.
International Search Report and Written Opinion dated Aug. 9, 2011 for Application No. PCT/US2011/038751.
International Search Report and Written Opinion dated May 18, 2012 for Application No. PCT/US2011/052321.
International Search Report and Written Opinion dated Jun. 27, 2016 for Application No. PCT/US2016/024978, 14 pgs.
Japanese Office Action, Notification of Reasons for Refusal, dated Oct. 21, 2014 for Application No. JP 2012-547223, 2 pgs.
Japanese Office Action, Notification of Reasons for Refusal, dated Nov. 17, 2015 for Application No. JP 2015-005722, 3 pgs.
Korean Office Action, Notice of Preliminary Rejection, dated Nov. 30, 2016 for Application No. 10-2012-7019752, 8 pgs.
Mexican Office Action, Requirement 1, dated Jul. 22, 2014 for Application No. MX/a/2012/007725, 3 pgs.
Mexican Office Action, Requirement 2, dated Feb. 6, 2015 for Application No. MX/a/2012/007725, 3 pgs.
Mexican Office Action, Requirement 3, dated Jul. 23, 2015 for Application No. MX/a/2012/007725, 3 pgs.
Russian Office Action, Official Action, for Application No. RU 2012132456, 5 pgs.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.

(56) References Cited

OTHER PUBLICATIONS

USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/789,705, filed Apr. 24, 2007.
Japanese Office Action, Notice of Reasons for Refusal, and Search Report by Registered Searching Organization, dated Mar. 3, 2020 for Application No. JP 2017-551293, 16 pgs.
Chinese First Office Action and Search Report dated Dec. 19, 2019 for Application No. 201680031186.4, 6 pages.
Chinese Second Office Action and Supplementary Search Report dated Jul. 1, 2020 for Application No. 201680031186.4, 7 pages.

* cited by examiner

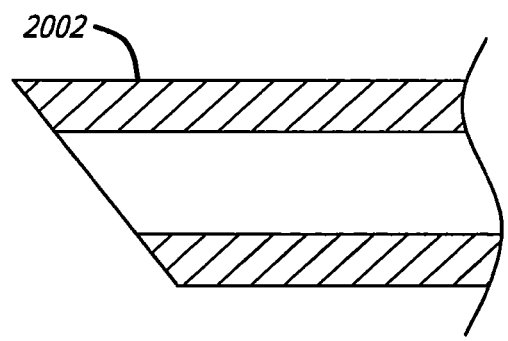
FIG. 20A
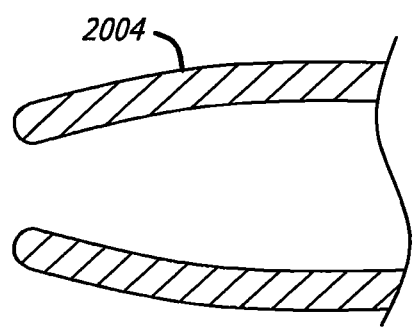
FIG. 20B
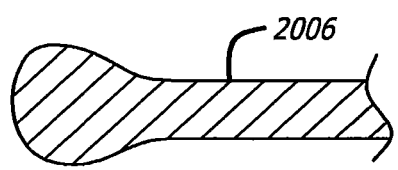
FIG. 20C
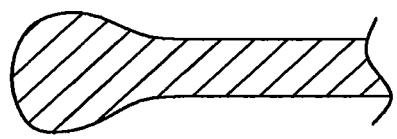

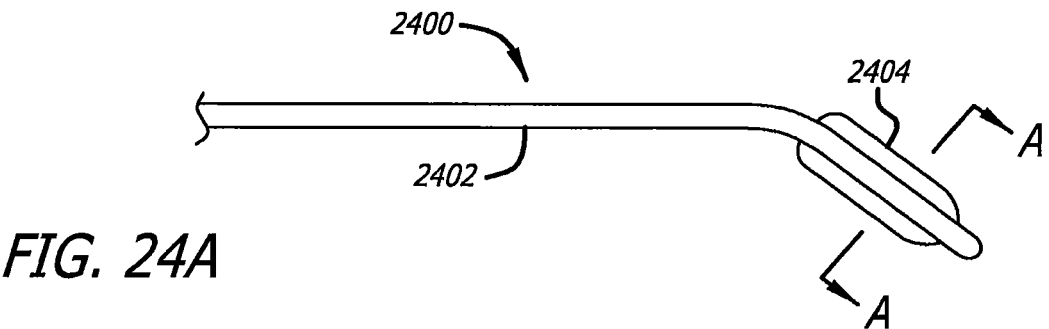
FIG. 24A
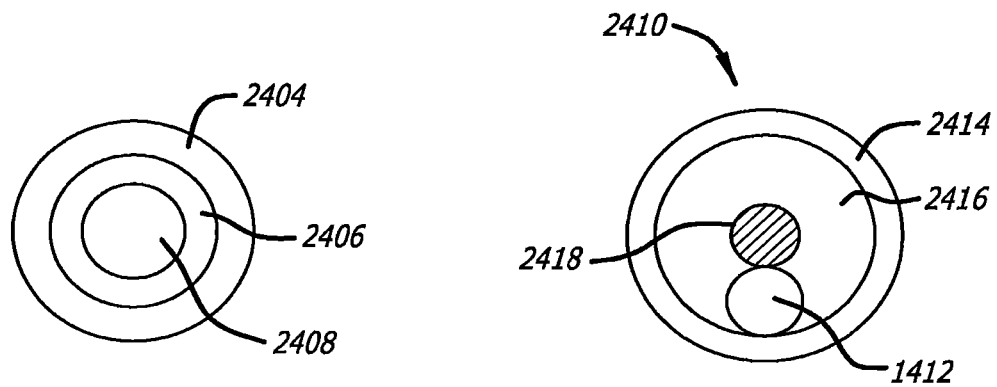
FIG. 24B
FIG. 24C

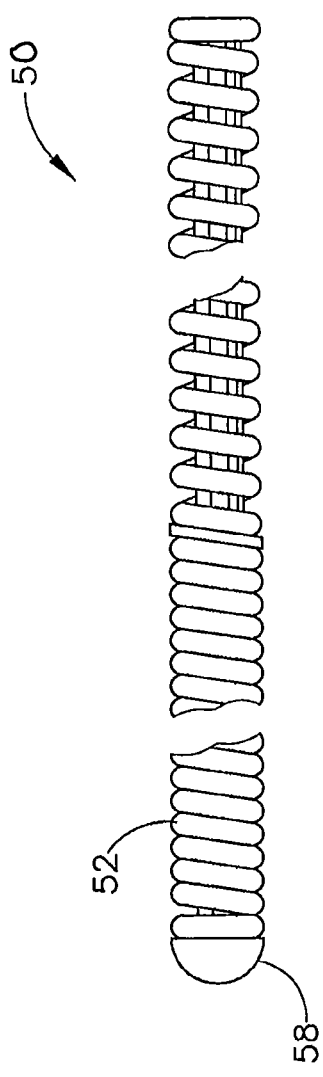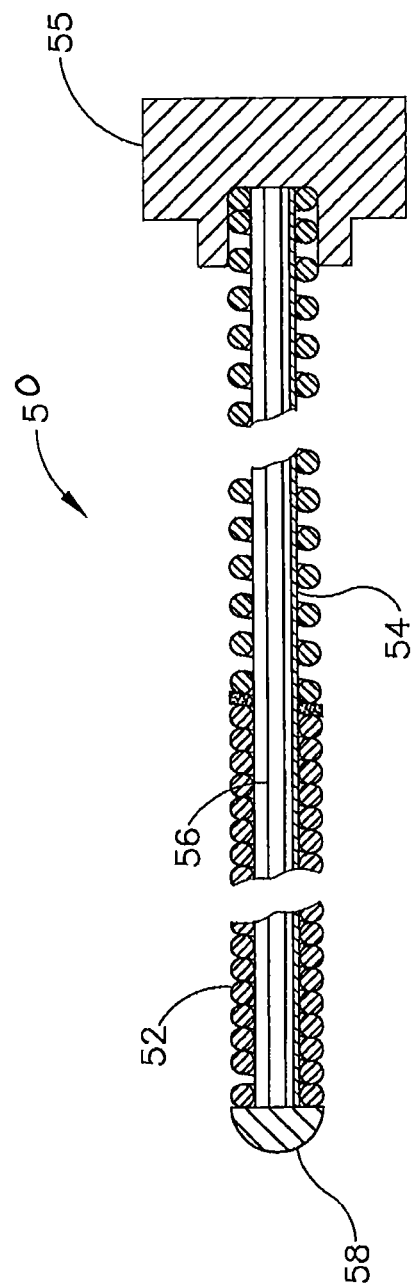
Fig. 30
Fig. 31

EUSTACHIAN TUBE DILATION BALLOON WITH VENTILATION PATH

PRIORITY

This application is a continuation of U.S. patent application Ser. No. 14/674,639, filed Mar. 31, 2015 (published on Jul. 23, 2015 as U.S. Pub. No. 2015/0202089), which is a continuation-in-part of U.S. patent application Ser. No. 12/777,856, filed on May 11, 2010 (published on Oct. 28, 2010 as U.S. Pub. No. 2010/0274188), now abandoned, which is a continuation-in-part of U.S. patent application Ser. No. 12/649,078, filed on Dec. 29, 2009 (published on Aug. 5, 2010 as U.S. Pub. No. 2010/0198191), now abandoned, which is a continuation-in-part of U.S. patent application Ser. No. 12/340,226, filed on Dec. 19, 2008 (published on Jun. 25, 2009 as U.S. Pub. No. 2009/0163890), now abandoned, which claims the benefit of U.S. Provisional Pat. App. No. 61/015,647, filed on Dec. 20, 2007. All the disclosures of the above listed references are hereby incorporated by reference in their entirety for all purposes.

BACKGROUND OF THE INVENTION

The present invention is related to methods and systems for accessing, diagnosing and treating target tissue regions within the middle ear and the Eustachian tube.

Referring to FIGS. 1-2, the ear 10 is divided into three parts: an external ear 12, a middle ear 14 and an inner ear 16. The external ear 12 consists of an auricle 18 and ear canal 20 that gather sound and direct it towards a tympanic membrane 22 (also referred to as the eardrum) located at an inner end 24 of the ear canal 20. The middle ear 14 lies between the external and inner ears 12 and 16 and is connected to the back of the throat by a Eustachian tube 26 which serves as a pressure equalizing valve between the ear 10 and the sinuses. The Eustachian tube 26 terminates in a distal opening 28 in the nasopharynx region 30 of the throat 32. In addition to the eardrum 22, the middle ear 14 also consists of three small ear bones (ossicles): the malleus 34 (hammer), incus 36 (anvil) and stapes 38 (stirrup). These bones 34-38 transmit sound vibrations to the inner ear 16 and thereby act as a transformer, converting sound vibrations in the canal 20 of the external ear 12 into fluid waves in the inner ear 16. These fluid waves stimulate several nerve endings 40 that, in turn, transmit sound energy to the brain where it is interpreted.

The Eustachian tube 26 is a narrow, one-and-a-half inch long channel connecting the middle ear 14 with the nasopharynx 30, the upper throat area just above the palate, in back of the nose. The Eustachian tube 26 functions as a pressure equalizing valve for the middle ear 14 which is normally filled with air. When functioning properly, the Eustachian tube 26 opens for a fraction of a second periodically (about once every three minutes) in response to swallowing or yawning. In so doing, it allows air into the middle ear 14 to replace air that has been absorbed by the middle ear lining (mucous membrane) or to equalize pressure changes occurring on altitude changes. Anything that interferes with this periodic opening and closing of the Eustachian tube 26 may result in hearing impairment or other ear symptoms.

Obstruction or blockage of the Eustachian tube 26 results in a negative middle ear pressure 14, with retraction (sucking in) of the eardrum 22. In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear 14, creating a condition referred to as serous otitis media (fluid in the middle ear). This occurs frequently in children in connection with an upper respiratory infection and accounts for the hearing impairment associated with this condition.

A lining membrane (mucous membrane) of the middle ear 14 and Eustachian tube 26 is connected with, and is the same as, the membrane of the nose 42, sinuses 44 and throat 32. Infection of these areas results in mucous membrane swelling which in turn may result in obstruction of the Eustachian tube 26. This is referred to as serous otitis media, i.e. essentially a collection of fluid in the middle ear 14 that can be acute or chronic, usually the result of blockage of the distal opening 28 of the Eustachian tube 26 which allows fluid to accumulate in the middle ear 14. In the presence of bacteria, this fluid may become infected, leading to an acute suppurative otitis media (infected or abscessed middle ear). When infection does not develop, the fluid remains until the Eustachian tube 26 again begins to function normally, at which time the fluid is absorbed or drains down the tube into the throat 32 through the Eustachian tube opening 28.

Chronic serous otitis media may result from longstanding Eustachian tube blockage, or from thickening of the fluid so that it cannot be absorbed or drained down the Eustachian tube 26. This chronic condition is usually associated with hearing impairment. There may be recurrent ear pain, especially when the individual catches a cold. Fortunately, serous otitis media may persist for many years without producing any permanent damage to the middle ear mechanism. The presence of fluid in the middle ear 14, however, makes it very susceptible to recurrent acute infections. These recurrent infections may result in middle ear damage.

When the Eustachian tube 26 contains a build-up of fluid, a number of things will occur. First, the body absorbs the air from the middle ear 14, causing a vacuum to form which tends to pull the lining membrane and ear drum 22 inward, causing pain. Next, the body replaces the vacuum with more fluid which tends to relieve the pain, but the patient can experience a fullness sensation in the ear 10. Treatment of this condition with antihistamines and decongestants can take many weeks to be fully effective. Finally, the fluid can become infected, which is painful and makes the patient feel ill and which may cause the patient not to be able to hear well. If the inner ear 14 is affected, the patient may feel a spinning or turning sensation (vertigo). The infection is typically treated with antibiotics.

However, even if antihistamines, decongestants and antibiotics are used to treat an infection or other cause of fluid build-up in the middle ear 14, these treatments will typically not immediately resolve the pain and discomfort caused by the buildup of fluid in the middle ear 14; i.e. the most immediate relief will be felt by the patient if the fluid can be removed from the Eustachian tube 26.

Antibiotic treatment of middle ear infections typically results in normal middle ear function within three to four weeks. During the healing period, the patient can experience varying degrees of ear pressure, popping, clicking and fluctuation of hearing, occasionally with shooting pain in the ear. Resolution of the infection occasionally leaves the patient with uninfected fluid in the middle ear 14, localized in the Eustachian tube 26.

Fluid build-up caused by these types of infections has been treated surgically in the past. The primary objective of surgical treatment of chronic serous otitis media is to reestablish ventilation of the middle ear, keeping the hearing at a normal level and preventing recurrent infection that might damage the eardrum membrane and middle ear bones.

For example, as shown in FIG. 3, a myringotomy can be performed to relieve fluid in the middle ear 14. A myringotomy is an incision 42 in the eardrum 22 performed to remove fluid in the middle ear 14. A hollow plastic tube 44, referred to as a ventilation tube, is inserted and lodged in the incision 42 to prevent the incision 42 from healing and to ensure ventilation of the middle ear 14. The ventilation tube 44 temporarily takes the place of the Eustachian tube 26 in equalizing the pressure in the middle ear 14. The ventilation tube 44 usually remains in place for three to nine months during which time the Eustachian tube 26 blockage subsides. When the tube 44 dislodges, the eardrum 22 heals; the Eustachian tube 26 then resumes its normal pressure equalizing function.

Another method of relieving the pressure in the middle ear 14 is shown in FIG. 4 in which a hypodermic needle 46 is driven through the eardrum 22 through which any accumulated fluid can be withdrawn from typically only the upper portion of the Eustachian tube 26.

The methods of FIGS. 3 and 4 involve rupturing the eardrum 22 to relieve the fluid accumulation and pressure increase in the middle ear. Neither of these methods, in addition to the sometimes permanent puncture created in the eardrum 22, is especially effective in removing all of the fluid in the Eustachian tube 26 since often the lower end 28 thereof is blocked and dammed with fluid.

In connection with the above surgical treatments of FIGS. 3 and 4, Eustachian tube 26 inflation is also employed to relieve the pressure build-up and fluid accumulation as shown in FIG. 5. The hypodermic syringe 46 (shown with a flexible tip 48) is inserted into a nostril or into the mouth until the tip 48 is positioned adjacent the distal opening 28 of the Eustachian tube 26 in the nasopharynx region 30 of the throat 32. Air is blown through the tip 48 via the syringe 46 into the obstructed Eustachian tube 26 and, thus, into the middle ear 14 to help relieve the congestion and reestablish middle ear ventilation. This procedure is often referred to as politzerization. Politzerization is most effective when one of the nostrils is pinched shut (as shown in FIG. 6), while the patient simultaneously swallows. This forces air into the Eustachian tube 26 and the middle ear 14. This technique is good for opening the Eustachian tube 26 but it does not clear accumulated fluid away.

Another method for clearing the middle ear 14 (at least temporarily) is referred to as the "valsalva" maneuver, accomplished by forcibly blowing air into the middle ear 14 while holding the nose, often called popping the ear. This method is also good for opening the Eustachian tube 26 but it does not clear the accumulated fluid away either.

Typical disorders associated with the middle ear and the Eustachian tube include perforated ear drums, tympanosclerosis, incus erosion, otitis media, cholesteotoma, mastoiditis, patulous Eustachian tube, and conductive hearing loss. To treat some of these disorders, ear surgery may be performed. Most ear surgery is microsurgery, performed with an operating microscope. Types of ear surgery include stapedectomy, tympanoplasty, myringotomy and ear tube surgery.

One of the simplest ear surgeries is the myringotomy or the incision of the ear drum. However, ear surgery can also require the removal of the tympanic membrane for the visualization of the middle ear space. Often surgeons will try to preserve the integrity of the membrane by making incisions in the skin of the ear canal and removing the tympanic membrane as a complete unit. Alternatively, middle ear access is achieved via the mastoids. This method approaches the middle ear space from behind the ear and drills through the mastoid air cells to the middle ear. Whether the bony partition between the external ear canal and the mastoid is removed or not depends on the extent of the disease. Canal-wall-down refers to the removal of this bony partition. Canal-wall-up refers to keeping this bony partition intact. The term modified radical mastoidectomy refers to an operation where this bony partition is removed and the eardrum and ossicles are reconstructed. A radical mastoidectomy is an operation where this bony partition is removed and the ear drum, malleus and incus bones are permanently removed so that the inner lining of the large cholesteotoma sac can be safely cleaned. This operation is done when an extensive cholesteotoma is encountered or one that is adherent to the inner ear or facial nerve.

Afflictions of the middle ear and Eustachian tube are very prevalent and a serious medical problem, afflicting millions of people and causing pain, discomfort and even hearing loss or permanent ear damage. Although a number of treatments have been developed, as described above each of them has shortcomings. Therefore, a need exists for improved methods and systems for accessing, diagnosing and treating target tissue regions within the middle ear and the Eustachian tube. Ideally, such methods and systems would be minimally invasive and pose very little risk of damage to healthy ear tissue.

SUMMARY

The embodiments of the present invention are directed toward methods and systems for accessing, diagnosing and treating target tissue regions within the middle ear and the Eustachian tube.

In one aspect, the present invention provides a method for accessing a Eustachian tube of a patient. The method may involve inserting a guide catheter into a nasal passage of the patient, the guide catheter having a distal tip with a bend having an angle between 30 and 90 degrees, and advancing the guide catheter in the nasal passage toward an opening of the Eustachian tube in the nasopharynx to place the distal tip adjacent the Eustachian tube opening.

In one embodiment, the method may also include advancing a diagnostic device through the guide catheter to place a distal tip of the diagnostic device adjacent the Eustachian tube opening. The diagnostic device may be a catheter or an endoscope.

In another embodiment, the method may involve introducing a diagnostic probe into the Eustachian tube to directly assess Eustachian tube function. The diagnostic probe may be made from a flexible and Eustachian tube compatible material. The diagnostic probe may be a pressure transducer located on a guidewire. The method may also include monitoring pressure within the Eustachian tube while the patient is swallowing, and assessing an opening function of the patient's Eustachian tube using the monitoring.

In one embodiment, the method may also involve removing the guide catheter after the diagnostic probe is placed into the Eustachian tube.

In one embodiment, the diagnostic probe may include an ultrasound probe.

In another embodiment, the method may also involve advancing a treatment device through the guide catheter toward the Eustachian tube to place a distal tip of the treatment device adjacent the Eustachian tube opening. The treatment device may comprise a distal radiopaque member. The treatment device may comprise a catheter. The treatment device may also comprise a fluid introduction device for introducing a fluid into a middle ear space of the patient's ear. The method may also involve scanning the middle ear space using an ultrasound device. The fluid may be air, a contrast medium, an aspiration fluid, or a drug.

In another embodiment, the treatment device may comprise an aspiration device for aspirating a substance from the middle ear space.

In another embodiment, the method may also involve introducing a protective device proximal the Eustachian tube, and monitoring advancement of the treatment device using the protective device. In one aspect, the protective device may comprise a sensor positioned proximal the tympanic membrane to sense the position of the treatment device during the advancement. The protective device may comprise an endoscope to visualize the advancement.

In another aspect, the present invention provides a method for indirectly assessing Eustachian tube function in a patient. The method may involve positioning an energy emitter in the nasopharynx adjacent a Eustachian tube; positioning an energy receiver adjacent the tympanic membrane via the external ear canal; directing energy from the emitter toward the receiver; generating an emitter signal representative of the energy from the emitter; generating a receiver signal representative of the energy received by the emitter; forming a comparison between the emitter signal and the receiver signal; and indirectly assessing function of the Eustachian tube during swallowing, using the comparison.

In one embodiment, the indirect assessing may involve estimating the physical characteristics of the Eustachian tube.

In another embodiment, the energy emitter may emit energy in the form of a pressure wave or electromagnetic energy.

In another aspect, the present invention provides a method for treating a Eustachian tube in a patient. The method may involve placing a guidewire into a Eustachian tube of the patient via the patient's nasopharynx; introducing a debulking device along the guidewire into the Eustachian tube of the patient; and removing edematous tissue including hypertropic mucosa from a surface along one side of the Eustachian tube.

In one embodiment, the guidewire may include markings and the method may also involve providing feedback related to the introducing into the Eustachian tube.

In another aspect, the present invention provides a method for treating a Eustachian tube in a patient. The method may involve introducing via the patient's nasopharynx a guidewire submucosally between cartilage and a mucosal surface of a Eustachian tube; introducing a debulking device along the guidewire into submucosal tissue of the Eustachian tube, between the cartilage and the mucosal surface; and removing some of the submucosal tissue.

In another aspect, the present invention provides a method for treating muscular dysfunction or an anatomical disorder of a Eustachian tube in a patient. The method may involve creating a lesion in at least one of a tensor villi palatine muscle or a levator villi palatine muscle to affect a stiffening of the muscle(s) upon resorption of the lesion.

In one embodiment, the stiffening may include a shortening or a tensioning of the tensor villi palatine or the levator villi palatine.

In another embodiment, the creating of a lesion may involve applying a therapy from the group including mechanical, laser, radio frequency and chemical therapies.

In another aspect, the present invention provides a method for treating a Eustachian tube in a patient. The method may involve placing a dual lumen pressure equalization tube through the tympanic membrane of the patient, the tube having a distal extension for location in a region of the Eustachian tube; providing a medication to the region of the Eustachian tube through a first lumen of the dual lumen tube in fluid communication with the distal extension; and providing ventilation across the tympanic membrane through a second lumen of the dual lumen tube.

In one embodiment, the medication may be configured to reduce edema in the Eustachian tube region. The medication can include a surfactant configured to modify a surface tension of a mucosal layer of the Eustachian tube to effect an enhanced wetting of the mucosal surface with the medication.

In one embodiment, the medication may include particles configured for capturing by mucosal tissue of the Eustachian tube to effect an extended release of the medication.

In one aspect, the present invention provides an apparatus for treating a Eustachian tube in a patient. The apparatus may include a dual lumen tube for insertion into a tympanic membrane of the patient's ear, the tube having: a distal extension for placement in a region of the Eustachian tube; a first lumen for providing a medication to the region of the Eustachian tube through the distal extension; and a second lumen for providing ventilation across the tympanic membrane.

In one embodiment, the first lumen may be disposed within the second lumen. In another aspect, the second lumen may be disposed within the first lumen. In yet another aspect, the first lumen may be disposed adjacent the second lumen.

In another embodiment, the dual lumen tube may be made from a biodegradable bioresorbable material.

In another aspect, the present invention provides a method for treating a Eustachian tube in a patient. The method may involve accessing a Eustachian tube region via the nasopharynx, using a guide having a lumen; introducing a guidewire through the lumen of the guide to position it submucosally between cartilage and a mucosal surface of the Eustachian tube; passing a temporary intraluminal implant having a drug delivery reservoir along the guidewire to position the implant submucosally in a posterior cushion of the Eustachian tube region between the lumen and the cartilage; and delivering a drug to the Eustachian tube region from the drug delivery reservoir.

In one embodiment, the method may also involve contemporaneously delivering a drug to adenoids and the Eustachian tube region from the drug delivery reservoir.

In one embodiment, the drug delivery reservoir may include a coating layer disposed on the implant.

In another embodiment, the guide may be made from a biodegradable bioresorbable material.

In another aspect, the present invention provides a method for treating a Eustachian tube in a patient. The method may involve obtaining access to a Eustachian tube region via the nasopharynx; introducing via the patient's nasopharynx a hollow guidewire dimensioned to reach into the Eustachian tube region, the hollow guidewire comprising a plurality of apertures disposed at or near its distal end; and delivering a drug to at least one of the Eustachian tube or a middle ear region of the patient's ear through the apertures.

In another aspect, the present invention provides a system for accessing a Eustachian tube of a patient. The system may include a guide configured for passing into a nasal passage of the patient to position a distal tip of the catheter at or near a Eustachian tube, the guide having distal tip with a bend having an angle between 30 and 90 degrees; and a guidewire configured to pass through the guide into the Eustachian tube.

In one embodiment, the guide may include a catheter.

In another embodiment, the guide may include a dual lumen tube.

In another embodiment, the system may also include a diagnostic device configured for passage through the guide.

In another embodiment, the system may also include a treatment device configured for passage through the guide.

In another aspect, the present invention provides a device for treating a Eustachian tube. The device may include an elongate rigid shaft. The device may also include an elongate and flexible insert coupled to the shaft, the insert including a therapeutic device for treating an elongate portion of a Eustachian tube, the insert including a lateral stiffness which deflects in accordance with the Eustachian tube, and a column stiffness which allows the insert to be pushed into the Eustachian tube without buckling.

In one embodiment, the elongate rigid shaft may include a distal end with a bend ranging from 30 to 90 degrees.

In one embodiment, the elongate rigid shaft may include a proximal end which may include at least one fluid fitting for supplying a fluid to the insert.

In one embodiment, the elongate rigid shaft may include a lumen for passage of a guidewire.

In one embodiment, the insert may include a flexible core wire.

In one embodiment, the flexible core wire may be constructed from a super-elastic alloy.

In one embodiment, the flexible core wire may include an atraumatic tip at a distal most portion of the insert.

In one embodiment, the therapeutic device may include a balloon.

In one embodiment, the balloon may include a microporous structure.

In one embodiment, the balloon may be expandable to a preformed shape which matches a profile of a Eustachian tube.

In one embodiment, the balloon may include a drug coating.

In one embodiment, the drug coating may be one of a steroid, antibiotic, antifungal, nonsteroidal anti-inflammatory, steroidal anti-inflammatory, surfactant, or anti-mucoidal substance.

In one embodiment, the therapeutic device may be detachable from the rigid shaft.

In one embodiment, the therapeutic device may include a lumen.

In one embodiment, the therapeutic device may be biodegradable and may include a therapeutic substance.

In one embodiment, the therapeutic substance may be one of a steroid, antibiotic, antifungal, nonsteroidal anti-inflammatory, steroidal anti-inflammatory, surfactant, or anti-mucoidal substance.

In one embodiment, the therapeutic device may include an expandable stent.

In one embodiment, the expandable stent may include a therapeutic substance.

In another aspect, the present invention provides a method for dilating a Eustachian tube of a patient. A guide catheter may be advanced through a nasal passage of the patient to position a distal end of the guide catheter at or near an opening of the Eustachian tube of the patient. A distal portion of the guide catheter may include a bend having an angle between 30 and 90 degrees. The distal portion may be more flexible than a proximal portion of the guide catheter.

A guidewire may be advanced through the guide catheter such that a distal end of the guidewire enters the Eustachian tube. A dilation catheter may be advanced over the guidewire to position a dilator of the dilation catheter within the Eustachian tube. The dilator may be expanded to dilate the Eustachian tube. The dilation catheter and guidewire may be removed from the patient.

In one embodiment, the distal portion of the guide catheter may be malleable, and a bend in the distal portion may be formed by a user of the guide catheter.

In one embodiment, the opening of the Eustachian tube may include a pharyngeal ostium of the Eustachian tube, and the dilation catheter may be advanced to position the dilator in the pharyngeal ostium.

In one embodiment, the guidewire may be an illuminating guidewire. Light may be emitted from the illuminating guidewire, and the emitted light may be viewed.

In one embodiment, the emitted light may be viewed using an endoscope positioned in the patient's head.

In one embodiment, the guide catheter may be removed from the patient before advancing the dilation catheter over the guidewire.

In one embodiment, the dilation catheter may be advanced over the guidewire and through the guide catheter. The removing step may include removing the guide catheter from the patient.

In one embodiment, the dilation catheter may include a balloon dilation catheter, and expanding the dilator may include inflating a balloon of the balloon dilation catheter.

In one embodiment, inflating the balloon may expand a stent within the Eustachian tube.

In one embodiment, the dilation catheter may include lateral wings, and expanding the dilator may include using the lateral wings to maintain the position of the balloon.

In one embodiment, the balloon may be shaped when inflated to match a conical aperture of a pharyngeal ostium of the Eustachian tube ET, and expanding the dilator may include expanding the balloon within the pharyngeal ostium of the Eustachian tube ET.

In one embodiment, the balloon may be shaped to have a cross-section which does not occupy the entirety of the Eustachian tube, and expanding the dilator may include maintaining the balloon in position to relieve pressure within the Eustachian tube.

In one embodiment, the balloon may include cutting members, and expanding the dilator may include cutting the Eustachian tube wall with the cutting members.

In one embodiment, an endoscope may be advanced through the nasal passage, and the dilation catheter may be viewed using the endoscope.

In one embodiment, viewing the dilation catheter includes viewing a marker on a shaft of the catheter. A location of the dilator relative to the opening of the Eustachian tube may be approximated based on a distance of the marker from a proximal end of the dilator.

In one embodiment, at least one substance may be applied to the Eustachian tube using the dilator.

In one embodiment, the dilator may include a porous balloon for delivering the substance.

In one embodiment, the dilator may include a balloon with a plurality of needles for delivering the substance.

In one embodiment, the dilation catheter may apply a force against the Eustachian tube to maintain a position of the dilator during expanding.

In another aspect, the present invention provides a method for dilating a Eustachian tube of a patient. A guide catheter may be advanced through a nasal passage of the patient to position a distal end of the guide catheter at or near an opening of the Eustachian tube of the patient. A distal portion of the guide catheter may include a bend having an angle between 30 and 90 degrees. The distal portion may be more flexible than a proximal portion of the guide catheter. A delivery catheter may be advanced through the guide catheter to place the delivery catheter within the Eustachian tube. An elongate substance delivery device may be delivered into the Eustachian tube using the delivery catheter. The dilation catheter and guidewire may be removed from the patient while leaving the elongate drug delivery device in the Eustachian tube.

In one embodiment, the elongate substance delivery device may be an elongate string configured to elute at least one therapeutic substance.

In one embodiment, delivering the elongate substance delivery device may include internally detaching the elongate string from the delivery catheter.

In one embodiment, delivering the elongate substance delivery device may include externally detaching the elongate polymer string from the delivery catheter.

In one embodiment, the elongate substance delivery device may be a balloon configured to elute the substance over time.

In one embodiment, delivering the elongate drug deliver device may include inflating the balloon within the Eustachian tube and decoupling the balloon from the delivery catheter.

In one embodiment, the balloon may be configured to allow pressure equalization within the Eustachian tube.

In one embodiment, the elongate drug delivery device may be an expandable stent.

In one embodiment, delivering the elongate drug delivery device may include inserting the expandable stent into the Eustachian tube and unconstraining a proximal end of the expandable stent to allow the proximal end of the expandable stent to expand within the Eustachian tube.

In one embodiment, the elongate drug delivery device may be an elongate insert including an elongate central member connected to a plurality of braces, and each brace may be connected to an elongate outer member.

In one embodiment, the braces may provide and maintain open spaces in the Eustachian tube to maintain pressure equalization therein.

In another aspect, a method for dilating an Eustachian tube of a patient may involve: advancing a dilation device through a nasal passage of the patient to position a dilator of the device at least partially in a Eustachian tube of the patient; expanding the dilator to dilate a portion of the Eustachian tube; collapsing the dilator; and removing the dilation device from the patient, wherein the dilated portion of the Eustachian tube remains at least partially dilated after removal of the device. In one embodiment, a distal portion of the dilation device may be malleable, and the method may further involve forming, by a user of the dilation device, a bend in the distal portion. In this embodiment or an alternative embodiment, the distal portion of the dilation device may include a bend of between about 30 degrees and about 90 degrees. In some embodiments, the opening of the Eustachian tube is a pharyngeal ostium of the Eustachian tube, and the dilation device is advanced to position the dilator in the pharyngeal ostium.

In one embodiment, the dilation device may include a guide portion slidably coupled with the dilator. In such an embodiment, advancing the dilation device may involve advancing the dilation device into the nasal cavity to position a distal end of the device at or near the opening of the Eustachian tube and advancing the dilator relative to the guide portion to position the dilator in the opening. In one embodiment, the guide portion may include an outer tube and an inner shaft extending distally beyond the outer tube, and the dilator may be advanced through the tube and over the inner shaft. In one embodiment, the inner shaft may be malleable, and the method further include forming, by a user of the dilation device, a bend in the inner shaft.

In some embodiments, the dilator may be a balloon, and expanding the dilator may involve inflating the balloon. In one embodiment, inflating the balloon may expand a stent within the Eustachian tube. In one embodiment, the balloon may include cutting members, and expanding the dilator may further involve cutting the Eustachian tube wall with the cutting members.

Optionally, the method may further include advancing an endoscope through the nasal passage and viewing at least one of the advancing, expanding, collapsing or removing steps using the endoscope. In one embodiment, viewing may include viewing a marker on the dilation device. In this embodiment, the method may further include approximating a location of the dilator relative to the opening of the Eustachian tube based on a distance of the marker from a proximal end of the dilator.

In one embodiment, the method may further comprise applying at least one substance to the Eustachian tube using the dilator. In one embodiment, the dilator may be a porous balloon for delivering the substance. In another embodiment, the dilator may be a balloon with a plurality of needles for delivering the substance.

In another aspect, a device for dilating an Eustachian tube of a patient may include a handle, a guide member coupled with the handle, a dilator slidably coupled with the handle and disposed over at least part of the guide member, an actuator on the handle for advancing the dilator along the guide member, and an expansion member coupled with the handle for allowing expansion of the dilator. In one embodiment, the dilator may comprise a balloon catheter including an inflatable balloon, and the expansion member may comprise an inflation port in fluid communication with an inflation lumen of the balloon catheter. In one embodiment, the balloon may include multiple apertures through which one or more drugs may be passed to contact the Eustachian tube. In this or another embodiment, the balloon may include at least one cutting member for cutting tissue within the Eustachian tube upon expansion.

In some embodiments, the guide member may comprise a shaft over which the dilator slides. In some embodiments, the shaft is malleable. In this or other embodiments, the shaft may have a bend with an angle of between about 30 degrees and about 90 degrees. In some embodiments, a distal end of the shaft may have a ball tip.

In some embodiments, the advancement member comprises a slide. In some embodiments, the dilator may comprise a rigid proximal portion and a flexible distal portion. In one embodiment, the rigid proximal portion may comprise a hypotube. In one embodiment, the guide member may comprise a tubular shaft through which the dilator slides. In one embodiment, this shaft may be malleable. Additionally or alternatively, the shaft may have a bend with an angle of between about 30 degrees and about 90 degrees.

Optionally, the device may further include a suction port disposed on the handle and in fluid communication with a suction lumen passing through the guide member or the dilator. Also optionally, the device may further include an endoscope connection member for coupling an endoscope with the device.

For a further understanding of the nature and advantages of the invention, reference should be made to the following description taken in conjunction with the accompanying figures. Each of the figures is provided for the purpose of illustration and description only and is not intended to limit the scope of the embodiments of the present invention.

BRIEF DESCRIPTION OF THE DRAWINGS

FIGS. 20A, 20B and 20C show cross-sectional views of distal tips of guide catheters for interfacing with the opening of a Eustachian tube of a patient.

FIGS. 24A-24C are various views of two embodiments of a Eustachian tube balloon dilation catheter coupled with an endoscope.

FIG. 30 shows a side elevational view of an exemplary illuminating guidewire suitable for use with a balloon dilation catheter.

FIG. 31 shows a side cross-sectional view of the illuminating guidewire of FIG. 30.

DETAILED DESCRIPTION OF THE INVENTION

The embodiments of the present invention are directed toward methods and systems for accessing, diagnosing and treating target tissue regions within the middle ear and the Eustachian tube.

Access

Figure 7:
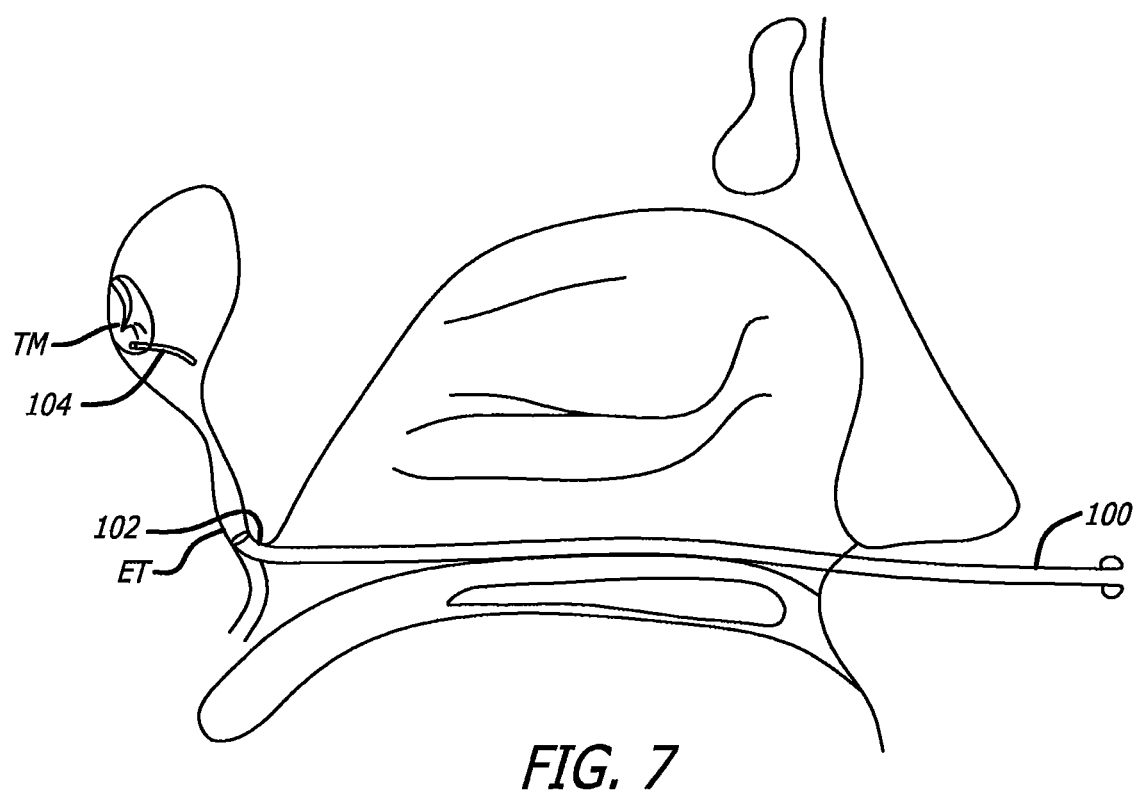
FIG. 7 shows a cross-sectional view of a human head showing the nasopharynx region and a guide catheter in the nasal passage where the distal tip of the guide catheter is adjacent the Eustachian tube opening.

One embodiment of the present invention is directed toward using minimally invasive techniques to gain trans-Eustachian tube access to the middle ear. In one embodiment, a middle ear space may be accessed via a Eustachian tube (ET). To obtain this access to the Eustachian tube orifice, a guide catheter having a bend on its distal tip greater than about 30 degrees and less than about 90 degrees may be used. Once accessed, diagnostic or interventional devices may be introduced into the Eustachian tube. Optionally, to prevent damage to the delicate middle ear structures, a safety mechanism may be employed. In one embodiment, the safety mechanism may include a probe and/or a sensor introduced into the middle ear via the tympanic membrane as shown in FIG. 7. For example, the probe may be an endoscope, and the sensor may be an electromagnetic transducer.

FIG. 7 is a cross-sectional view showing the nasopharynx region and a guide catheter 100 in the nasal passage where the distal tip 102 of the guide catheter 100 is adjacent the Eustachian tube opening. FIG. 7 shows the guide catheter 100 having a bend on its distal tip 102 that is greater than about 30 degrees and less than about 90 degrees located adjacent the Eustachian tube orifice. A sensor 104 located adjacent the tympanic membrane may be used to monitor advancement of the guide catheter 100. The sensor 104 is one example of a safety mechanism.

In various alternative embodiments, the guide catheter 100 may have any suitable length, diameter, angle of bend, and location of the bend along the length of the catheter 100, to facilitate accessing a Eustachian tube opening. In some embodiments, for example, the guide catheter 100 may have a length between about 10 cm and about 20 cm, and more preferably between about 12 cm and about 16 cm. In various embodiments, the guide catheter 100 may have a bend with an angle between about 0 degrees and about 180 degrees, and more preferably between about 30 degrees and about 90 degrees. In one embodiment, for example, the guide catheter 100 may have a length, bend angle and overall configuration to access a Eustachian tube via entry through the nostril on the same side of the head as the Eustachian tube being accessed. In an alternative embodiment, the guide catheter 100 may have a length, bend angle and overall configuration to access a Eustachian tube via entry through a nostril on the opposite (contralateral) side of the head as the Eustachian tube being accessed. The bend angle of this latter embodiment, for example, may be larger than the bend angle of the guide catheter 100 used for same-side access.

In one embodiment, the guide catheter 100 may be malleable, so that a user may bend the guide catheter 100 to a desired shape that at least partially maintain itself during use. In another embodiment, the guide catheter 100 may be steerable. For example, at least a portion of the guide catheter 100 may be partially flexible, and that portion may be steered by a steering mechanism coupled with a proximal end of the catheter 100, such as one or more pull wires or the like. Various embodiments may include one steerable portion or multiple steerable portions. Various embodiments may also include any suitable angle of steerability. For example, one steerable portion may be bendable to an angle of about 30 degrees, and another steerable portion may be bendable to an angle of about 45 degrees. Any combination of angles and steerable portions may be included in various embodiments.

In some embodiments, the guide catheter 100 may be combined with, or be capable of combining with, a flexible or rigid endoscope. In one embodiment, for example, a flexible endoscope may be built in to the body of the guide catheter 100. In another embodiment, the guide catheter 100 may include an endoscope lumen through which a flexible endoscope may be advanced. In yet another embodiment, the guide catheter may include a lumen, clip or other attachment member (or members) for attaching to a rigid endoscope. For example, in some embodiments the guide catheter 100 may be attached to a variable degree of view rigid endoscope such as a swing prism endoscope.

Some embodiments of the guide catheter 100 may include an optional suction port on or near the proximal end, so that catheter 100 may be connected to a vacuum/suction source.

In these embodiments, the guide catheter 100 may include a separate suction lumen, or alternatively, suction may be directed through the same lumen that devices are passed. Some embodiments may include a one-way valve for allowing passage of devices through the guide catheter 100 while maintaining suction pressure.

In use, the guide catheter 100 may be advanced into a nostril and through a nasal cavity to position a distal end of the catheter 100 at, in or near an opening into the Eustachian tube. In one embodiment, the guide catheter 100 may be passed through a nostril to the Eustachian tube on the ipsilateral (same side) of the head. In an alternative embodiment, the guide catheter 100 may be passed through a nostril to the Eustachian tube on the contralateral (opposite side) of the head. Once access to a Eustachian tube is achieved using the guide catheter 100, any of a number of procedures may be performed on the Eustachian tube using any of a number of different devices. Optionally, in some embodiments, the guide catheter 100 may be used to suction out blood and/or other fluids/substances from the Eustachian tube and/or nasal cavity during and/or after advancement of the catheter 100. In alternative embodiments described more fully below, the guide catheter 100 may be eliminated from the procedure, and the Eustachian tube may be accessing and treated with one or more devices without using the catheter 100.

Diagnosis

Another embodiment of the present invention is directed to diagnosis of the condition of the middle ear and its structure. In one embodiment, diagnosis may include use of an endoscope that has been advanced into position through the guide catheter 100 or that is integrated into the guide catheter 100. The design of the endoscope will allow for a 90 degree or more Y axis visualization and a 360 degree rotation. Such an endoscope may be used for assessment of cholesteotomas, ossicle function and/or condition, and the surgical follow-up. An exemplary endoscope that may be adapted as described above may use the IntroSpicio 115 1.8 mm camera developed by Medigus. Such a camera measures approximately 1.8 mm.times.1.8 mm and its small rigid portion allows for the maximum flexibility at the endoscope tip.

Alternatively, ultrasound may be used by injecting a fluid into the middle ear space and the ET and scanning the middle ear and the ET and its structure ultrasonically. Post-procedure the fluid may be aspirated or left to drain through the Eustachian tube. An ultrasound tipped catheter may be advanced up the ET to a position at the middle ear cavity. The ultrasound catheter may then be pulled down the ET and the physician may use an external video monitor to view the structure in and adjacent the ET.

Functional diagnosis of the Eustachian tube may be achieved via direct or indirect assessment. In one embodiment, for direct assessment, the diagnostic system may allow for the dynamic monitoring of the Eustachian tube during swallowing via a diagnostic probe inserted via the nasopharynx. Since such a diagnostic system may be used dynamically during swallowing, the probe may be made of a flexible and durable material configured to be atraumatic. In one embodiment, the guide catheter(s) 100 used in the nasopharynx approach may be removed once the diagnostic probe is in or near the ET region and prior to the swallowing.

In one embodiment, the diagnostic probe may comprise an endoscope to visualize the ET structure and function. Alternatively, the diagnostic probe may include a pressure transducer located on a catheter or a wire. When a pressure transducer is used, the pressure within the ET may be monitored during swallowing and the pressure measurements may be interpreted for ET opening function. Alternatively, an ultrasound probe may be inserted in the ET lumen to scan the ET region's structure. Fluid may be introduced into the ET to facilitate ultrasound diagnosis. For any of the above diagnostic systems, a single short length transducer that is repositioned after each swallow may be used. Alternatively, an array of transducers may be used to facilitate mapping of all or a portion of an ET.

The techniques described above may be used to directly access and diagnose a Eustachian tube of a patient. In one embodiment, a method for accessing a Eustachian tube of a patient may include inserting a guide catheter into a nasal passage of the patient, the guide catheter having a distal tip with a bend having an angle between about 30 and about 90 degrees; and advancing the guide catheter in the nasal passage toward an opening of the Eustachian tube in the nasopharynx to place the distal tip adjacent the Eustachian tube opening. Additionally, the method may also include advancing a diagnostic device through the guide catheter to place a distal tip of the diagnostic device adjacent the Eustachian tube opening. The diagnostic device may include a diagnostic catheter. The diagnostic device may include an endoscope, a pressure transducer, or an ultrasound catheter.

Additionally, the method may also include introducing a diagnostic probe into the Eustachian tube to directly assess Eustachian tube function. It is preferred that the diagnostic probe is made from a flexible and Eustachian tube compatible material. Alternatively, the diagnostic probe may comprise a pressure transducer located on a guidewire, and whereby the method also includes monitoring pressure within the Eustachian tube while the patient is swallowing; and assessing an opening function of the patient's Eustachian tube using the monitoring. The method may also include removing the guide catheter after the diagnostic probe is placed into the Eustachian tube. Additionally, or alternatively, the diagnostic probe may comprise an ultrasound probe.

For indirect functional diagnosis of a Eustachian tube, in some embodiments, an external energy source may be used to assess opening of the Eustachian tube. For example, possible energy sources may include, but are not limited to, pressure, sound, light or other electromagnetic energy. In one embodiment of indirect assessment, an emitter may be positioned in the nasopharynx and a receiver may be placed at the tympanic membrane. Correlation between the emitted signal and the received signal may be translated into the physical characteristics of the ET during swallowing.

The techniques described above may be used to implement procedures for indirectly accessing and diagnosing the Eustachian tube of a patient. The indirect assessment method includes positioning an energy emitter in the nasopharynx adjacent a Eustachian tube; positioning an energy receiver adjacent the tympanic membrane via the external ear canal; directing energy from the emitter toward the receiver; generating an emitter signal representative of the energy from the emitter; generating a receiver signal representative of the energy received by the emitter; forming a comparison between the emitter signal and the receiver signal; and indirectly assessing function of the Eustachian tube during swallowing, using the comparison. The energy emitter can be a device that emits energy in the form of a pressure wave or electromagnetic energy. The indirect assessment may also include estimating the physical characteristics of Eustachian tube.

Treatment

Figure 8:
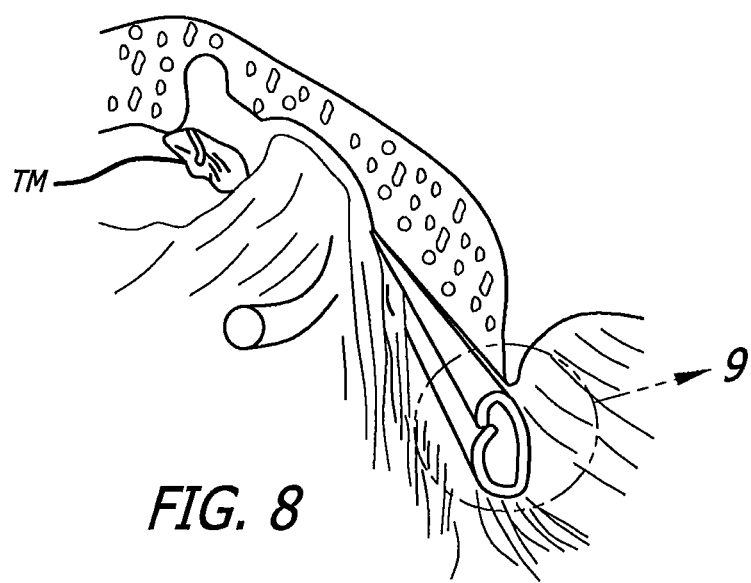
FIG. 8 shows a section of the anatomical region around a Eustachian tube (ET).
Figure 9:
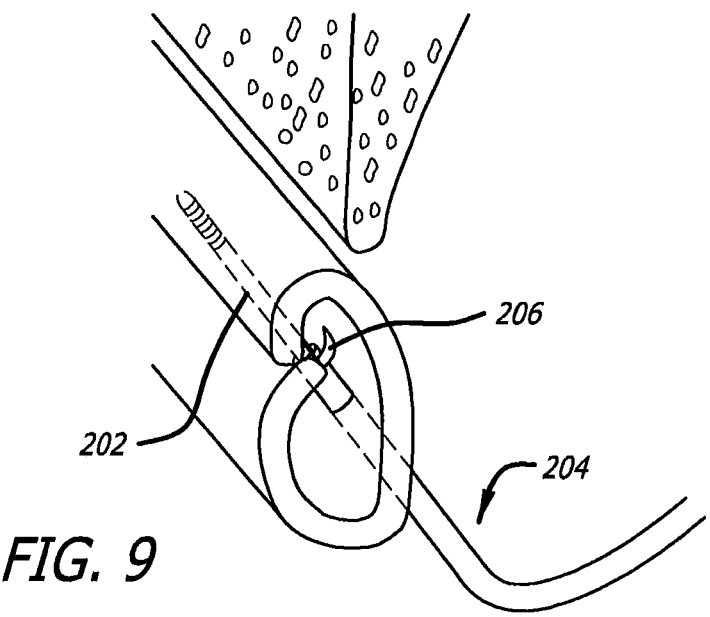
FIG. 9 shows a section of the anatomical region around a Eustachian tube showing a diagnostic or therapeutic procedure to debulk edematous tissue around the ET.
Figure 10:
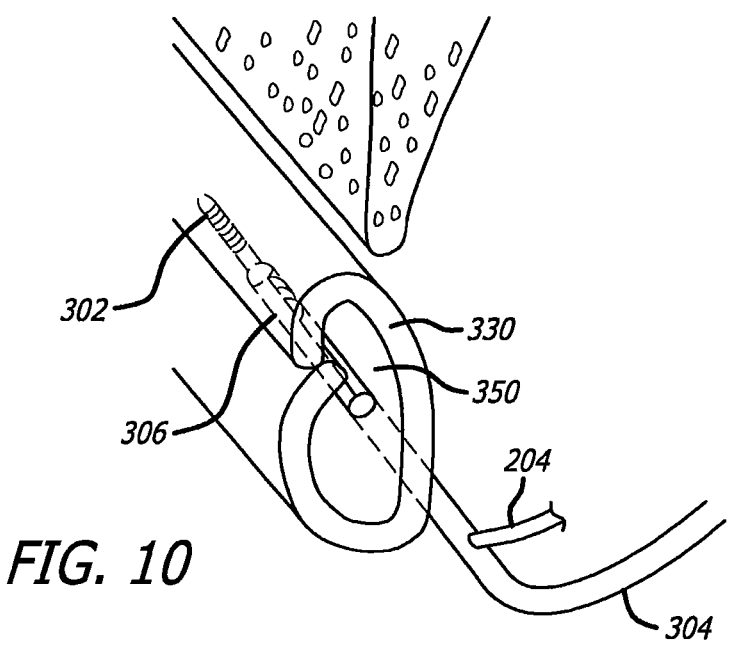
FIG. 10 shows a section of the anatomical region around a Eustachian tube showing an alternative therapeutic procedure to debulk edematous tissue around the ET.

Another embodiment of the present invention is directed toward the treatment of Eustachian tube disorders. In some cases, for example, Eustachian tube disorders may be related to structural obstructions of the Eustachian tube. Structural disorders of the Eustachian tube are often the result of anatomical abnormalities or excessive or edematous tissue in or around the Eustachian tube, as shown in FIG. 8. FIG. 8 shows a section of the anatomical region around a Eustachian tube ET. FIG. 8 shows some general anatomical landmarks including the tympanic membrane TM, the carotid artery, the ET cartilage as well as the location of the tensor villi palatine and the levator villi palatine muscles. FIGS. 9-10 show diagnostic or therapeutic procedures being performed in the region around the ET.

FIG. 9 shows a section of the anatomical region around a Eustachian tube showing a diagnostic or therapeutic procedure to debulk edematous tissue around the ET. The procedure illustrated in FIG. 9 includes accessing the ET lumen using a guidewire 202 and removing tissue from one side of the ET using a debulking tool 204. As shown in FIG. 9, in one embodiment, the debulking tool 204 may have a retractable debulking tip 206 projecting from one side so that the tip removes tissue from one side of the ET lumen. This therapeutic procedure preferably allows for controlled access and positioning within the ET and prevents injury to opposing surfaces. It should be realized that the above-described therapeutic procedures can be performed with the aid of ultrasound guidance or visualization, for example, by using an intra-ET visualization catheter. The ultrasound can be used for diagnosis before therapy as described above. It may also be used for guidance and or assistance during the therapy. In alternative embodiments, the debulking tool 204 may be advanced into a Eustachian tube without using a guidewire and may be advanced either with or without using a guide catheter.

FIG. 10 shows a section of the anatomical region around a Eustachian tube showing an alternative therapeutic procedure to debulk edematous tissue around the ET. In the alternative procedure shown in FIG. 10, the debulking device 304 may be introduced at its tip or distal end 306 submucosally between cartilage 330 and the mucosal surface, so that the mucosal surface is preserved. For this alternative procedure, the guidewire 302 and/or the debulking device may be tracked between the lumen and the cartilage, thereby protecting both the mucosal surface and the carotid artery. As shown in FIG. 10, the guidewire 302 may be inserted at a submucosal entry point between the ET cartilage and the mucosal surface. Subsequently, the debulking tool 304 may be introduced along the guidewire 302 to debulk the tissue region without affecting the mucosal surface. Ultrasound, like low power, high efficiency ultrasounds, can be used as the debulking tool to ablate, shrink or debulk tissues under the mucosal tissue. As with the device described previously, in alternative embodiments, the debulking device 304 may be advanced into a Eustachian tube without using a guidewire and may be advanced either with or without using a guide catheter.

The treatment techniques described above may be used to treat the Eustachian tube of a patient by placing a guidewire into a Eustachian tube of the patient via the patient's nasopharynx; introducing a debulking device along the guidewire into the Eustachian tube of the patient; and removing edematous tissue including hypertropic mucosa from a surface along one side of the Eustachian tube. The guidewire may include markings for providing feedback related to the introducing into the Eustachian tube. Alternatively, the debulking tool can be introduced into the ET without first placing a guidewire therein. In either case (i.e., with or without a guidewire), in some embodiments the treatment devices may be advanced into the Eustachian tube via a guide catheter, while in alternative embodiments the treatment device may be advanced without use of a guide catheter. In fact, any of the treatment devices described herein may be used with or without a guidewire and with or without a guide catheter, in various alternative embodiments of the devices.

Alternatively, a method for treating a Eustachian tube in a patient may include introducing via the patient's nasopharynx a guidewire submucosally between cartilage and a mucosal surface of a Eustachian tube; introducing a debulking device along the guidewire into submucosal tissue of the Eustachian tube, between the cartilage and the mucosal surface; and removing some of the submucosal tissue.

In addition to the therapeutic procedures described above and illustrated in FIGS. 9-10, tissue removal or remodeling (e.g. shrinkage) may be accomplished using mechanical, laser, radio frequency, and/or chemical therapies. For example, in cases where muscular dysfunction or anatomical disorder is a contributing factor, the muscles (tensor villi palatine or levator villi palatine) may be shortened or tensioned. One method of accomplishing or shortening the muscles is to create a lesion in the muscles. Over time the lesion is absorbed and the muscle tightens due to the resorbed muscular mass in a manner similar to somnoplasty.

Another embodiment of the present invention is directed toward the treatment of Eustachian tube disorders caused by inflammation or edema. In addition to the surgical procedures described above, edema may also be reduced through pharmaceutical therapy. Delivery of therapeutic agents, especially steroids, into the ET mucosa may be facilitated locally using a range of methods including aspirating directly into the ET using a micro-catheter designed to enter either the nasopharynx or the middle ear side of the ET. Alternatively, an agent may be delivered from the surface of a dilation balloon. In this case, the agent may be deposited into the mucosal layer rather than onto its surface. Sustained delivery may be facilitated by depositing the drug into a reservoir and embedding the reservoir into the mucosa. Extending the residence time of therapeutic agents may be achieved by including the agents as particles and charging the reservoir particles such that they adhere to the mucosa surface. Alternatively, the residence time of therapeutic agents may be controlled by implanting the reservoir into the ET or its substructure.

Figure 11:
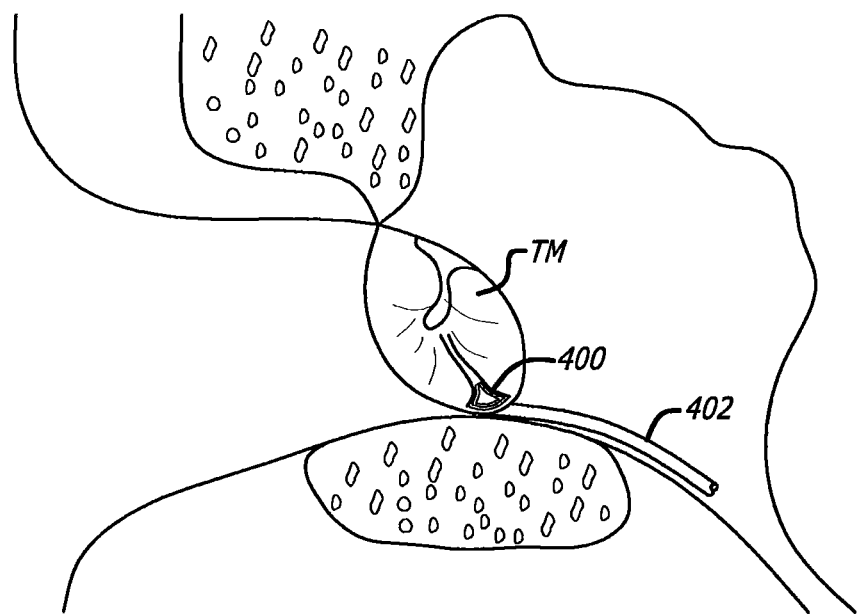
FIG. 11 shows an exemplary drug delivery system for delivering a pharmaceutical agent to treat ET inflammation or edema.

An exemplary drug delivery system according to one embodiment is shown in FIG. 11. As shown in FIG. 11, a pressure equalization tube 400 may be inserted into the tympanic membrane. The pressure equalization tube includes an extension 402 that resides in the region of the Eustachian tube, where the extension has drug delivery capabilities. As shown on FIG. 11, the pressure equalization tube 400 may be dual-lumen to provide drug delivery and ventilation functions. The pressure equalization tube 400 having an extension 402 may be designed to slide between the radial fibers of the tympanic membrane TM. When in place the tube may be oriented to minimize migration paths.

Figure 12:
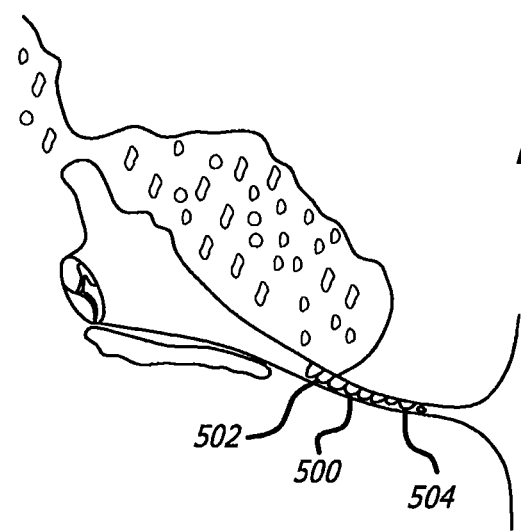
FIG. 12 shows an alternative drug delivery system for delivering a pharmaceutical agent to treat ET inflammation or edema that may be provided through the nasopharynx.

Alternatively, a drug delivery system may be provided through the nasopharynx as illustrated in FIG. 12. As shown in FIG. 12, the drug delivery may be provided from an intraluminal temporary implant 500. The temporary nature of the implant 500 may require a removal system or may provide for natural removal through degradation and/or digestion. Similar to the debulking devices described above, the drug delivery system may also be implanted submucosally, thus having the benefit of not obstructing the surface mucosa. In one embodiment, the implant may be deployed into the posterior cushion of the ET between the lumen and the cartilage. This method may benefit from the use of consistent anatomical landmarks and may minimize the likelihood of trauma to the middle ear or carotid artery. The implant 500 may include an anchored drug delivery reservoir in the form of a coil having a reducing diameter distal 502 to proximal 504, respectively.

Figure 13:
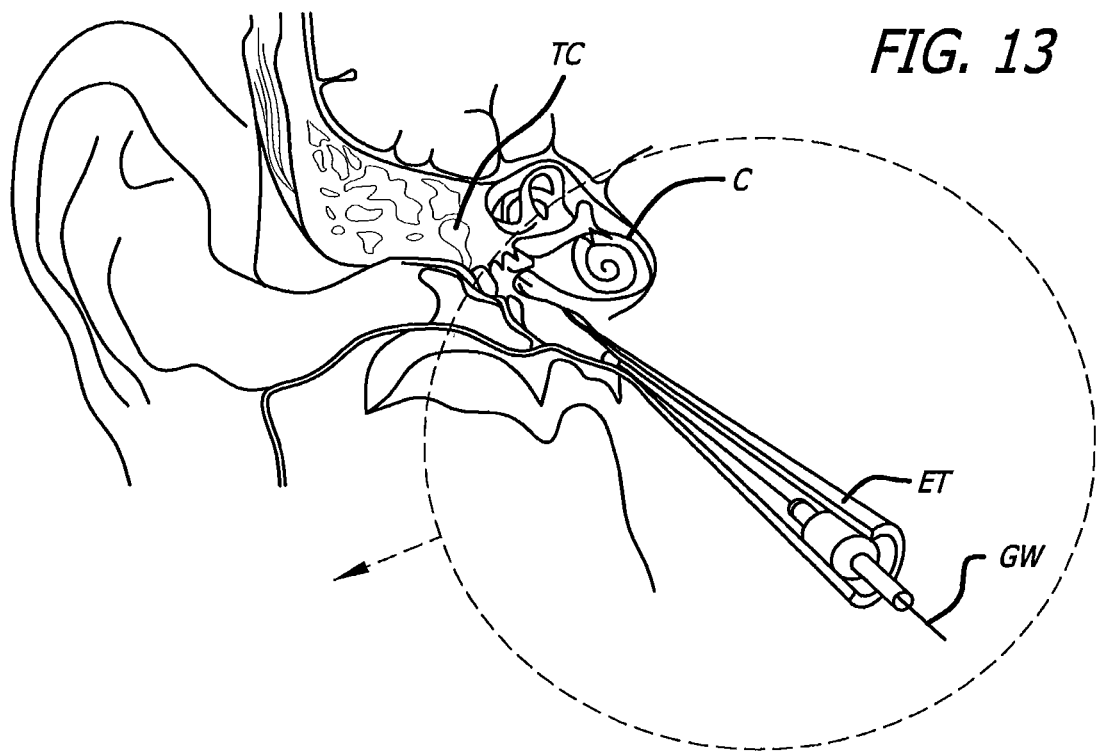
FIG. 13 shows a section of the anatomical region around the ET showing a diagnostic or therapeutic procedure being performed by devices inserted through the pharyngeal ostium of the Eustachian tube.

FIG. 13 shows a section of the anatomical region around a Eustachian tube ET showing a diagnostic or therapeutic procedure being performed by devices inserted through the pharyngeal ostium of the Eustachian tube. FIG. 13 shows a guidewire GW inserted into a desired region in the ET through the nasopharynx and a diagnostic or therapeutic procedure being performed by a device introduced into the Eustachian tube over guidewire GW.

Figure 13A:
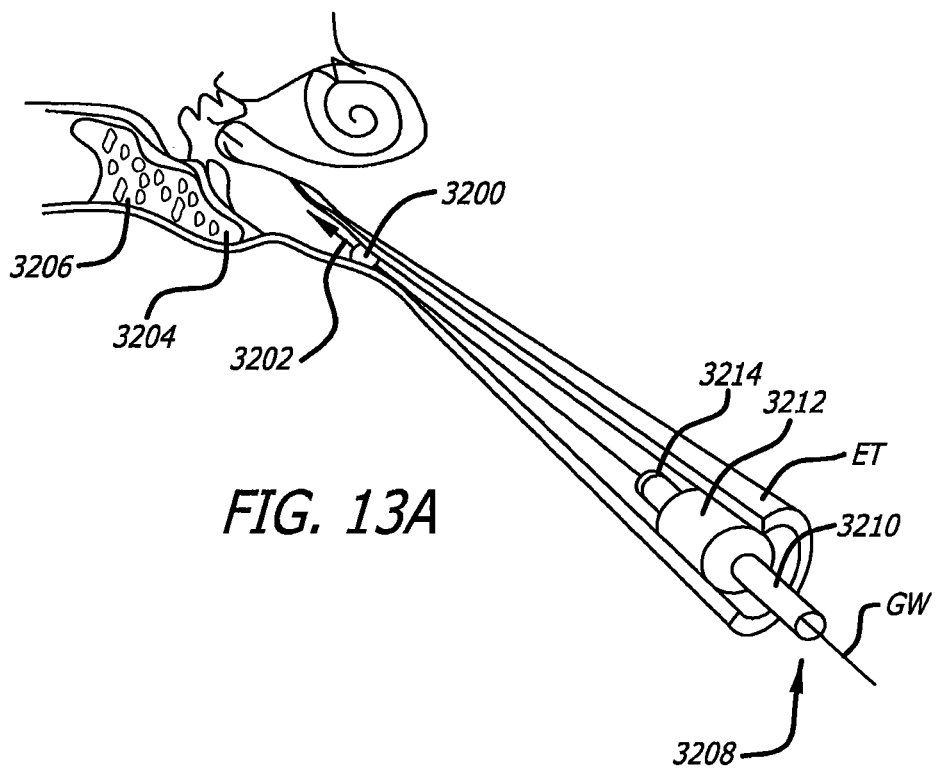
FIG. 13A shows an enlarged view of the region encircled by a broken line in FIG. 13.

FIG. 13A shows an enlarged view of region 33A in FIG. 13, showing the anatomical region around a Eustachian tube ET, and showing a diagnostic or therapeutic procedure being performed by devices inserted through the pharyngeal ostium of the Eustachian tube. In one embodiment, guidewire GW comprises an anchoring balloon 3200 located on the distal region of guidewire GW. Anchoring balloon 3200 is inflated after positioning guidewire GW at a target location. Anchoring balloon 3200 anchors guidewire GW to the adjacent anatomy and prevents accidental repositioning of guidewire GW during a diagnostic or therapeutic procedure. Anchoring balloon 3200 may be made from any suitable compliant or semi-compliant material, such as but not limited to crosslinked polyethylene or other polyolefins, polyurethane, flexible polyvinylchloride, Nylon, or the like. In various alternative embodiments, guidewire GW may include one or more anchoring elements other than anchoring balloon 3200, such as a notch on guidewire GW, a bent region on guidewire GW, a self-expanding element, a hook, a coiled element, or the like. In another embodiment, guidewire GW may include a sensor 3202 located on the distal region of guidewire GW. Sensor 3202 may enable guidewire GW to be used in conjunction with a suitable surgical navigation system. In one embodiment, sensor 3202 may include an electromagnetic sensor used in conjunction with an electromagnetic surgical navigation system such as GE InstaTrak™3 500 plus system. One or more sensor 3202 or other types of surgical navigation sensors or transmitters may also be located on other diagnostic or therapeutic devices disclosed herein. Sensor 3202 may be used in conjunction with a stationary sensor 3204 located in the external ear. The combination of sensor 3202 and stationary sensor 3204 may facilitate positioning of guidewire GW in a target region.

In some embodiments, the guidewire GW may include one or more stop members (not pictured), either at its distal end, its proximal end, or both. Such stop members may be in addition to the anchoring balloon 3200 or may be included in embodiments that do not have an anchoring balloon 3200. The stop members help prevent the distal end of guidewire GW from being passed too far into the Eustachian tube and thus help prevent any damage to structures that might result from advancing guidewire GW too far. In one embodiment, for example, guidewire GW may include a distal curve or bend that prevents it from passing through a narrow portion of the Eustachian tube. This or another embodiment may also include a proximal stop member that abuts against a proximal portion of a guide catheter through which to the guidewire is passed, thus preventing it from passing too far. In any of the above described embodiments, the guidewire may also have an atraumatic tip.

In another embodiment, a radiopaque plug 3206 may be inserted from the external ear to a region adjacent to an eardrum. Radiopaque plug 3206 may serve as a fiducial marker during preoperative scanning of the patient and thus may enable a physician to accurately position a diagnostic or therapeutic device close to the eardrum. Other image guidance methods and devices may also be used in conjunction with diagnostic or therapeutic procedures disclosed herein. FIG. 13A also shows a diagnostic or therapeutic device 3208 comprising a shaft 3210 and a working element 3212, e.g. a dilating balloon being introduced over guidewire GW. Diagnostic or therapeutic device 3208 may comprise a radiopaque marker 3214.

Figure 13B:
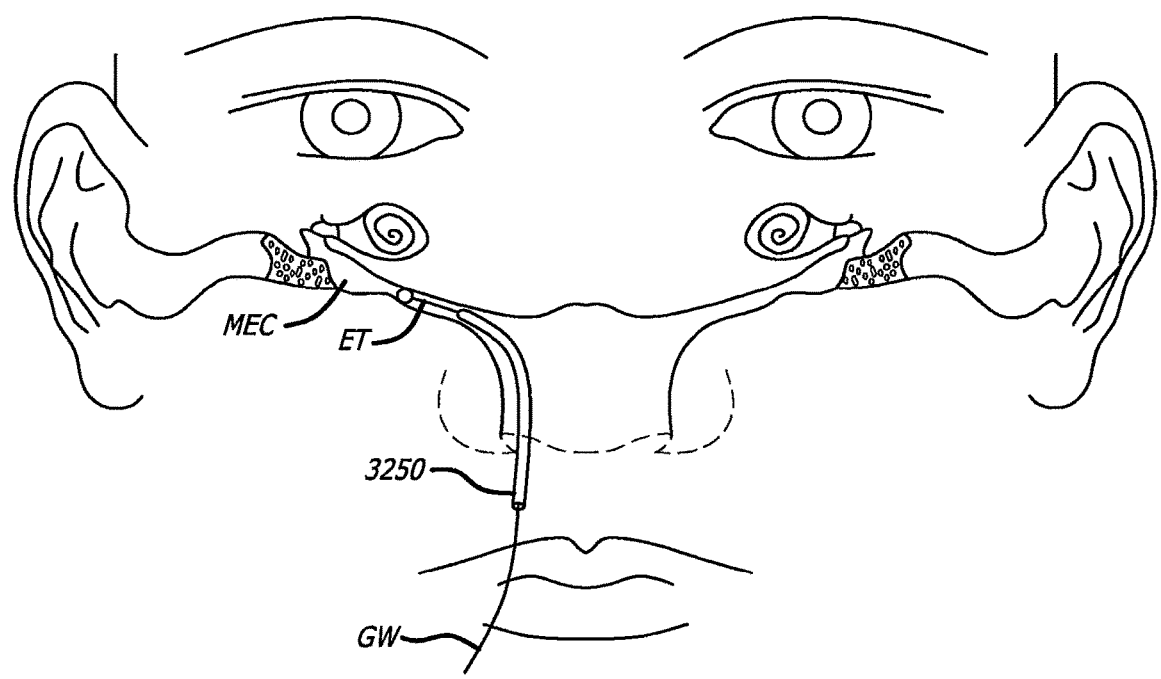
FIG. 13B shows a front view of a human head with a portion of the face removed to show an embodiment of a method of introducing a guidewire into a Eustachian tube.

FIG. 13B shows a front view of a human head with a portion of the face removed to show an embodiment of a method of introducing a guidewire GW into a Eustachian tube. In FIG. 13B, a guide catheter 3250 is introduced through a nostril into the nasopharynx. A distal portion of guide catheter 3250 may comprise a bent or angled region. For example, in one embodiment such bent or angled region may form an internal angle ranging from about 45 degrees to about 150 degrees. Guide catheter 3250 may be constructed using one of the various designs disclosed in the assignee's patent application Ser. No. 11/926,565, issued as U.S. Pat. No. 8,961,495 on Feb. 24, 2015, which is hereby incorporated herein by reference. Guide catheter 3250 is positioned in the nasopharynx such that the distal tip of guide catheter 3250 is located near a nasopharyngeal opening of a Eustachian tube. Thereafter, a guidewire GW is introduced through guide catheter 3250 into the Eustachian tube. Guidewire GW can then be used to advance one or more diagnostic or therapeutic devices into the Eustachian tube to perform one or more diagnostic or therapeutic procedures.

Figure 14A:
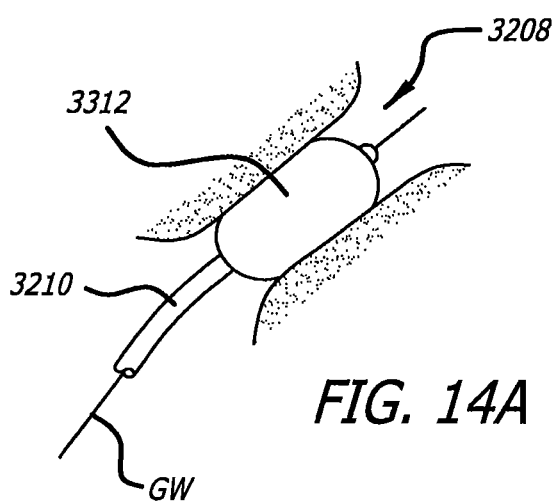
FIGS. 14A-14D illustrate various examples of working elements that could be located on the diagnostic or therapeutic device in FIG. 13.

FIGS. 14A-14D illustrate various embodiments of working elements that may be located on a diagnostic or therapeutic device such as a catheter 3210, which may in some embodiments be advanced over a guidewire 3208. FIG. 14A shows a balloon dilation catheter 3210 having a working element comprising a dilating balloon 3312, advanced over a guidewire 3208. The dilating balloon 3312 may be made from a suitable non-compliant material, such as but not limited to polyethylene terephthalate, Nylon, or the like. In various alternative embodiments, the balloon catheter 3210 may be advanced over the guidewire 3208 without the use of a guide catheter, over or through a guide catheter without the use of the guidewire 3208, over the guidewire 3208 and through a guide catheter, or by itself without using the guidewire 3208 or guide catheter (such as with a partially rigid balloon catheter). Also in various embodiments, the balloon catheter 3210 may include multiple lumens for inflation/deflation of the balloon 3312, irrigation and/or suction, drug delivery, passage of a visualization device such as a flexible endoscope, or any suitable combination thereof.

Figure 14B:
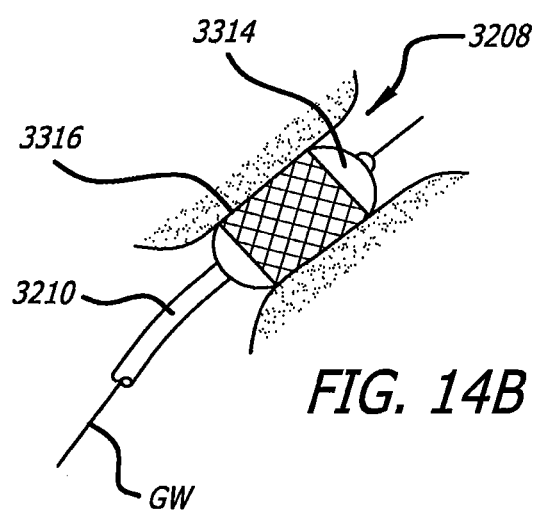

FIG. 14B shows an example of a working element comprising a dilating balloon 3314 loaded with a balloon-expandable stent 3316. In some embodiments, dilating balloon 3314 may be made from a suitable non-compliant material, such as but not limited to polyethylene terephthalate, Nylon, or the like. Several types of stent designs may be used to construct stent 3316, such as but not limited to metallic tube designs, polymeric tube designs, chain-linked designs, spiral designs, rolled sheet designs, single wire designs, or the like. These designs may have an open-cell or closed-cell structure. A variety of fabrication methods may be used for fabricating stent 3316, including but not limited to laser cutting a metal or polymer element, welding metal elements, etc. A variety of materials may be used for fabricating stent 3316, including but not limited to metals, polymers, foam type materials, plastically deformable materials, super elastic materials, and the like. A variety of features may be added to stent 3316, including but not limited to radiopaque coatings, drug elution mechanisms to elute anti-inflammatory agents, antibiotics, and the like. In one embodiment, stent 3316 may be bioabsorbable. Working elements may also comprise a self-expanding stent instead of a pressure-expandable stent.

Figure 14C:
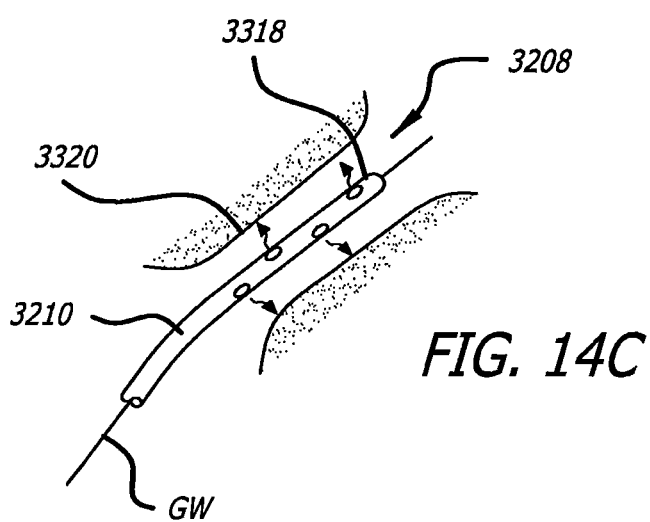

FIG. 14C shows an alternative embodiment comprising a lavage catheter 3210 with a working element comprising a lavage element 3318. Lavage element 3318 may include multiple lavage openings 3320. Lavage openings 3320 may be connected to a lavage lumen in the shaft of the catheter 3210, through which suitable lavage media such as solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like may be delivered. In one embodiment, a fraction of lavage openings 3320 may be connected to an aspiration lumen to aspirate the lavage media out of the Eustachian tube.

Figure 14D:
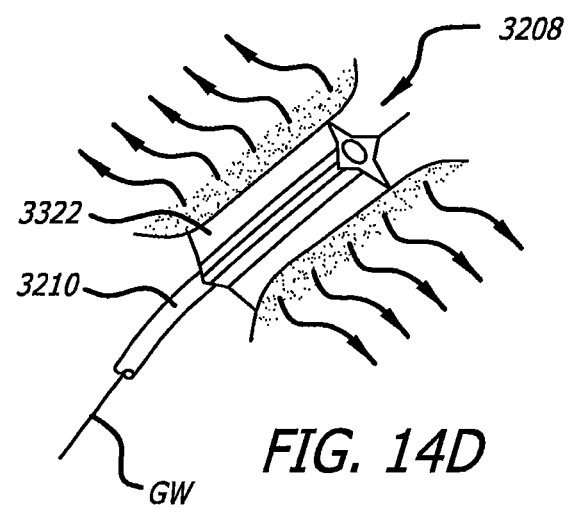

FIG. 14D shows an example of a working element comprising a substance delivery reservoir 3322. Substance delivery reservoir 3322 may be fully or partially biodegradable or non-biodegradable. In one embodiment, substance delivery reservoir 3322 is made of a suitable biocompatible material such as hydrogel (e.g. collage hydrogel). In another embodiment, substance delivery reservoir 3322 comprises a porous matrix formed of a porous material such as a flexible or rigid polymer foam, cotton wadding, gauze, etc. Examples of biodegradable polymers that may be foamed or otherwise rendered porous include polyglycolide, poly-L-lactide, poly-Dlactide, poly(amino acids), polydioxanone, polycaprolactone, polygluconate, polylactic acid-polyethylene oxide copolymers, modified cellulose, collagen, polyorlhoesters, polyhydroxybutyrate, polyanhydride, polyphosphoester, poly(alpha-hydroxy acid) and combinations thereof. Examples of nonbiodegradable polymers that may be foamed or otherwise rendered porous include polyurethane, polycarbonate, silicone elastomers, etc. Substance delivery reservoir 3322 may also include one or more embodiments disclosed in U.S. patent application Ser. No. 10/912,578 entitled "Implantable Device and Methods for Delivering Drugs and Other Substances to Treat Sinusitis and Other Disorders" filed on Aug. 4, 2004, issued as U.S. Pat. No. 7,361,168 on Apr. 22, 2008, the entire disclosure of which is expressly incorporated herein by reference. The substance delivery reservoir 3322 or any substance delivery devices described in this application may be used to deliver various types of therapeutic or diagnostic agents. The term "diagnostic or therapeutic substance" as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or non-fluid. For example, in some applications where it is desired to treat or prevent a microbial infection, the substance delivered may comprise pharmaceutically acceptable salt or dosage form of an antimicrobial agent (e.g. antibiotic, antiviral, antiparacytic, antifungal, etc.), a corticosteroid or other anti-inflammatory (e.g. an NSAID), a decongestant (e.g. vasoconstrictor), a mucous thinning agent (e.g. an expectorant or mucolytic), an agent that prevents or modifies an allergic response (e.g. an antihistamine, cytokine inhibitor, leucotriene inhibitor, IgE inhibitor), etc.

Some nonlimiting examples of antimicrobial agents that may be used in this invention include acyclovir, amantadine, aminoglycosides (e.g. amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenemlcilastatin, isoniazid, itraconazole, ketoconazole, metronidazole, nafcillin, nafcillin, nystatin, penicillin, penicillin G, pentamidine, piperacillinitazobactam, rifampin, quinupristin-dalfopristin, ticarcillinlclavulanate, trimethoprimlsulfamethoxazole, valacyclovir, vancomycin, mafenide, silver sulfadiazine, mupirocin (e.g. Bactroban, Glaxo SmithKline, Research Triangle Park, N.C.), nystatin, triarncinolonelnystatin, clotrimazolelbetamethasone, clotrimazole, ketoconazole, butoconazole, miconazole, tioconazole; detergent-like chemicals that disrupt or disable microbes (e.g. nonoxynol-9, octoxynol-9, benzalkonium chloride, menfegol, and N-docasanol); chemicals that block microbial attachment to target cells and/or inhibit entry of infectious pathogens (e.g. sulphated and sulphonated polymers such as PC-515 (carrageenan), Pro-2000, and Dextrin 2 Sulphate); antiretroviral agents (e.g. PMPA gel) that prevent retroviruses from replicating in the cells; genetically engineered or naturally occurring antibodies that combat pathogens such as anti-viral antibodies genetically engineered from plants known as "plantibodies"; agents which change the condition of the tissue to make it hostile to the pathogen (such as substances which alter mucosal pH (e.g. Buffer Gel and Acid form)); non-pathogenic or "friendly" microbes that cause the production of hydrogen peroxide or other substances that kill or inhibit the growth of pathogenic microbes (e.g. *lactobacillus*); antimicrobial proteins or peptides such as those described in U.S. Pat. No. 6,716,813 (Lim et al.), which is expressly incorporated herein by reference, or antimicrobial metals (e.g. colloidal silver).

Additionally or alternatively, in some applications where it is desired to treat or prevent inflammation the substances delivered in this invention may include various steroids or other anti-inflammatory agents (e.g. nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate, amcinonide, desoximetasone, diflorasone, fluocinolone, fluocinonide, halcinonide, clobetasol, augmented betamethasone, diflorasone, halobetasol, prednisone, dexarnethasone and methylprednisolone. Other anti-inflammatory, analgesic or antipyretic agents that may be used include the Nonselective COX Inhibitors (e.g. salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g. diaryl-substituted furanones such as rofecoxib; diaryl-substituted pyrazoles such as celecoxib; indole acetic acids such as etodolac; and sulfonanilides such as nimesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor; and d) SYK Kinase inhibitors such as an agent designated as "R-112" manufactured by Rigel Pharmaceuticals, Inc., South San Francisco, Calif.

Additionally or alternatively, in some applications, such as those where it is desired to shrink mucosal tissue, cause decongestion, or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine. In one particular embodiment, the substance delivered by this invention comprises a combination of an anti-inflammatory agent (e.g. a steroid or an NSAID) and a mucolytic agent.

Additionally or alternatively, in some applications such as those where it is desired to prevent or deter histamine release, the substances delivered in this invention may include various mast cell stabilizers or drugs which prevent the release of histamine such as crornolyn (e.g. Nasal Chroma) and nedocromil.

Additionally or alternatively, in some applications such as those where it is desired to prevent or inhibit the effect of histamine, the substances delivered in this invention may include various antihistamines such as azelastine (e.g. Astylin) diphenhydramine, loratidine, etc.

Additionally or alternatively, in some embodiments such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsin1EDTA, hyaluronidase, and tosyllysylchloromethane (TLCM).

Additionally or alternatively, in some applications, the substances delivered in this invention may include other classes of substances that are used to treat rhinitis, nasal polyps, nasal inflammation, and other disorders of the ear, nose and throat including but not limited to anti-cholinergic agents that tend to dry up nasal secretions such as ipratropium (Atrovent Nasal®), as well as other agents not listed here.

Additionally or alternatively, in some applications such as those where it is desired to draw fluid from polyps or edematous tissue, the substances delivered in this invention may include locally or topically acting diuretics such as furosemide and/or hyperosmolar agents such as sodium chloride gel or other salt preparations that draw water from tissue or substances that directly or indirectly change the osmolar content of the mucous to cause more water to exit the tissue to shrink the polyps directly at their site.

Additionally or alternatively, in some applications such as those wherein it is desired to treat a tumor or cancerous lesion, the substances delivered in this invention may include antitumor agents (e.g. cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g. cyclophosphamide, isophosphamide), nitrosoureas or other agents which kill cancer cells by inhibiting changes necessary for cellular DNA repair (e.g. carmustine (BCNU) and lomustine (CCNU)), antimetabolites and other agents that block cancer cell growth by interfering with certain cell functions, usually DNA synthesis (e.g. 6 mercaptopurine and 5-fluorouracil (5FU), antitumor antibiotics and other compounds that act by binding or intercalating DNA and preventing RNA synthesis (e.g. doxorubicin, daunorubicin, epirubicin, idarubicin, mitomycin-C and bleomycin) plant (*vinca*) alkaloids and other antitumor agents derived from plants (e.g. vincristine and vinblastine), steroid hormones, hormone inhibitors, hormone receptor antagonists and other agents which affect the growth of hormone-responsive cancers (e.g. tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g. meth-I, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, 1M862, TNP-470, celecoxib (Celebrex), rofecoxib (Vioxx), interferon alpha, interleukin-12 (IL-12) or any of the compounds identified in St. Croix et al., "Genes Expressed in Human Tumor Endothelium," Science Vol. 289, pages 1197-1201 (Aug. 17, 2000), which is expressly incorporated herein by reference, biological response modifiers (e.g. interferon, *bacillus* calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles such as plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

Additionally or alternatively to being combined with a device and/or a substance releasing modality, it may be ideal to position the device in a specific location upstream in the mucous flow path (i.e. frontal sinus or ethmoid cells). This could allow the deposition of fewer drug releasing devices, and permit the "bathing" of all the downstream tissues with the desired drug. This utilization of mucous as a carrier for the drug may be ideal, especially since the concentrations for the drug may be highest in regions where the mucous is retained; whereas non-diseased regions with good mucous flow will be less affected by the drug. This could be particularly useful in chronic sinusitis, or tumors where bringing the concentration of drug higher at those specific sites may have greater therapeutic benefit. In all such cases, local delivery will permit these drugs to have much less systemic impact. Further, it may be ideal to configure the composition of the drug or delivery system such that it maintains a loose affinity to the mucous, permitting it to distribute evenly in the flow. Also, in some applications, rather than a drug, a solute such as a salt or other mucous soluble material may be positioned at a location whereby mucous will contact the substance and a quantity of the substance will become dissolved in the mucous thereby changing some property (e.g. pH, osmolarity, etc.) of the mucous. In some cases, this technique may be used to render the mucous hyperosmolar so that the flowing mucous will draw water and/or other fluid from polyps, edematous mucosal tissue, etc., thereby providing a drying or desiccating therapeutic effect.

The above-described treatments of the Eustachian tube of a patient allow for advancing a treatment device through the guide catheter toward the Eustachian tube to place a distal tip of the treatment device adjacent the Eustachian tube opening. It may be preferred for the treatment device to have distal radiopaque member. The treatment device may include a catheter.

Alternatively or in addition, the treatment device can include a fluid introduction device for introducing a fluid into a middle ear space of the patient's ear. The fluid may be air, a contrast medium, an aspiration fluid, or a drug such as those described above. The treatment method can also include scanning the middle ear space using an ultrasound device. Alternatively, or in addition, the treatment device can include an aspiration device for aspirating a substance from the middle ear space.

Alternatively or in addition, the treatment may also include introducing a protective device proximal the Eustachian tube, and monitoring advancement of the treatment device using the protective device. The protective device may be a sensor positioned proximal the tympanic membrane to sense the position of the treatment device during the advancement. Alternatively, the protective device may comprise an endoscope to visualize the advancement.

Alternatively, or in addition, the method for treating a Eustachian tube in a patient includes placing a dual lumen pressure equalization tube through the tympanic membrane of the patient, the tube having a distal extension for location in a region of the Eustachian tube; providing a medication to the region of the Eustachian tube through a first lumen of the dual lumen tube in fluid communication with the distal extension; and providing ventilation across the tympanic membrane through a second lumen of the dual lumen tube. The medication is used to reduce edema in the Eustachian tube region.

The medication may also include surfactant configured to modify a surface tension of a mucosal layer of the Eustachian tube to effect an enhanced wetting of the mucosal surface with the medication. The medication may also include particles that are used for capturing by mucosal tissue of the Eustachian tube to effect an extended release of the medication. Exemplary surfactants are disclosed in U.S. Pat. No. 6,616,913, entitled "Composition and Method for Treatment of Otitis Media", the disclosure of which is incorporated herein by reference.

In another embodiment, the present invention is directed to an apparatus for treating a Eustachian tube in a patient. The apparatus includes a dual lumen tube for insertion into a tympanic membrane of the patient's ear. The tube can include a distal extension for placement in a region of the Eustachian tube, a first lumen for providing a medication to the region of the Eustachian tube through the distal extension, and a second lumen for providing ventilation across the tympanic membrane.

The first lumen may be disposed within the second lumen. Alternatively, the second lumen is disposed within the first lumen. Additionally or alternatively, the first lumen is disposed adjacent the second lumen. The dual lumen tube may be made from or it may include a biodegradable bioresorbable material.

In another embodiment, the present invention is directed to the treatment of the Eustachian tube by delivering a drug to the Eustachian tube. The method comprises accessing a Eustachian tube region via the nasopharynx, using a guide having a lumen; introducing a guidewire through the lumen of the guide to position it submucosally between cartilage and a mucosal surface of the Eustachian tube; passing a temporary intraluminal implant having a drug delivery reservoir along the guidewire to position the implant submucosally in a posterior cushion of the Eustachian tube region between the lumen and the cartilage; and delivering a drug to the Eustachian tube region from the drug delivery reservoir.

In addition, the method may also include contemporaneously delivering a drug to adenoids and the Eustachian tube region from the drug delivery reservoir. In one embodiment, the drug delivery reservoir can comprise a coating layer disposed on the implant. In another embodiment, the guide comprises a biodegradable bioresorbable material.

In another embodiment, the treatment of the Eustachian tube in a patient includes obtaining access to a Eustachian tube region via the nasopharynx, introducing via the patient's nasopharynx a hollow guidewire dimensioned to reach into the Eustachian tube region, the hollow guidewire comprising a plurality of apertures disposed at or near its distal end, and delivering a drug to at least one of the Eustachian tube or a middle ear region of the patient's ear through the apertures.

In another embodiment, drug may be delivered to tissue in the Eustachian tube via iontophoresis. In this embodiment, a drug fluid may be passed into the Eustachian tube, and an electrical current may be applied to the fluid to drive ions of the drug across a tissue, such as mucous membrane or a tympanic membrane.

In another embodiment, the present invention is directed toward a system for accessing a Eustachian tube of a patient. The system can include a guide configured for passing into a nasal passage of the patient to position a distal tip of the catheter at or near a Eustachian tube, the guide having a distal tip with a bend having an angle between 30 and 90 degrees; and a guidewire configured to pass through the guide into the Eustachian tube.

In one embodiment, the guide comprises a catheter. In another embodiment, the guide comprises a dual lumen tube. In another embodiment, the system may also include a diagnostic device configured for passage through the guide. In another embodiment, the system may also include a treatment device configured for passage through the guide.

Non-Guidewire Devices

Figure 15A:
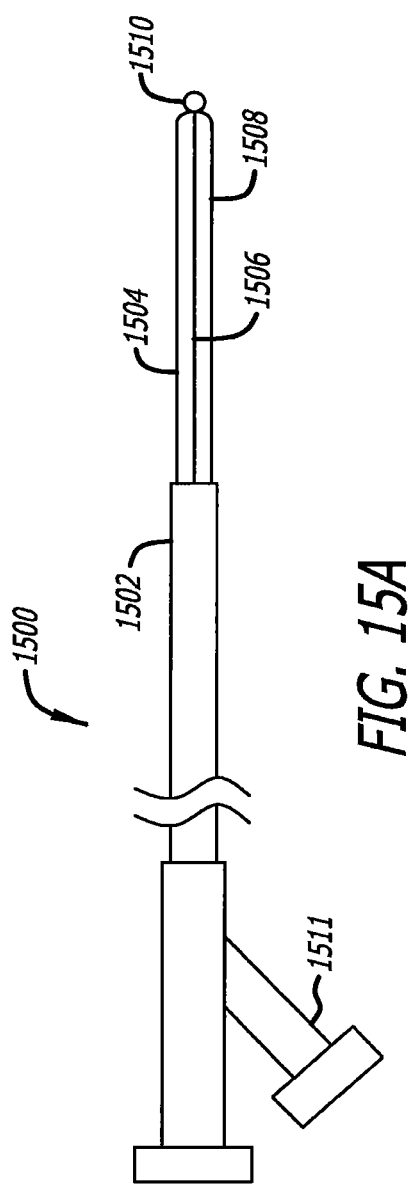
FIGS. 15A and 15B show side views of example devices for providing a therapy to a Eustachian tube.

FIG. 15A shows a device 1500 for treating a Eustachian tube, according to one embodiment. The device 1500 includes an elongate rigid shaft 1502. The rigid shaft may be constructed from a semi-flexible metal or plastic. "Rigid" as used with regards to device 1500 means that the shaft 1502 will not deform when inserting the shaft 1502 into a nasal cavity. The rigid shaft 1502 may be formed from a malleable material and custom bent for use in the field. A therapeutic device, which in this example is an elongate flexible insert 1504, is coupled to the distal portion of the rigid shaft 1502. A stop may be placed at the insert 1504/shaft 1502 junction to prevent the shaft from entering a Eustachian tube. The insert 1504 preferentially includes a lateral stiffness such that when inserted into a Eustachian tube, the insert 1504 will conform to the pathway of the Eustachian tube and not cause significant deformation of the Eustachian tube. The insert 1504 may also include a preformed shape (not shown), for example which is preformed to the anatomy of a Eustachian tube. The insert 1504 preferentially includes a column stiffness strong enough to insert into a Eustachian tube without collapsing on itself or buckling. This example of an insert 1504 includes a core wire 1506 and an expandable balloon 1508. The core wire 1506 may be constructed from metal, such as stainless steel, or a super-elastic alloy such as nickel-titanium. Core wire 1508 diameters in the range of 0.05-0.25 mm may be suitable. The balloon 1508 may be of compliant, semi-compliant, or non-compliant construction. The balloon 1508 may include a preformed shape which matches the profile of a Eustachian tube. The balloon 1508 may include micropores for delivery, upon partial or full expansion, of any of the therapeutic substances disclosed herein. The balloon 1508 may include a coating for delivery of any of the therapeutic substances disclosed herein. The device 1500 may include an atraumatic tip 1510 in the shape of a ball, which may be integral to the core wire 1506. The device 1500 may include a fitting 1511 at the proximal portion of the shaft 1502 for supplying fluid, energy and electrical signals to the insert 1504. The device 1500 may accordingly include a lumen for passage of fluids. The device 1500 does not require a guidewire for insertion into a Eustachian tube, however a guidewire may be optionally used.

The device 1500 may be manually inserted by grasping the shaft 1502 and guiding the insert into a nasal passage and nasopharynx, and into the Eustachian tube, by way of a scope, fluoroscopy, or transillumination. Accordingly, portions of the device 1500 may include radiopaque coatings or materials. The insert 1504 may include fiber optics for transmitting light for transillumination. Examples of transilluminating devices are shown in co-assigned U.S. patent application Ser. No. 10/829,917, issued as U.S. Pat. No. 7,654,997 on Feb. 2, 2010, and Ser. No. 11/522,497, issued as U.S. Pat. No. 7,559,925 on Jul. 14, 2009, both of which are herein incorporated by reference in their entireties. The insert 1504 may also include a CCD or CMOS camera and associated wiring for endoscopic viewing without a separate scope. The device 1500 may also be linked to a 3-D tracking system.

The insert 1504 shown is merely an example and may include other constructions, such as a bare wire. The bare wire may deliver energy, for example resistive heat, ultrasonic, or electrosurgical energy (e.g. RF). Energy may also be delivered by the balloon 1504, for example by a hot fluid or gas.

The insert 1504 may also deliver a stent for supporting or expanding the Eustachian tube. The stent may include a polymer material, which may elute any of the therapeutic substances disclosed herein.

The insert 1504 may also be detachable from the shaft 1504 for delivery into the Eustachian tube. In one example, the insert 1504 may be constructed from a biodegradable polymer, such as polylactic acid, which may also include any of the therapeutic substances disclosed herein. The insert 1504 may then degrade over time and deliver a therapeutic substance as required. The biodegradable insert 1504 may also include a lumen for drainage of fluid in the Eustachian tube.

Figure 15B:
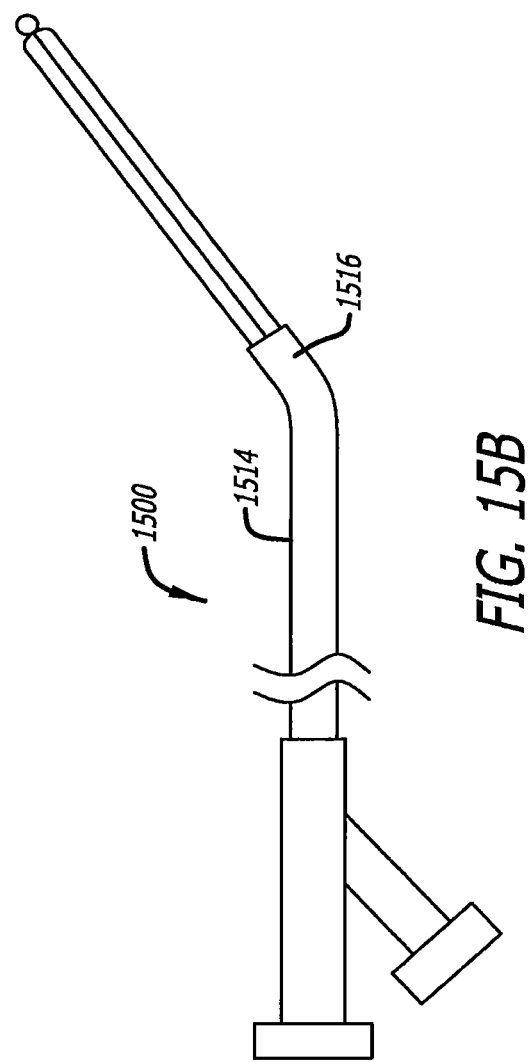

FIG. 15B shows an alternative device 1512 for treating a Eustachian tube, according to one embodiment. The device 1512 is largely constructed as shown in FIG. 15A, however this embodiment includes a rigid shaft 1514 which includes a preferential bend 1516. The bend 1516 may range from 30 to 90 degrees. The bend 1516 allows for easier access to the Eustachian tube in certain anatomies.

Figure 15C:
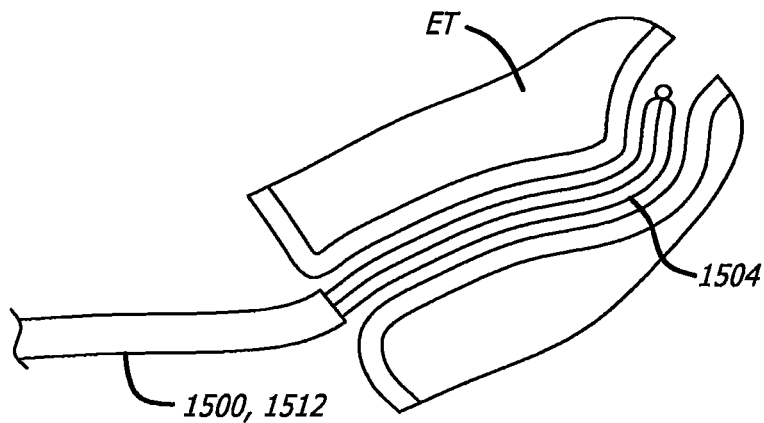
FIGS. 15C-15E show cross-sectional views of example devices providing therapies to a Eustachian tube.

FIG. 15C shows the device 1500 or 1512 in use, according to one embodiment. The device 1500 is shown with the insert 1504 placed within a Eustachian tube ET. The insert 1504 preferentially deforms to match the profile of the Eustachian tube ET, and thus may deliver a therapy without deforming or damaging the Eustachian tube ET. Alternatively, the insert 1504 is preformed to match the profile of the Eustachian tube and deforms slightly while being positioned. The insert 1504 also includes a column stiffness which is significant enough to prevent buckling of the insert during insertion into the Eustachian tube ET, and thus prevent damage to the device or Eustachian tube ET.

Figure 15D:
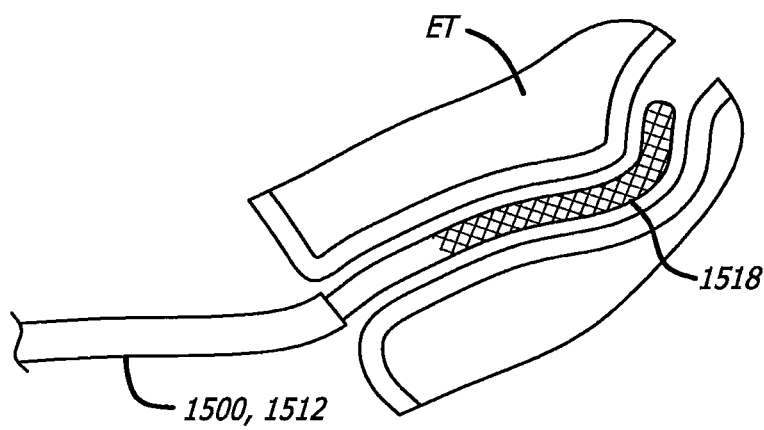
Figure 15E:
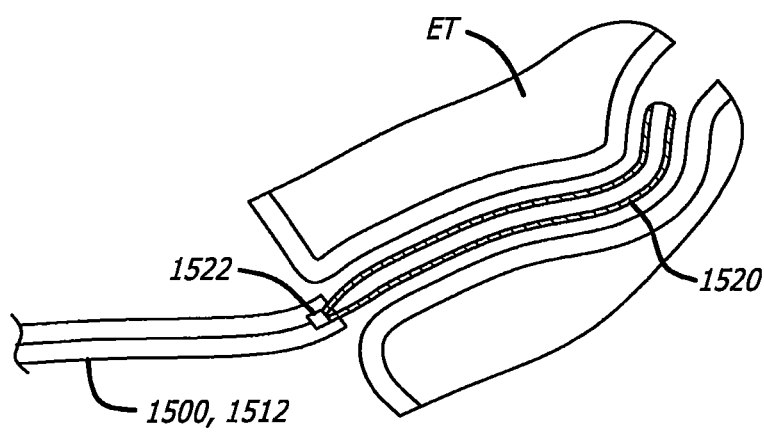

FIG. 15D shows the device 1500 or 1512 in use, according to one embodiment. In this embodiment the device 1500 includes a stent 1518 which may be expanded within the Eustachian tube ET. The stent may include a shape-memory alloy construction or a deformable construction which is expanded by the balloon 1508.

FIG. 15D shows the device 1500 or 1512 in use, according to one embodiment. In this embodiment the device 1500 includes a detachable insert 1520. The detachable insert may be detached at junction 1522. In this example, the insert 1520 includes a lumen. The insert 1520 may be biodegradable and deliver a therapeutic substance over time. In one embodiment, the insert 1520 may include an attachment member for attaching the insert 1520 to mucosal tissue within the nasal cavity, so that the insert 1520 will not migrate from the area into which it is placed. This attachment member (or multiple members) may be attached to the insert 1520 at or near its proximal end, so that when the insert 1520 is placed in the Eustachian tube, the attachment member extends into the nasal cavity and can be attached by the physician to the mucosal tissue. Any suitable attachment member may be used in various embodiment, such as but not limited to a suture loop, clips, barbs or the like.

Figure 15F:
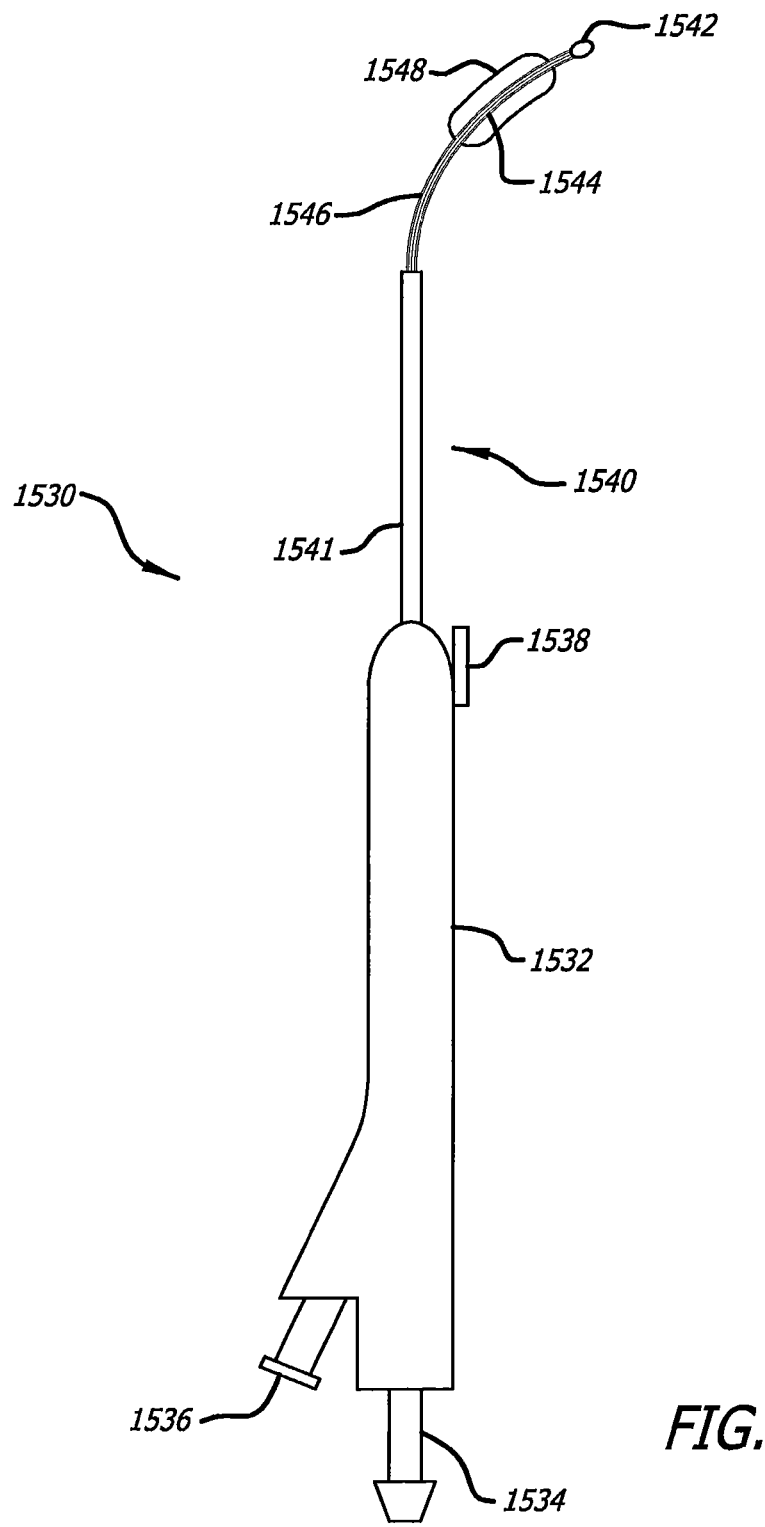
FIG. 15F shows a side elevational view of a dilation device for providing therapy to a Eustachian tube.

FIG. 15F shows another alternative embodiment of a guidewire-free Eustachian tube dilation device 1530. In this embodiment, the dilation device 1530 includes a handle 1532 coupled with a sliding balloon catheter 1540 and a malleable guide member (or "shaft") 1544 over which the balloon catheter 1540 slides. Also coupled with the handle 1532 are a suction port 1534, an inflation port 1536, and a sliding actuator 1538 for advancing and retracting the balloon catheter 1540 along the guide member 1544. In this embodiment, the balloon catheter includes a rigid proximal portion 1541, a distal flexible portion 1546, and an inflatable balloon 1548. The guide member 1544 may include a ball tip 1542 similar to those found on a distal end of a ball-tip seeker frequently used by ENT physicians during sinus surgery. Proximal shaft portion 1541 may be made of any suitable material. For example, in one embodiment, the proximal shaft portion 1541 may be a stainless steel hypotube. The flexible distal shaft portion 1546 may be made of any flexible material, such as a flexible polymer, and the balloon 1548 may be made of any suitable non-compliant, semi-compliant or compliant material, including but not limited to PET, Nylon or Pebax. In various embodiments, the guide member 1544 may be flexible, malleable or rigid, and may be made of stainless steel, Nitinol or any other suitable material.

In use, the dilation device 1530 may be advanced into a nostril, and the guide member 1544, with its ball tip 1542, may be used to seek out and locate the opening to a Eustachian tube, much the same way that ENT physicians use a ball tip seeker to find the opening of a paranasal sinus. Once the Eustachian tube opening is located, the guide member 1544 may be advanced through the opening, and the sliding actuator 1538 may be advanced along a slot (not visible in FIG. 15F) in the handle 1532 to advance the balloon catheter 1540 along the guide member 1544. The balloon catheter 1546 is advanced to position the balloon 1548 at a desired location within the Eustachian tube. The balloon 1548 may then be inflated via inflation port 1536 to expand/dilate a portion of the Eustachian tube, and the balloon 1548 may then be deflated. The balloon 1548 may subsequently either be removed from the patient, repositioned within the same Eustachian tube to dilate additional portions, or repositioned to the contralateral Eustachian tube to dilate that tube. The procedure may be performed as many times and in any combinations of locations as desired on a patient. In some embodiments, the dilation device 1530 may also be used to dilate an opening into a paranasal sinus (or multiple paranasal sinus openings). The paranasal sinus opening dilation may be performed before and/or after the Eustachian tube dilation and may involve openings into the frontal, sphenoid, maxillary or ethmoid sinuses. In some embodiments, the dilation device 1530 may be removed from the patient between dilations to allow the user to bend a malleable portion of the guide member 1544 to different angles to facilitate accessing different sinus and/or Eustachian tube openings.

In an alternative embodiment, the guide member 1544 may be an outer tube through which the balloon catheter 1540 advances. Such a tube may be predominantly rigid, part rigid/part flexible, or mostly flexible. In another alternative embodiment, the guide member 1544 may include both an inner shaft and an outer tube. In yet another embodiment, the balloon catheter 1540 may be fixedly attached to the guide member 1544 (or shaft). In another embodiment, there may be no guide member but simply a rigid or partially rigid and/or malleable balloon catheter 1540, which may be advanced into the Eustachian tube by itself without using a guide. In other embodiments, any other suitable dilation device may be substituted for the balloon catheter 1540, such as but not limited to a mechanical dilator such as an expandable metal basket including multiple tines.

Figure 16A:
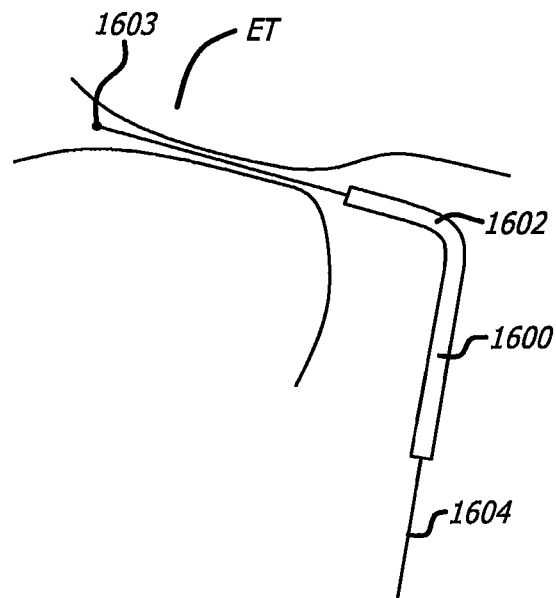
FIGS. 16A and 16B show a partial cross-section of devices being used in a method for treating a Eustachian tube of a patient.
Figure 16B:
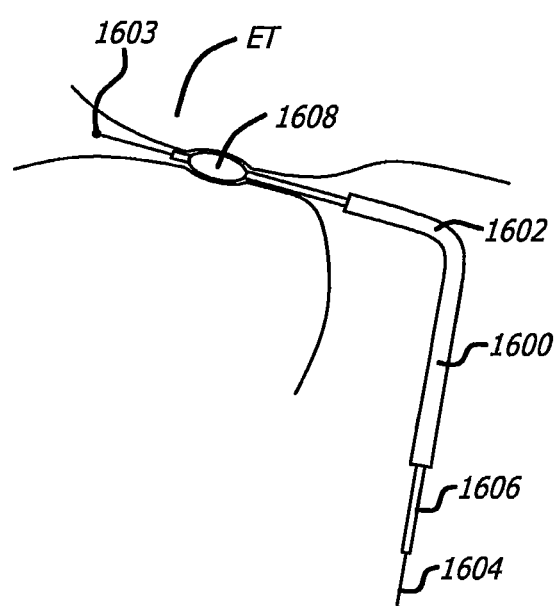

FIGS. 16A and 16B show a method for providing therapy to a Eustachian tube of a patient, according to one embodiment. Before the treatment method is performed, the physician may apply a local anesthesia to the nasal cavity and/or the Eustachian tube. In cases performed under general anesthesia, the physician may choose not to apply local anesthesia, while in cases performed on a conscious patient, local anesthetic may be applied. In general, the method may include any preparation/anesthesia technique desired. In some embodiments, for example, a physician may choose to irrigate the nasal cavity and/or Eustachian tube before performing a treatment. This may be in addition to anesthesia or in cases where local anesthesia is not applied.

After any desired preparation of the nasal cavity and/or Eustachian tube, a guide catheter 1600 may be routed through a nasal passage of a patient and placed adjacent to the opening of a Eustachian tube ET. In various embodiments, the guide catheter 1600 may be advanced to a Eustachian tube through either the ipsilateral or contralateral nostril, and generally the guide catheter 1600 will have a different bend angle depending on the approach. In the embodiment shown, a distal portion 1602 of the guide catheter 1600 includes a bend having an angle between 30 and 90 degrees (or any other angles in alternative embodiments). In one embodiment, the distal portion 1602 may be more flexible than the proximal portion of the guide catheter 1600. In one embodiment, the distal portion 1602 of the guide catheter may be malleable. Accordingly, a user may bend the distal portion 1602 to place the guide catheter 1600 in a desired position with relation to the Eustachian tube ET.

After the guide catheter 1600 is in a desired position, a guidewire 1604 may then be advanced through the guide catheter 1600 and into the Eustachian tube ET. In the embodiment shown, the guidewire 1604 includes a ball tip 1603 to prevent passage of the guidewire 1604 through a distal, small diameter portion of the Eustachian tube. Other embodiments may include a curved distal tip or other stop mechanism to achieve the same purpose. As mentioned above, although this embodiment of a method for treating a Eustachian tube involves the guide catheter 1600 and guidewire 1604, alternative treatment methods may involve a guide catheter 1600 alone, a guidewire 1604 alone, or may be performed without any guide device.

In FIG. 16B, a dilation catheter 1606 is advanced over the guidewire 1604 and through the guide catheter 1600 to position a dilator 1608 of the dilation catheter 1606 within the Eustachian tube ET. In an alternative embodiment, the guide catheter 1600 may be optionally removed from the patient before advancing the dilation catheter 1606 over the guidewire 1604. In another alternative embodiment, the dilation catheter 1606 may be advanced into the Eustachian tube through the guide catheter 1600 without using a guidewire 1604. The dilation catheter 1606 generally includes an elongate shaft and the dilator 1608. The dilator 1608 may be a polymer balloon (compliant, semi-compliant or non-compliant). In some embodiments, the balloon may be porous, to deliver a therapeutic or diagnostic agent when pressurized. Alternatively, the dilator 1608 may be a mechanically expandable basket constructed from a plurality of metal or polymer tines or any of a number of other suitable mechanical dilation devices. The dilation catheter 1606 generally includes proximally located connections/provisions for inflating/activating the dilator 1608. A therapeutic or diagnostic agent may be applied to the interior of the Eustachian tube ET before or after the insertion of the dilation catheter 1606, for example, via a spray catheter or a spray lumen of the guide catheter 1600. In one embodiment, for example, the dilation catheter 1606 may include a fluid introduction lumen (or multiple lumens) for introducing irrigation fluid, anesthetic fluid, therapeutic drug or other substances into the Eustachian tube. In one embodiment, this same lumen or a separate lumen may be used to suction fluids/substances out of the Eustachian tube.

The dilator 1608 may be expanded to dilate the Eustachian tube ET after it is placed in a desirable location therein. For example, the opening area of the Eustachian tube ET includes a pharyngeal ostium, and the dilation catheter 1606 may be advanced to position the dilator 1608 in the pharyngeal ostium. An endoscope may be used to assist in positioning the dilation catheter 1606. The endoscope may be advanced through the nasal passage to view the dilation catheter 1606. A marker on a shaft of the dilation catheter 1606 can be viewed from the endoscope to approximate a location of the dilator 1608 relative to the opening of the Eustachian tube ET based on a distance of the marker from a proximal end of the dilator 1608. Accordingly, the dilation catheter 1606 can be moved to place the marker in a desirable location before expansion of the dilator 1608 in the Eustachian tube ET.

The dilator 1608 may be held in location while in an expanded state for an extended period of time (e.g. several seconds or minutes). The dilator 1608 may also deliver a substance to the Eustachian tube ET, such as one or more of the therapeutic or diagnostic agents described herein. The dilator 1608 may also carry an expandable stent for delivery into the Eustachian tube upon expansion of the dilator 1608. The dilation catheter 1606, guide catheter 1600 and guidewire 1604 may be removed from the patient after the dilator is 1608 has been deflated/unexpanded.

As mentioned above, in an alternative embodiment, a balloon dilation catheter may sometimes be capable of being advanced into and used within a Eustachian tube without the use of a guidewire, guide catheter or other guiding device. Such a balloon catheter would need to have sufficient overall stiffness to allow it to be passed through the nasal cavity and into the Eustachian tube without a guide device, but ideally at least a distal portion of the catheter would also be flexible enough to advance into and conform to the shape of the tortuous Eustachian tube without causing unwanted damage. In some embodiments, such a balloon dilation catheter may have an adjustable stiffness along at least a portion of its length. For example, in one embodiment the catheter may have a malleable portion that a physician user may adjust with his/her hand before insertion. It may be even more advantageous, however, to have a catheter that may be advanced into the Eustachian tube with one amount of stiffness and then adjusted to a different amount of stiffness. For example, it may be desirable to have a catheter that is relatively stiff until its distal end has passed into the Eustachian tube and then can be made more flexible for tracking farther into the Eustachian tube. In one embodiment, this adjustable stiffness may be achieved using a sliding stiffening mandrel that extends into the distal portion of the catheter in which the stiffness adjustment is desired and extends proximally to a slide member on a handle or proximal portion of the catheter, which the user uses to make the adjustment. In other embodiments, the stiffening member (or members) may comprise one or more core wires, ribbons, compressible fluids or the like. The proximal member used to control the stiffness may comprise a slide, dial, button or other actuator.

Figure 17A:
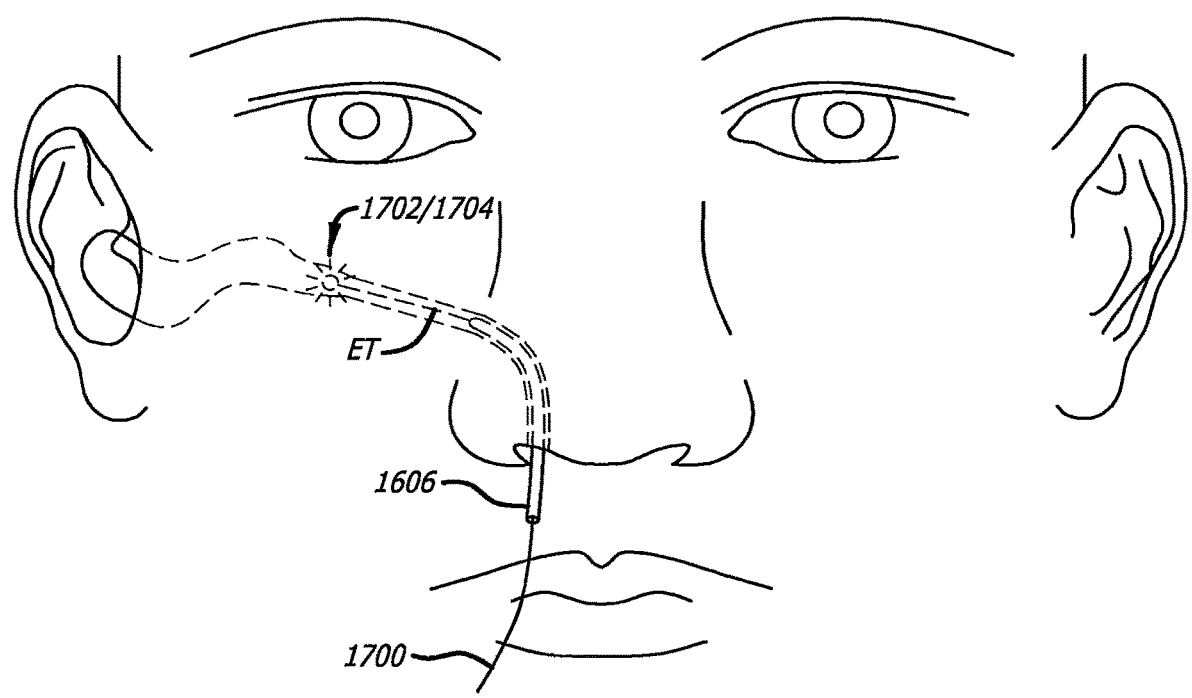
FIG. 17A shows a frontal view of an illuminated guidewire for treating a Eustachian tube in use in a patient.

FIG. 17 shows an illuminated guidewire 1700 in use, according to one embodiment. The illuminated guidewire 1700 is used in the same manner as the guidewire 1604 described above. However, the illuminated guidewire 1700 provides illumination at a distal tip 1702, which is visible to a user through the tympanic membrane or on the external face of the patient (commonly referred to as "transillumination"). The user may place the distal tip 1702 at a desired location based on the position of a light point 1704 passing through the patient's tissue. The light point 1704 may be used as a point of reference for the placement of other devices based on the relative distance from the light point 1704. The light point 1704 may also provide a secondary or primary light source for an endoscope which is viewing the pharyngeal ostium of the Eustachian tube ET. The illuminated guidewire 1700 may include a fiber optic channel for passing light from a light source to the distal tip 1702. Examples of illuminated guidewires and scopes which may be used in conjunction with this disclosure are shown and described in commonly assigned U.S. patent application Ser. No. 11/522,497, issued as U.S. Pat. No. 7,559,925 on Jul. 14, 2009, the entirety of which is incorporated by reference herein.

Figure 18A:
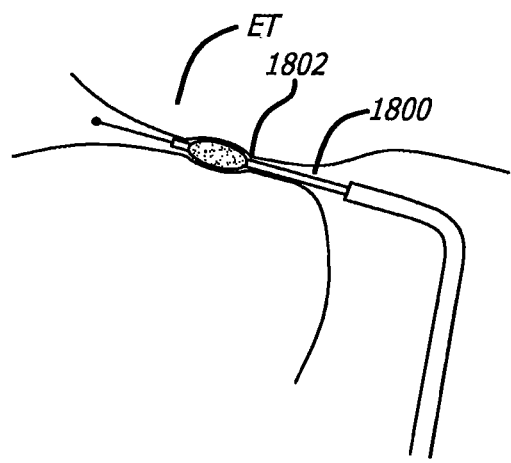
FIGS. 18A and 18B show a partial cross-section of a device being used in a method for treating a Eustachian tube of a patient.
Figure 18B:
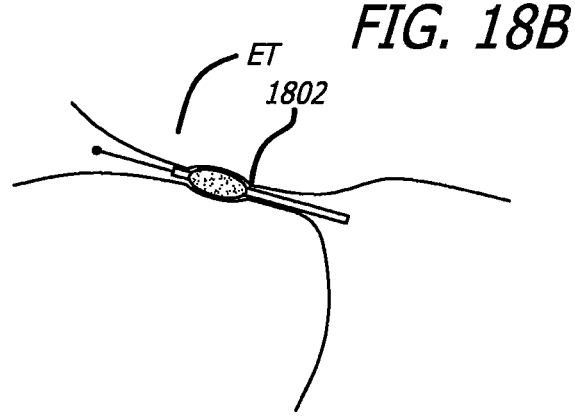

FIGS. 18A and 18B show a dilation catheter 1800 according to an alternative embodiment. The dilation catheter 1800 includes a detachable dilator 1802. The detachable dilator 1802 may be detached from the dilation catheter 1800 after the detachable dilator 1802 has been expanded within the Eustachian tube ET. The detachable dilator 1802 may include a one-way valve, which allows the detachable dilator 1802 to remain dilated after detachment from the dilation catheter 1800. A breakable joint may join the detachable dilator 1802 and the dilation catheter 1800. The detachable dilator 1802 may include at least one lumen to allow the passage of a pressurizing fluid. In use, the dilation catheter 1800 may be positioned and expanded to dilate a portion of the Eustachian tube as described for previous embodiments. After the detachable dilator 1802 is inflated, it may be detached at the breakable joint via a twisting or pulling force applied at the proximal portion of the dilation catheter 1800. The one-way valve prevents the detachable dilator 1802 from deflating after detachment from the dilation catheter 1800. The detachable dilator 1802 may include a therapeutic or diagnostic agent to treat the Eustachian tube ET. Pressure within the Eustachian tube ET may be balanced via the lumen while the detachable dilator 1802 remains dilated therein. The detachable dilator 1802 may be removed by pulling it out of the Eustachian tube ET and in some embodiments by also puncturing the detachable dilator 1802.

Figure 18C:
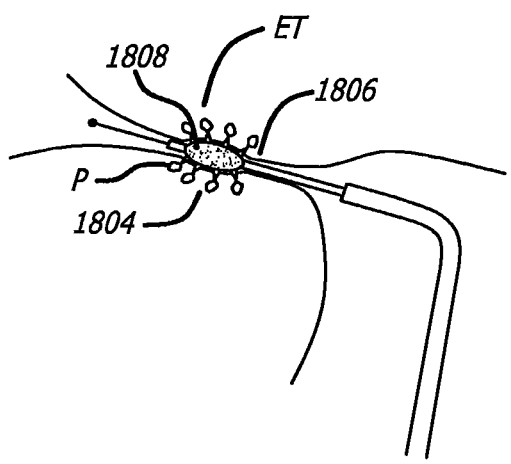
FIG. 18C shows a partial cross-section of a device being used in a method for treating a Eustachian tube of a patient.

FIG. 18C shows a dilation catheter 1804 according to an alternative embodiment. The dilation catheter 1804 includes a plurality of extendable needles 1806, which may extend through passages in the dilator 1808. Each needle 1806 can be fluidly connected to a therapeutic or diagnostic agent source, such as a syringe. Different needles 1806 can be connected to different kinds of therapeutic or diagnostic agents. In use, the dilation catheter 1800 may be positioned and expanded to dilate a portion of the Eustachian tube as described for previous embodiments. After the dilator 1808 is inflated, the needles 1806 may be advanced through the dilator 1808 and into tissue of the Eustachian tube ET. The needles 1806 may then inject one or more kinds of therapeutic or diagnostic agents into the tissue of the Eustachian tube ET as shown by the substance plumes P. After the substance has been injected into the tissue of the Eustachian tube ET, the needles may be withdrawn back into the dilation catheter 1804 and the dilation catheter 1804 may be removed from the Eustachian tube ET.

Figure 18D:
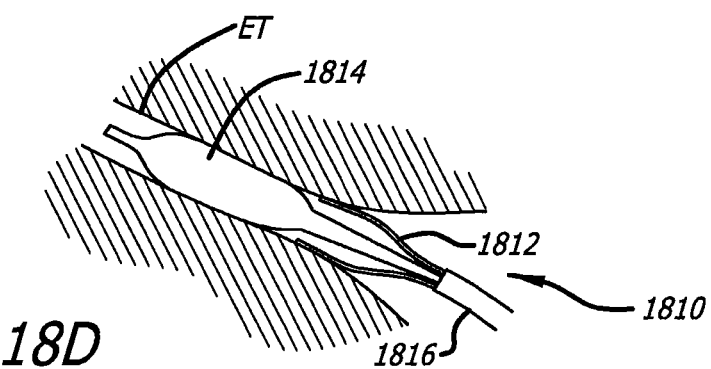
FIG. 18D shows a partial cross-section of a device being used in a method for treating a Eustachian tube of a patient.

FIG. 18D shows a dilation catheter 1810 according to an alternative embodiment of the dilation catheter 1606. The dilation catheter 1810 includes at least one pair of opposed lateral wings 1812, which help maintain the position of the dilator 1814 in the Eustachian tube ET. More than one pair of opposed lateral wings 1812 may be used. The lateral wings 1812 do not have to be positioned directly opposite each other, and configurations of odd-numbered lateral wings 1812 may be used. The lateral wings 1812 can be constructed from elongate tines which are spring biased to expand when advanced out of the shaft 1816 of the dilation catheter 1810. Withdrawing the slidably housed lateral wings 1812 will cause them to collapse within the shaft 1816. The lateral wings 1812 can be manipulated at the proximal end of the dilation catheter 1810, for example, through actuation of a slider mechanism. The lateral wings 1812 can include spikes or grips to help maintain immovable contact with the Eustachian tube ET. In use, the dilator 1814 and lateral wings 1812 are advanced out of the shaft 1816 simultaneously, or non-simultaneously (i.e. the lateral wings 1812 may be advanced before or after the dilator 1814). The lateral wings 1812 apply force to the walls of the opening of the Eustachian tube ET, which helps maintain the dilator 1814 in a desired position. The lateral wings 1812 may be withdrawn back into the shaft 1816 after the dilator 1814 has applied the desired therapy to the Eustachian tube ET.

Figure 18E:
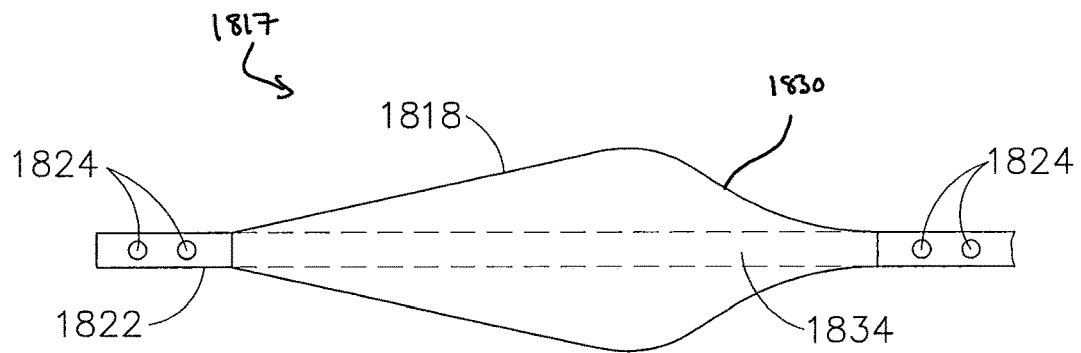
FIG. 18E shows a side view of a dilator for providing therapy to a Eustachian tube of a patient.
Figure 18F:
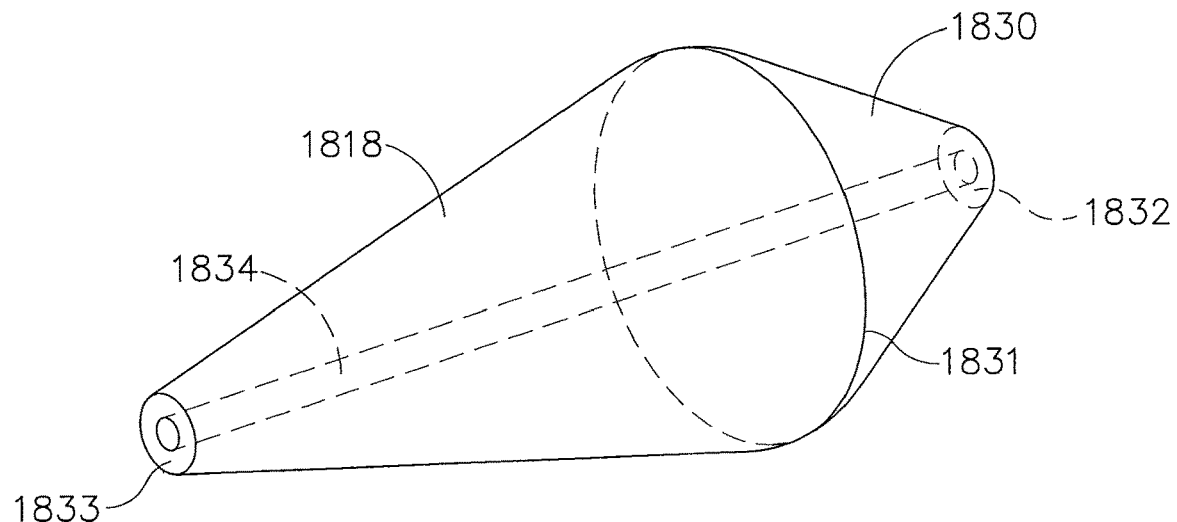
FIG. 18F shows a perspective view of the dilator of FIG. 18E.
Figure 18G:
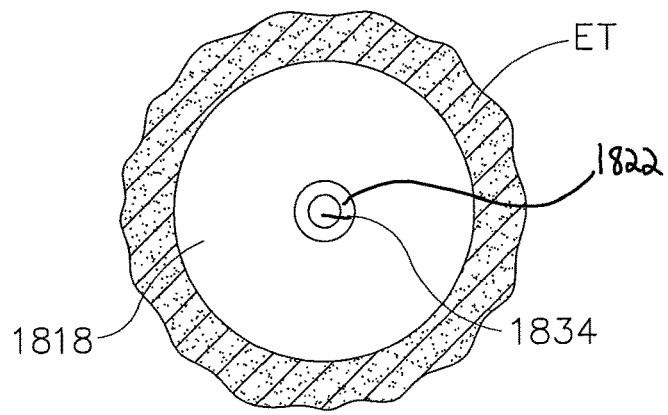
FIG. 18G shows a cross-sectional view of the dilator of FIG. 18E within the Eustachian tube of a patient, with the dilator in an expanded state.
Figure 18H:
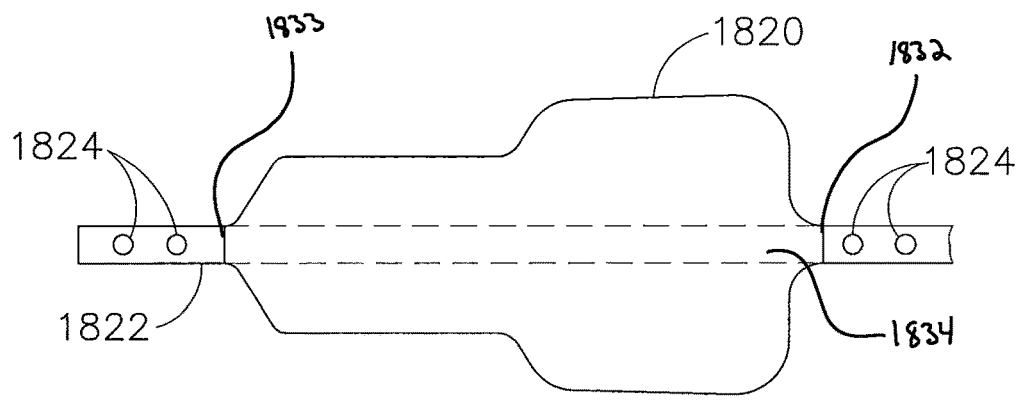
FIG. 18H shows a side view of a dilator for providing therapy to a Eustachian tube of a patient.
Figure 18I:
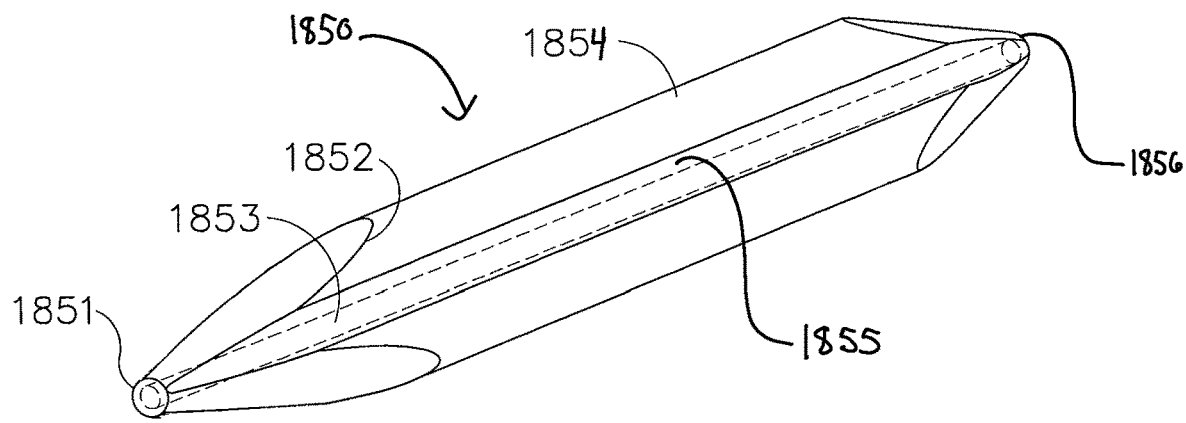
FIG. 18I shows a perspective view of a dilator for providing therapy to a Eustachian tube of a patient.
Figure 18J:
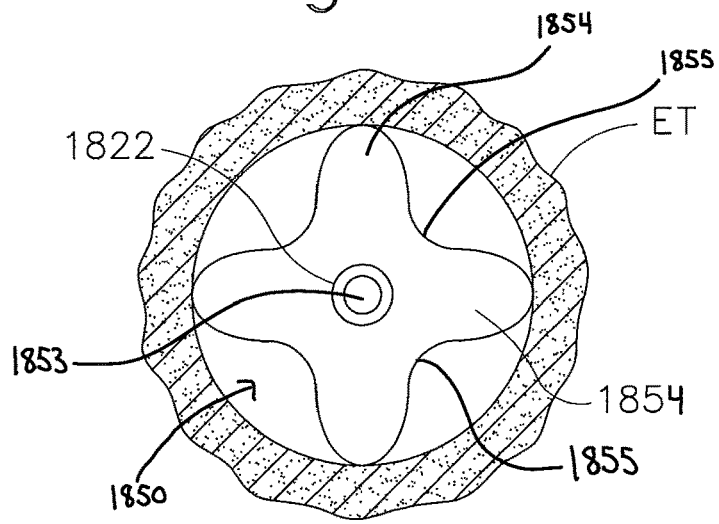
FIG. 18J shows a cross-sectional view of the dilator of FIG. 18I within the Eustachian tube of a patient, with the dilator in an expanded state.
Figure 18K:
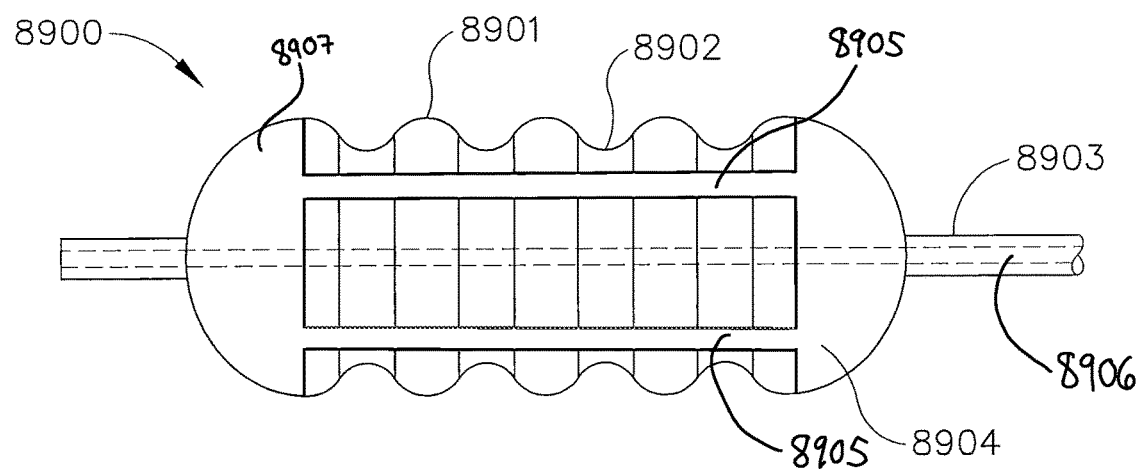
FIG. 18K shows a side view of a dilator for providing therapy to a Eustachian tube of a patient.
Figure 18L:
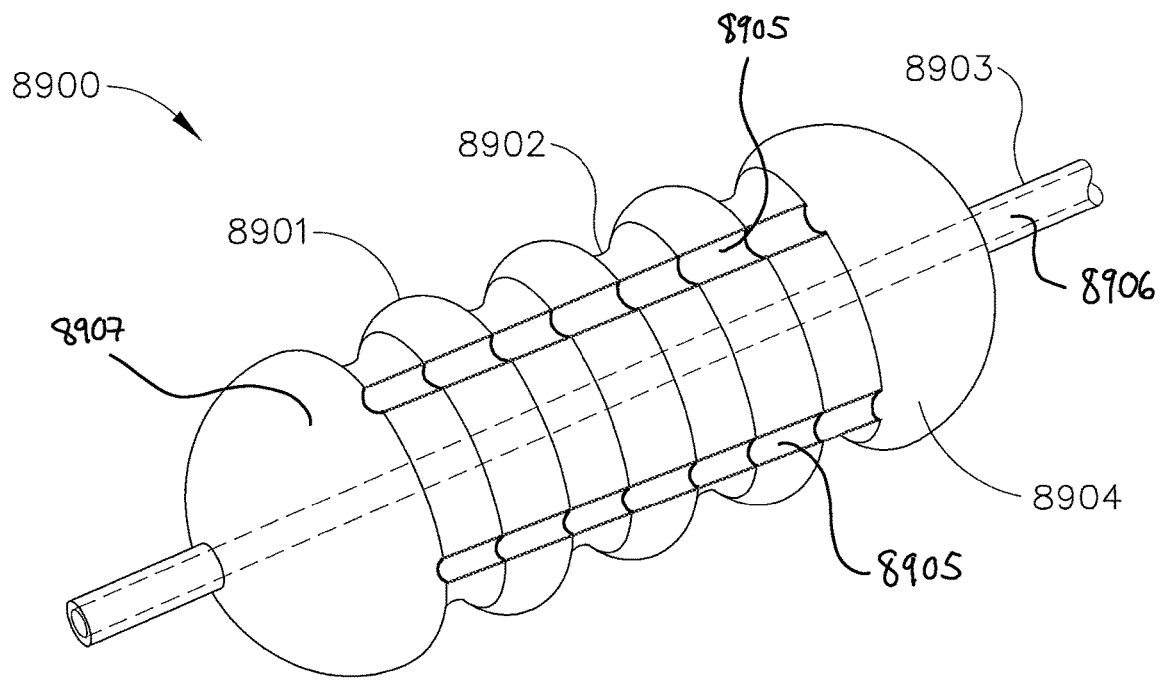
FIG. 18L shows a perspective view of the dilator of FIG. 18K.
Figure 18M:
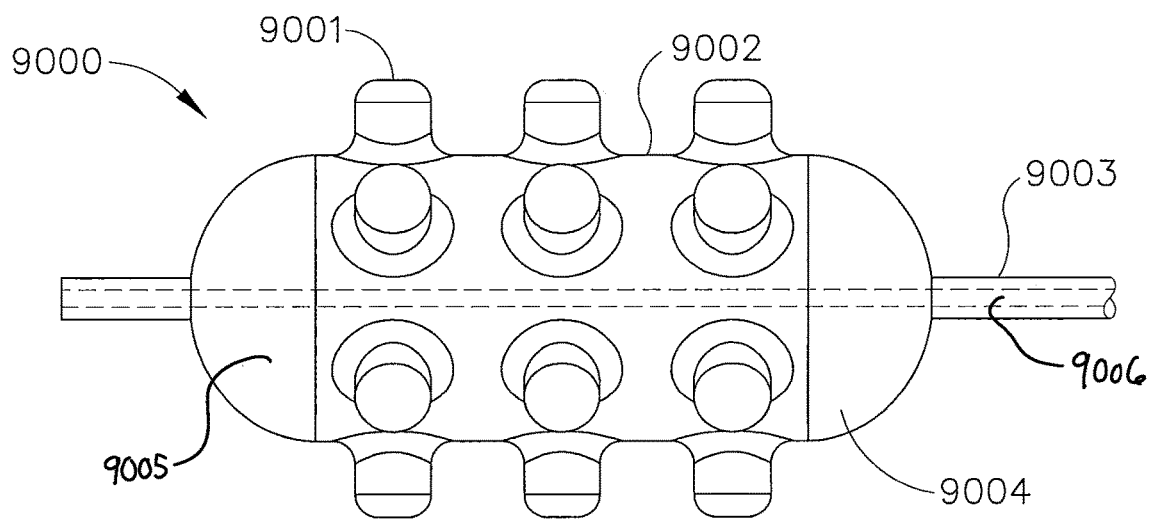
FIG. 18M shows a side view of a dilator for providing therapy to a Eustachian tube of a patient.
Figure 18N:
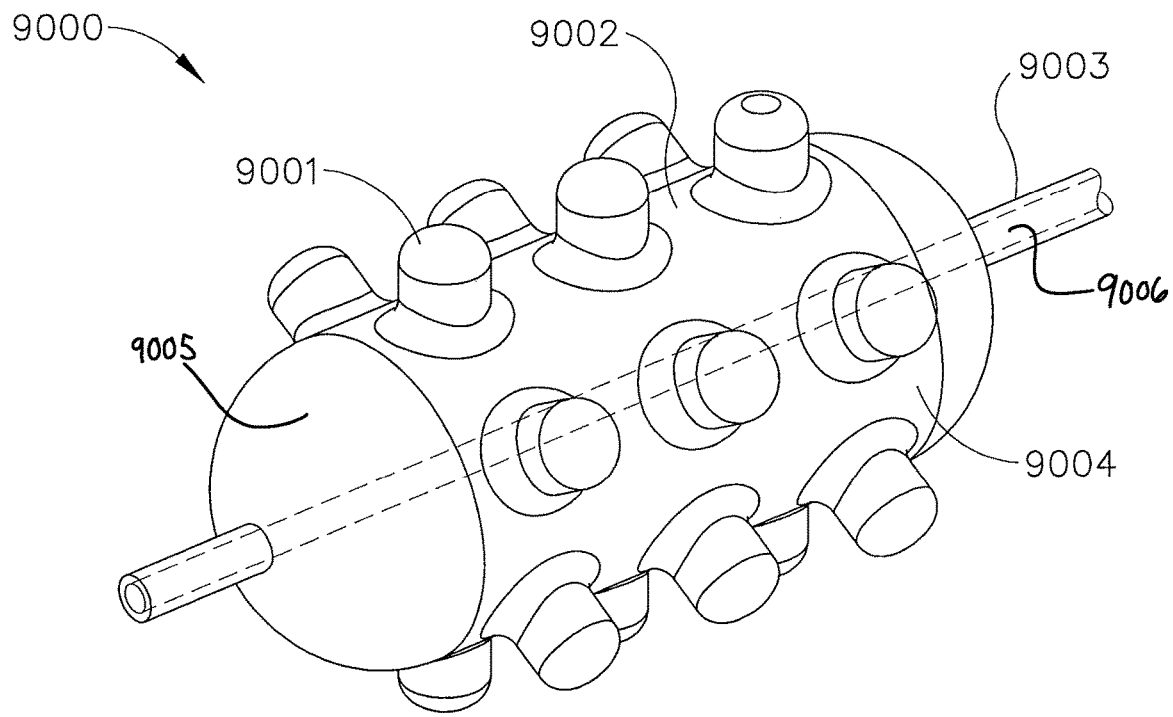
FIG. 18N shows a perspective view of the dilator of FIG. 18M
Figure 18O:
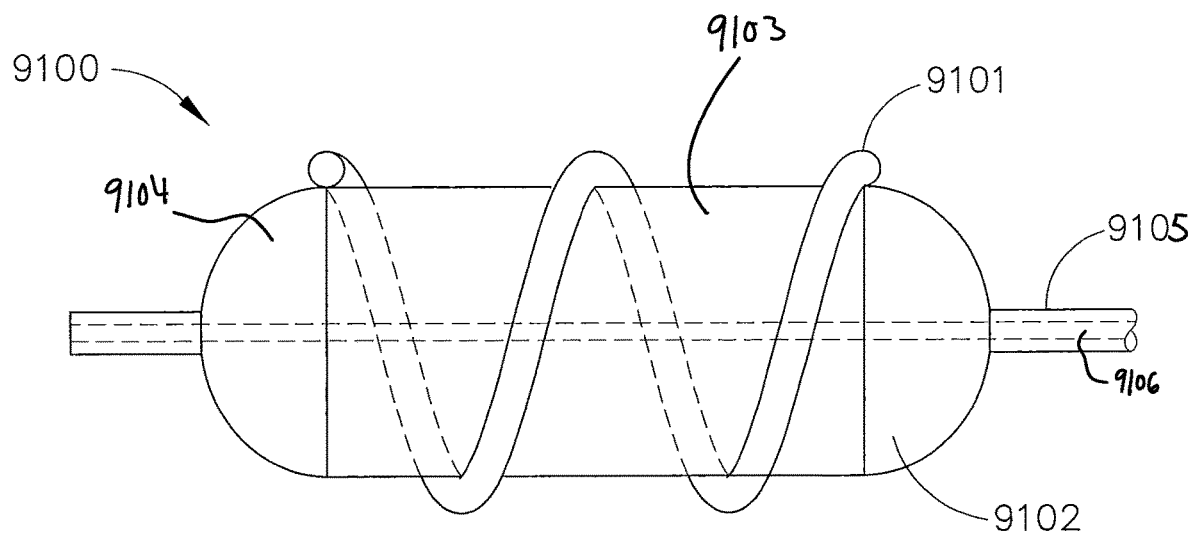
FIG. 18O shows a side view of a dilator for providing therapy to a Eustachian tube of a patient.
Figure 18P:
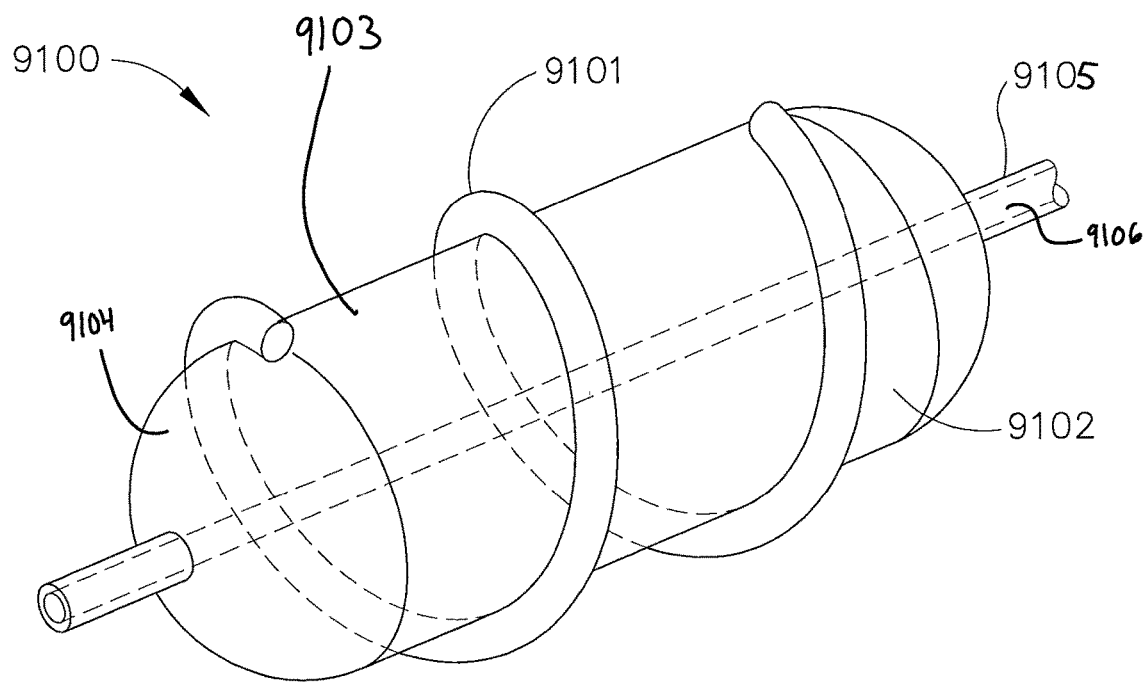
FIG. 18P shows a perspective view of the dilator of FIG. 18O
Figure 18Q:
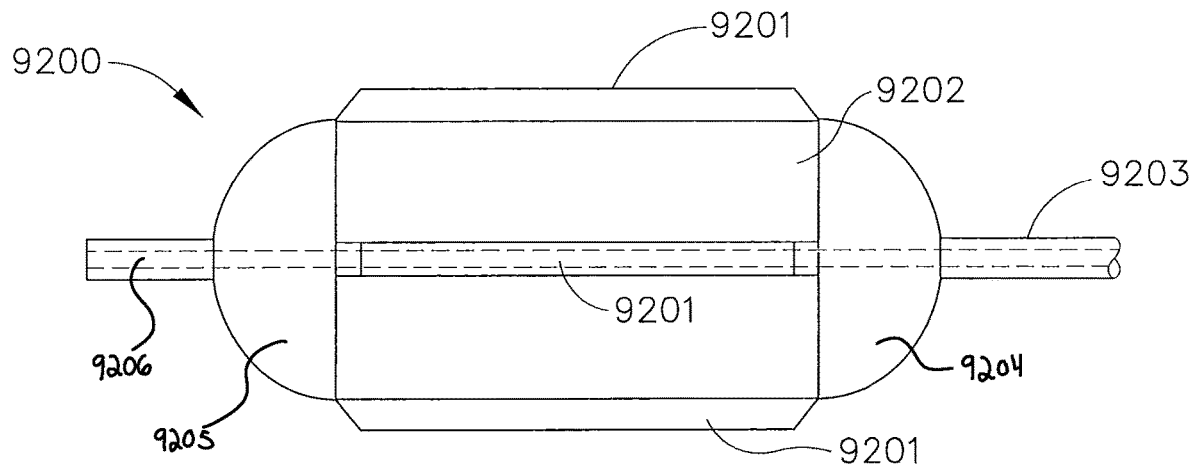
FIG. 18Q shows a side view of a dilator for providing therapy to a Eustachian tube of a patient.
Figure 18R:
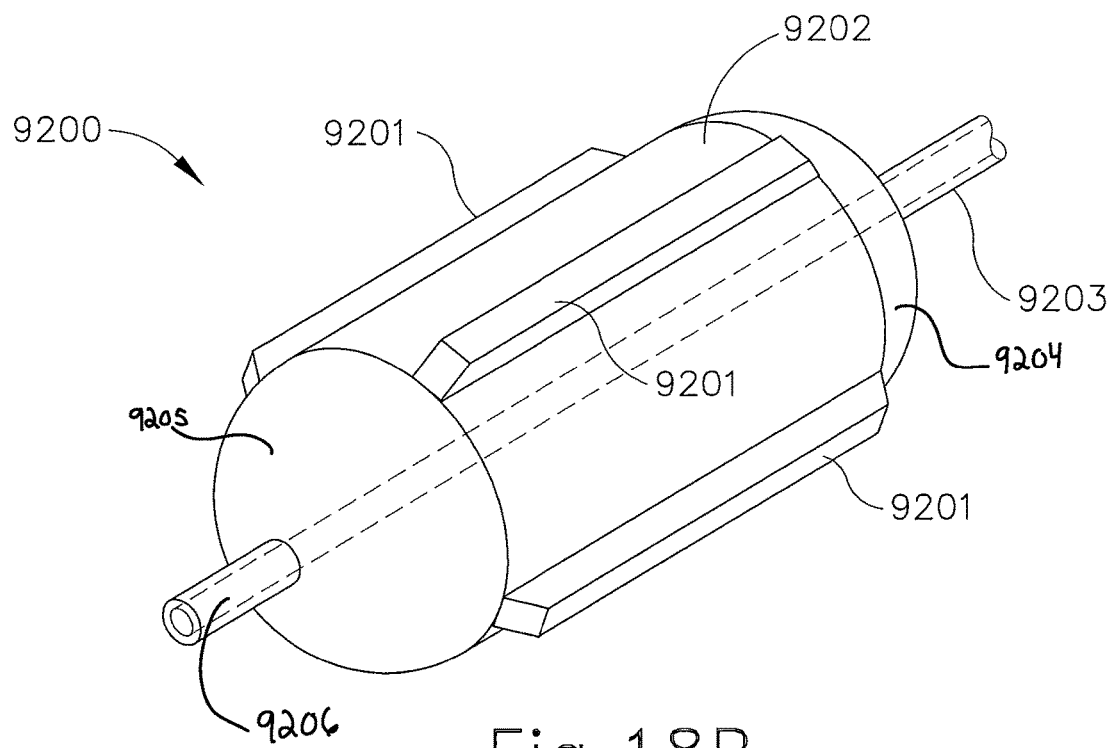
FIG. 18R shows a perspective view of the dilator of FIG. 18Q
Figure 18S:
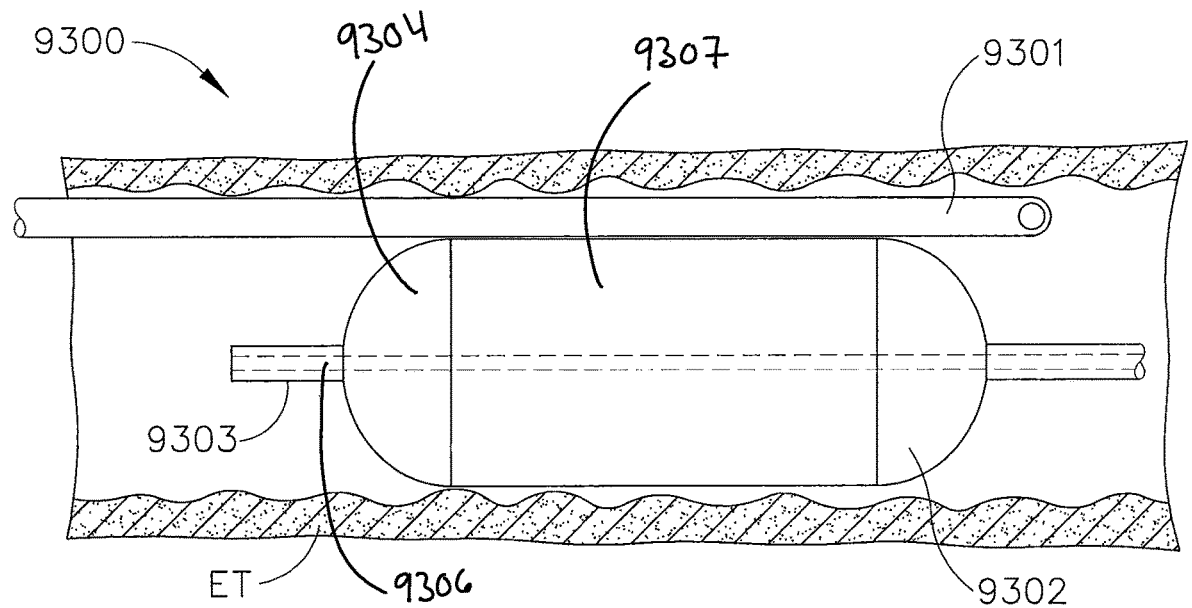
FIG. 18S shows a side view of a dilator for providing therapy to a Eustachian tube of a patient, disposed within a Eustachian tube of a patient.
Figure 18T:
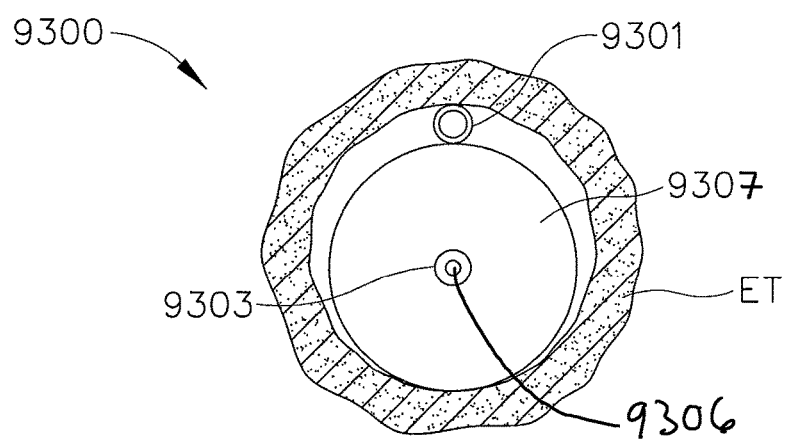
FIG. 18T shows a cross-sectional view of the dilator of FIG. 18S within the Eustachian tube of a patient, with the dilator in an expanded state.

FIGS. 18E-T show various views of alternative embodiments of the dilator 1608. For instance, FIGS. 18E-G show a dilator 1817 that has a tapered, conical shape, which complements the tapered geometry of the Eustachian tube ET, to enhance dilation thereof. The tapered, conical shape of dilator 1817 is formed by a proximal end 1832, a tapered proximal surface 1830, a maximum diameter 1831, a tapered distal surface 1818, and a distal end 1833. In the present example, tapered distal surface 1818 has a longitudinal length of about 12 to 18 millimeters, maximum diameter 1831 has a diameter of about 6.5 millimeters, and proximal end 1832 and distal end 1833 have a diameter of about 4.5 millimeters. Alternatively, any other suitable dimensions may be used. Dilator 1820 may also have a variable shape, such as the stepped shape shown in FIG. 18H. With this stepped shape, dilator 1820 has at least two different outer diameters—a first outer diameter extending along a proximal length of dilator 1820 and a second outer diameter extending along a distal length of dilator 1820, with an angled transition between these outer diameters.

Problems may arise from dilator 1817, 1820 dilating the Eustachian tube ET by making uniform contact along the full circumference of the Eustachian tube ET. When dilator 1817, 1820 expands within the Eustachian tube, air is displaced due to the increase in volume of dilator 1817, 1820. If the air travels toward middle ear 14, rather than toward nasopharynx region of the throat 30, pressure may build in middle ear 14, leading to possible damage to tympanic membrane 22. Pressure may build in part to dilator 1817, 1820 acting as a seal within the Eustachian tube ET. Providing fluid communication between proximal end 1832 and distal end 1833 of dilator 1817, 1820 may help release pressure build up that might otherwise occur in middle ear 14 due to expansion dilator 1817, 1820. In other words, it may be beneficial to provide a vent path that allows air to escape from the lateral region of the Eustachian tube ET as the expanding dilator 1817, 1820 begins to occupy the space in the lateral region of the Eustachian tube ET. Also, controlling the direction of the displaced air due to dilator 1817, 1820 expansion may also help prevent possible pressure build up in middle ear 14. The following are merely illustrative examples of different devices and methods that may be utilized to prevent pressure build up in middle ear 14, while also providing dilation of the Eustachian tube ET. Other examples of devices and methods will be apparent to a person having ordinary skill in the art in view of the teachings herein. It should be understood that the methods and dilator features described below can be combined in various ways in order to help prevent undesired pressure build up in middle ear 14.

As shown in FIGS. 18E and 18H, dilators 1817, 1820 can be attached to shaft 1822 that extends through both proximal end 1832 and distal end 1833 of dilator 1817, 1820. Shaft 1822 comprises a vent lumen 1834 extending through dilator 1817, 1820, a set of proximal pressure relief holes 1824 located proximal to proximal end 1832, and a set of distal pressure relief holes located distal to and distal end 1833. Pressure relief holes 1824 are oriented transversely through shaft 1822. Pressure relief holes 1824 may provide fluid communication between proximal end 1832 and distal end 1833 of dilator 1817, 1820 via vent lumen 1834. This fluid communication path may be utilized to prevent expansion of dilator 1817, 1820 from providing pressure build up in middle ear 14, thereby providing pressure balance within the Eustachian tube ET. In other words, as dilator 1817, 1820 is inflated, air in the region of the Eustachian tube ET that is distal to 1817, 1820 may escape via pressure relief holes 18240 as the inflating 1817, 1820 occupies that distal region of the Eustachian tube ET. The number of pressure relief holes 1824 shown in FIGS. 18E and 18H is merely exemplary. Shaft 1822 may include additional or fewer pressure relief holes 1824 if desired. It should also be understood that shaft 1822 would include a separate inflation lumen (not shown) that would be used to inflate/deflate dilator 1817, 1820. Such an inflation lumen would be fluidly isolated from vent lumen 1834. Moreover, the expandable portions of dilators 1817, 1820 would be fluidly isolated from vent lumen 1834.

FIGS. 18I-N show exemplary dilators 1850, 8900, 9000, 9100, 9200 that have a cross-sectional geometry that does not contact and occupy the entirety of the circumference of the Eustachian tube ET, thereby allowing fluid communication between the proximal and distal ends of dilators 1850, 8900, 9000, 9100, 9200 when inflated. Thus, as described in greater detail below, the cross-sectional geometry of dilators 1850, 8900, 9000, 9100, 9200 prevent a sealing effect from ever occurring.

FIGS. 18I-J show one exemplary cross-sectional geometry with dilator 1850. Dilator 1850 comprises a proximal end 1856, a distal end 1851, a lumen 1853, a plurality of lobes 1854 separated by a plurality of recesses 1855, and tapered surfaces 1852. In the present example, tapered surfaces 1852 are located on both proximal end 1856 and distal end 1851. However, tapered surfaces 1852 are merely optional, and can be present on one end or not present at all. In the present example, lobes 1854 are angularly spaced equidistantly from each other about a longitudinal axis defined by the shaft 1822. The cross-sectional shape of dilator 1850 is formed by the successive intervals of lobes 1854 and recesses 1855; and generally resembles a "+" sign. The cross-sectional shape of dilator 1850 provides limited contact with Eustachian tube ET when dilator 1850 is inflated, preventing a sealing effect from occurring. In other words, recesses 1855 provide ventilation paths along the length of dilator 1850. Optionally, as in dilators 1817, 1820, pressure relief holes may be utilized past proximal end 1856 and distal end 1851 to provide additional pressure relief. Additionally, tapered surfaces 1852 do not have to be uniform, but can have dimensional variations similar to that of tapered surfaces 1818, 1830 of dilator 1817, thereby allowing for a complementary fit of dilator 1850 with a Eustachian tube ET of a patient.

FIGS. 18K-P show examples of dilators 8900, 9000, 9100 that have varying cross-section geometry along the length of dilator 8900, 9000, 9100; yet still provide fluid communication between proximal and distal ends of dilator 8900, 9000, 9100 when inflated.

For example, FIGS. 18K and 18L show dilator 8900 comprising a proximal end 8904, a distal end 8907, ribs 8901 separated by annular recesses 8902, longitudinal recesses 8905 extending from proximal end 8904 to distal end 8907, and a shaft 8903 with a lumen 8904 extending through dilator 8900. Ribs 8901 are the aspect of dilator in contact with Eustachian tube ET, while annular recesses 8902 and longitudinal recesses 8905 provide pathways for fluid communication between proximal end 8904 and distal end 8907, thereby preventing any sealing effect that might otherwise lead to unwanted pressure buildup in middle ear 14 upon inflation of dilator 8900. Optionally, as in dilators 1817, 1820, pressure relief holes may be utilized in shaft 8903 past proximal end 8904 and distal end 8907 of dilator 8900 to provide additional pressure relief. Additionally, dimensions along the length of dilator 8900 do not have to be uniform, but can have dimensional variations similar to that of tapered surfaces 1818, 1830 of dilator 1817, thereby allowing for a complementary fit of dilator 8900 with a Eustachian tube ET of a patient.

FIGS. 18M and 18N show another example where dilator 9000 comprises a proximal end 9004, a distal end 9005, a dilator body 9002, discrete bumps 9001, and a shaft 9003 with a lumen 9006 extending through dilator 9000. Discrete bumps 9001 may be either symmetrically or randomly placed along dilator body 9002. When dilator 9000 inflates, discrete bumps 9001 may come in contact with a Eustachian tube ET of a patient. Discrete bumps 9001 have enough rigidity to act as spacers between dilator body 9002 and a Eustachian tube ET of a patient. By providing space between dilator body 9002 and the Eustachian tube ET, discrete bumps 9001 provide a ventilation path in that space between proximal end 9004 and distal end 9005 of dilator 9000 as dilator 9000 inflates. Fluid communication between proximal end 9004 and distal end 9005 thereby prevents any sealing effect, which might otherwise lead to unwanted pressure buildup in middle ear 14 as dilator 9000 inflates. Optionally, as in dilators 1817, 1820, pressure relief holes may be utilized in shaft 9003 past proximal end 9004 and distal end 9005 of dilator 9000 to provide additional pressure relief. Additionally, dimensions along the length of dilator 9000 do not have to be uniform, but can have dimensional variations similar to that of tapered surfaces 1818, 1830 of dilator 1817, thereby allowing for a complementary fit of dilator 9000 with a Eustachian tube ET of a patient.

FIGS. 18O and 18P show an example where dilator 9100 comprises a proximal end 9102, a distal end 9104, a body 9103, a spiral rib 9101 along the body 9103, and a shaft 9105 with a lumen 9106 extending through dilator 9100. Spiral rib 9101 provides contact with a Eustachian tube ET of a patient when dilator 9100 is inflated, preventing dilator body 9103 from providing a sealing effect. In other words, spiral rib 9101 provides a helical vent path along the space defined between body 9103 and the wall of the Eustachian tube ET. Therefore, spiral rib 9101 provides a ventilation path between proximal end 9102 and distal end 9104 of dilator 9100. Optionally, as in dilators 1817, 1820, pressure relief holes may be utilized on shaft 9105 past proximal end 9102 and distal end 9104 of dilator 9100 to provide additional pressure relief. Additionally, dimensions of along the length of dilator 9100 do not have to be uniform, but can have dimensional variations similar to that of tapered surfaces 1818, 1830 of dilator 1817, thereby allowing for a complementary fit of dilator 9100 with a Eustachian tube ET of a patient. It should be noted that more than one spiral rib 9101 may be used.

FIGS. 18Q and 18R show an example of dilator 9200 comprising a proximal end 9402, a distal end 9205, a body 9202, fins 9201 extending longitudinally along the exterior of body 9202, and a shaft 9203 with a lumen 9206 extending through proximal end 9204 and distal end 9205. When dilator 9000 inflates, fins 9201 may come in contact with a Eustachian tube ET of a patient. Fins 9201 have enough rigidity to act as spacers between dilator body 9202 and a Eustachian tube ET of a patient, preventing the wall of the Eustachian tube from sealing against body 9202. Therefore, fins 9201 provide a ventilation pathway between proximal end 9204 and distal end 9205 of dilator 9200 when fins 9201 are in contact with the Eustachian tube ET as dilator 9200 inflates. Such a ventilation path may prevent unwanted pressure buildup that might otherwise occur in middle ear 14 due to inflation of dilator 9200. Optionally, as in dilators 1817, 1820, pressure relief holes may be utilized on shaft 9203 past proximal end 9204 and distal end 9205 of dilator 9200 to provide additional pressure relief. Additionally, dimensions of along the length of dilator 9020 do not have to be uniform, but can have dimensional variations similar to that of tapered surfaces 1818, 1830 of dilator 1817, thereby allowing for a complementary fit of dilator 9200 with a Eustachian tube ET of a patient.

FIGS. 18S-T show an example of a dilator 9300 comprising a proximal end 9302, a distal end 9304, a body 9307, a venting tube 9301 that is non-coaxial with body 9307, and a shaft 9303 with a lumen 9306 extending through proximal end 9302 and distal end 9304 of dilator 9300. Venting tube 9301 can be attached to body 9307 and therefore inserted simultaneously with body 9307 into a Eustachian tube ET of a patient. Alternatively, venting tube 9301 can be detached from body 9307, allowing insertion of venting lumen into a Eustachian tube ET of a patient either before or after insertion of body 9307 in a Eustachian tube ET of a patient. Venting tube 9301 has an open distal end and an open proximal end, with a lumen extending therebetween. Venting tube 9301 thus effectively provides a ventilation path between the proximal end 9302 and distal end 9304 of dilator 9300. Venting is achieved through the inner lumen of venting tube 9301, through space S (FIG. 18T) between the wall of the Eustachian tube ET and regions of the walls of venting tube 9301 and body 9307, or through a combination of both. The venting prevents a sealing effect, which may otherwise lead to unwanted pressure buildup in middle ear 14 when dilator 9300 is inflated.

Figure 18U:
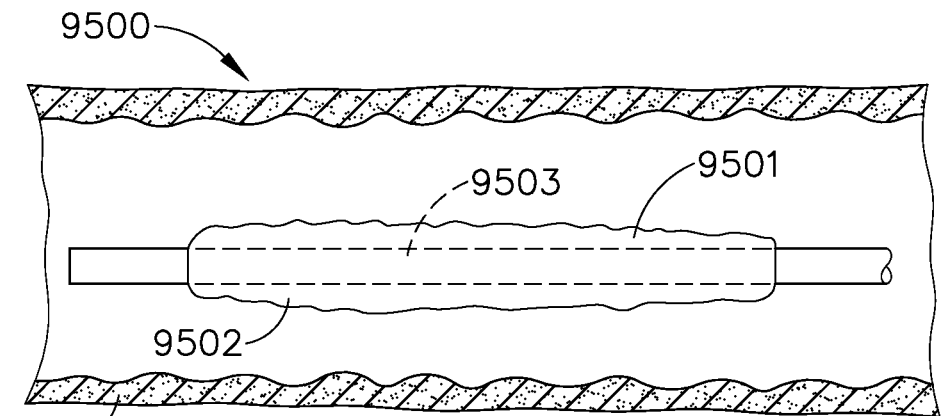
FIG. 18U shows a side view of a dilator for providing therapy to a Eustachian tube of a patient, disposed in a Eustachian tube of a patient, with the dilator in a deflated state.
Figure 18V:
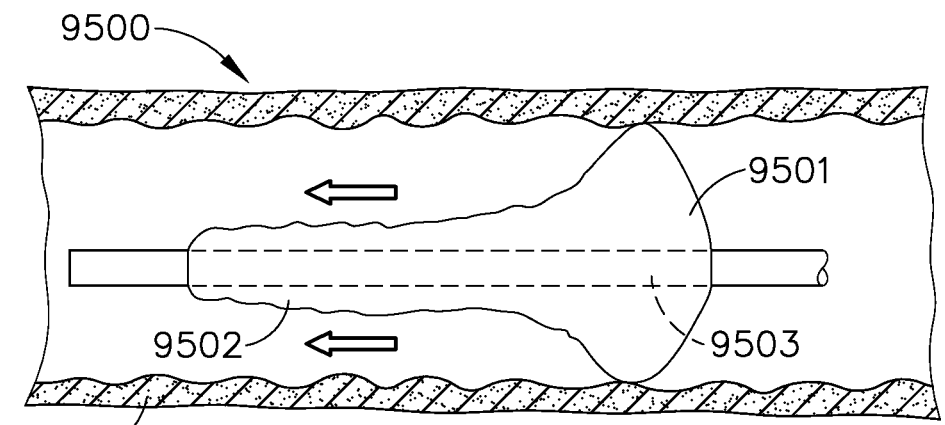
FIG. 18V shows a side view of the dilator of FIG. 18U disposed in the Eustachian tube of a patient, with the dilator in a semi-inflated state.
Figure 18W:
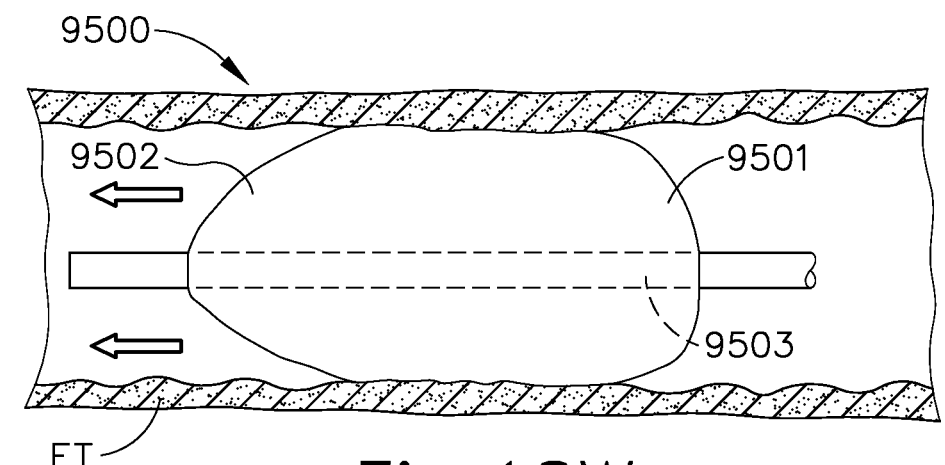
FIG. 18W shows a side view of the dilator of FIG. 18U disposed in the Eustachian tube of a patient, with the dilator in a fully inflated state.

Providing a path for ventilation through the geometry of dilator 1818, 1820, 1850, 8900, 9000, 9100, 9200, 9300 is merely one example of preventing pressure build up in the middle ear 14 during the dilation of the Eustachian tube ET. As another merely illustrative example, FIGS. 18U-W show a controlled inflation of a dilator 9500, forcing air toward the medial region of a Eustachian tube ET of a patient into the nasopharynx region of the throat 30. In FIG. 18U, dilator 9500 is in the Eustachian tube ET in a deflated state. In FIG. 18V, air is introduced to dilator 9500 in such a way that distal end 9501 of dilator 9500 inflates first. Inflating distal end 9501 of dilator 9500 first forces air in the proximal or medial direction as displayed by arrows in FIGS. 18U-W. Distal end 9501 of dilator 9500 provides a sealing effect thereby excluding forced air from middle ear 14. As additional fluid is communicated to dilator 9500, dilator 9500 continues to expand progressively along the length of dilator 9500, from the distal/lateral end 9501 of dilator 9500 toward the proximal/medial end 9502 of dilator 9500. FIG. 18W shows both proximal end 9502 and distal end 9501 dilated, thereby dilating the Eustachian tube ET.

Dilating distal end 9501 first, then progressing toward proximal end 9502, can be achieved in multiple ways. For instance, distal inflation can be achieved by designing distal end 9501 of dilator 9500 to have a smaller wall thickness compared to proximal end 9502 of dilator 9500. Alternatively, distal end 9501 could comprise a material with a smaller density than the material of proximal end 9502, therefore allowing distal end 9501 to inflate first. In yet another alternative, there could be a retractable outer sheath about the exterior of dilator 9500. The sheath may be initially placed in a distal position and may then be slowly retracted proximally as dilator 9500 is being inflated. Other methods of inflating distal end 9501 of dilator first, then progressing toward proximal end 9502, will be apparent to a person having ordinary skill in the art in view of the teachings herein.

Figure 18X:
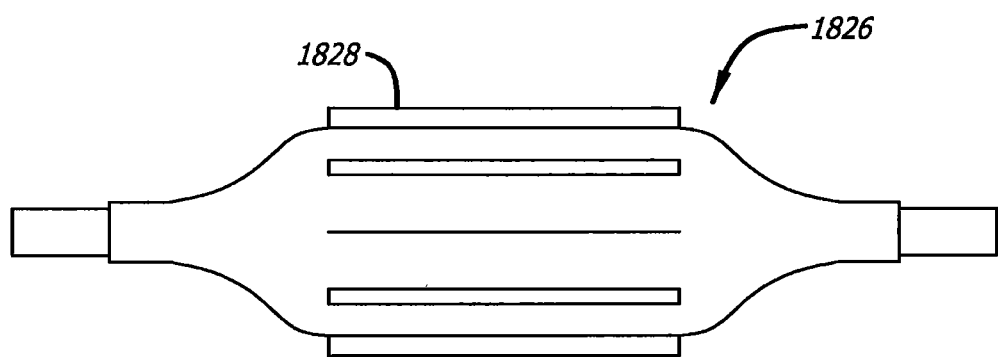
FIG. 18X shows a side view of a dilator for providing therapy to a Eustachian tube of a patient.
Figure 18Y:
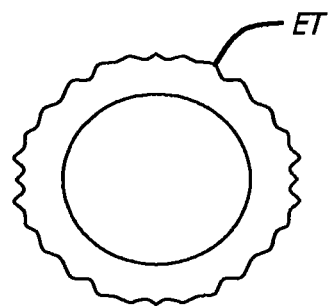
FIGS. 18Y and 18Z show before and after cross-sectional views of a Eustachian tube, respectively, that was treated by the dilator of FIG. 18X.
Figure 18Z:
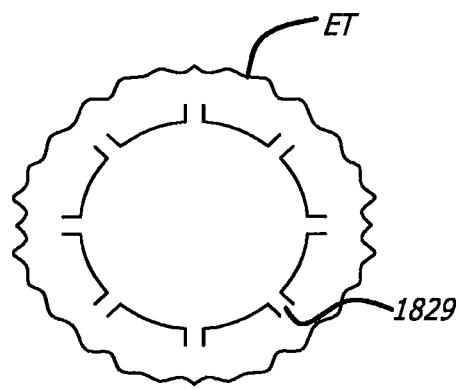

FIG. 18X shows a cutting (or "scoring") balloon dilator 1826 according to an alternative embodiment. The balloon dilator 1826 includes cutting members 1828 circumferentially placed around its exterior. In various embodiments, the cutting members 1828 may be wires, sharpened blades, one wire or sharpened blade, small barbs or raised sharp protrusions, or the like. The cutting members may be configured to deliver energy (e.g. RF). In use, the cutting members 1828 expand with the dilator to impinge on the Eustachian tube ET, which allows the dilator to open and stretch along controlled locations. FIGS. 18Y and 18Z show before and after representations of a treated Eustachian tube ET. Cutting the Eustachian tube ET along controlled sections 1829 allows the Eustachian tube ET to maintain an expanded shape by at least partially defeating the elastic response of the Eustachian tube ET wall.

In an alternative embodiment of the cutting balloon dilator 1826, the cutting members 1828 may be disposed along only a portion of the circumference of the balloon 1826. This may be advantageous, because in some cases it may be desirable to score only a portion of a circumference of a Eustachian tube. In some cases, for example, it may be desirable to only score a posterior aspect of the Eustachian tube, perhaps because that portion will react in a desired way to that treatment. Also in various embodiments, the cutting members 1828 may have various suitable heights, sharpness, or other cutting characteristics to provide different levels/depths of cutting. This may be advantageous, because different depths of cutting may be desirable in different Eustachian tubes.

Figure 19A:
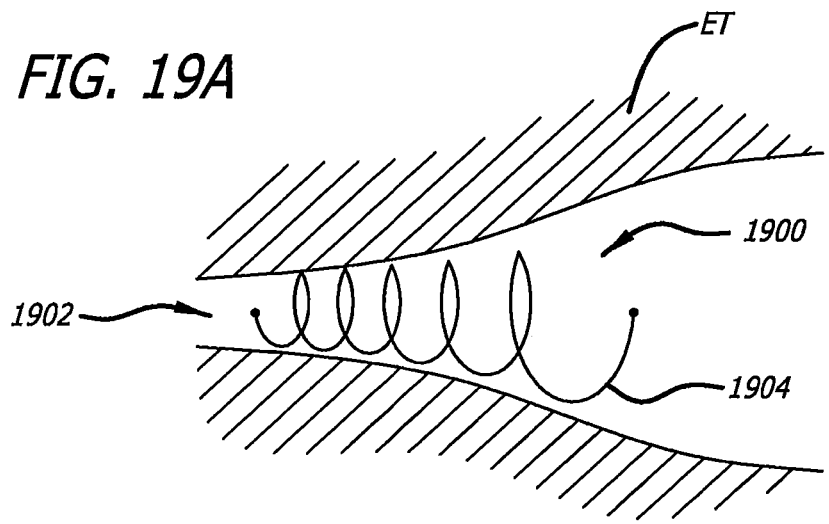
FIGS. 19A and 19B show side views of a stents for providing therapy to a Eustachian tube of a patient.

In various embodiments of a method for treating a Eustachian tube, a stent may be used to prop open a dilated portion of the Eustachian tube, deliver a drug to the Eustachian tube, or both. FIG. 19A shows a stent 1900 according to one embodiment. The stent 1900 is configured as a tapered coil that gradually increases in diameter from a distal portion 1902 to a proximal portion 1904. The shape of the coil may be similar in scale to the pharyngeal ostium of the Eustachian tube ET, to enhance dilation thereof. The stent 1900 may be constructed from a malleable or shape-memory alloy. Alternatively, the stent 1900 may be constructed from a biodegradable polymer. The stent 1900 may be configured to carry and deliver a substance, such as any of the therapeutic or diagnostic agents disclosed herein, for example, via a biodegradable polymeric coating containing the substance. The polymeric coating may comprise a substance matrix blended with a biodegradable polymer based on lactic or glycolic acid, or on other materials, including poly(dioxanone), poly(trimethylene carbonate) copolymers, and poly (-caprolactone) homopolymers, copolymers polyanhydride, polyorthoester, or polyphosphazene. The stent 1900 may be carried and delivered by a dilation catheter, such as any of the dilation catheters disclosed herein. In use, the stent 1900 maintains mechanical expansion of the opening of the Eustachian tube ET, as shown. Alternatively, the stent 1900 may be configured to apply a minimal force against the Eustachian tube ET wall in order to provide mechanical assistance thereto. The stent may be placed in the Eustachian tube ET permanently or removed at a later time. It should be understood that, due to the open, coil shaped configuration of stent 1900, stent 1900 may provide a substantially clear path for ventilation through the Eustachian tube ET while stent 1900 is positioned in the Eustachian tube ET.

Figure 19B:
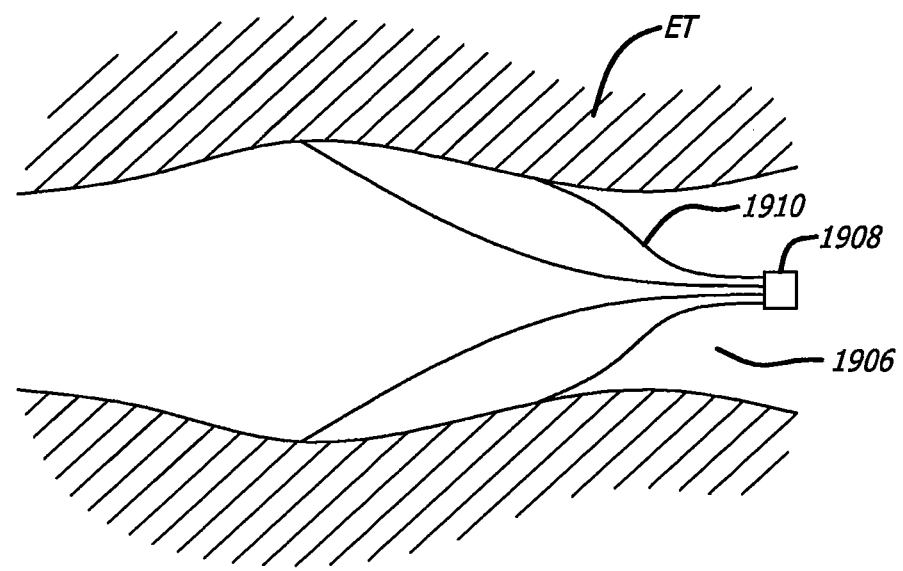

FIG. 19B shows a stent 1906 according to another embodiment. The stent includes a connecting member 1908 that connects a plurality of expandable tines 1910. The tines 1910 may be constructed from a malleable or shape-memory alloy. Alternatively, the tines 1910 may be constructed from a biodegradable polymer. The tines 1910 may be configured to carry and deliver a substance, such as any of the therapeutic or diagnostic agents disclosed herein, for example, via a biodegradable polymeric coating containing the substance. The polymeric coating may comprise a substance matrix blended with a biodegradable polymer based on lactic or glycolic acid, or on other materials, including poly(dioxanone), poly(trimethylene carbonate) copolymers, and poly (-caprolactone) homopolymers, copolymers polyanhydride, polyorthoester, or polyphosphazene. The tines 1910 may be carried and delivered by a dilation catheter, such as any of the dilation catheters disclosed herein. The tines 1910 may be configured to radially self-expand upon removal from a constricting shaft, or through force from a balloon. In use, the stent 1906 maintains mechanical expansion of the Eustachian tube ET, as shown. Alternatively, the stent 1906 may be configured to apply a minimal force against the Eustachian tube ET wall in order to provide mechanical assistance thereto. The stent 1906 may be placed in the Eustachian tube ET permanently or removed at a later time. It should be understood that, due to the open configuration of stent 1910, stent 1910 may provide a substantially clear path for ventilation through the Eustachian tube ET while stent 1910 is positioned in the Eustachian tube ET.

Figure 19C:
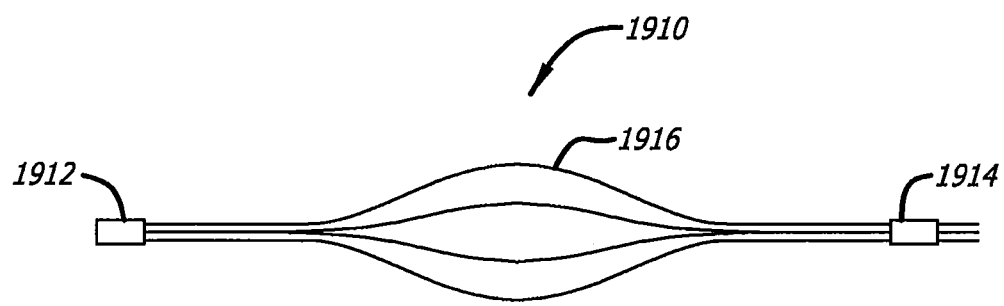
FIGS. 19C and 19D show side views of a stent in different stages of expansion for providing therapy to a Eustachian tube of a patient.
Figure 19D:
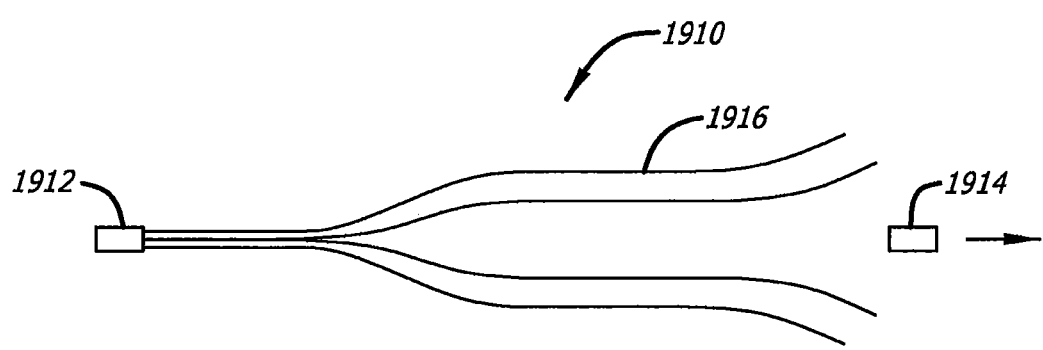

FIGS. 19C and 19D show a stent 1910 according to another embodiment. The stent includes a distal connecting member 1912 and a removable proximal connecting member 1914, which connect a plurality of expandable tines 1916. The tines 1916 may be constructed from a shape-memory alloy. Alternatively, the tines 1916 may be constructed from a biodegradable polymer. The tines 1916 may be configured to carry and deliver a substance, such as any of the therapeutic or diagnostic agents disclosed herein, for example, via a biodegradable polymeric coating containing the substance. The polymeric coating may comprise a substance matrix blended with a biodegradable polymer based on lactic or glycolic acid, or on other materials, including poly(dioxanone), poly(trimethylene carbonate) copolymers, and poly (-caprolactone) homopolymers, copolymers polyanhydride, polyorthoester, or polyphosphazene. The tines 1916 may be carried and delivered by a dilation catheter, such as any of the dilation catheters disclosed herein. The tines 1916 may be configured to radially self-expand upon removal from a constricting shaft. In use, the stent 1906 is delivered via a delivery catheter. The removable proximal connecting member 1914 can then be removed to expand the proximal portion of the stent 1910, and accordingly expand the pharyngeal ostium of the Eustachian tube ET. Once in place, the stent 1906 maintains mechanical expansion of the Eustachian tube ET. Alternatively, the tines 1916 may be configured to apply a minimal force against the Eustachian tube ET wall in order to provide mechanical assistance thereto. The stent 1910 may be placed in the Eustachian tube ET permanently or removed at a later time. It should be understood that, due to the open configuration of stent 1910, stent 1910 may provide a substantially clear path for ventilation through the Eustachian tube ET while stent 1910 is positioned in the Eustachian tube ET.

FIGS. 20A, 20B and 20C show distal configurations of the guide catheter 1600 according to various embodiments. The distal tips shown can be configured to enter the Eustachian tube ET in order to enable other devices to advance therein. FIG. 20A shows a beveled tip 2002, which allows easier entry into the Eustachian tube ET via a reduced leading edge. FIG. 20B shows a tapered tip 2004, which allows easier entry into the Eustachian tube ET via a reduced leading edge. FIG. 20C shows a bulbous tip 2006, which enables the guide catheter 1600 to seal the Eustachian tube ET via an increased sealing area. The tips may be constructed from a flexible material, such as silicone or rubber, which provides good sealing ability with the Eustachian tube ET. In use, the tips can seal the Eustachian tube ET for therapies such as pressurization, suction and/or the application of a substance to the Eustachian tube ET.

Figure 21A:
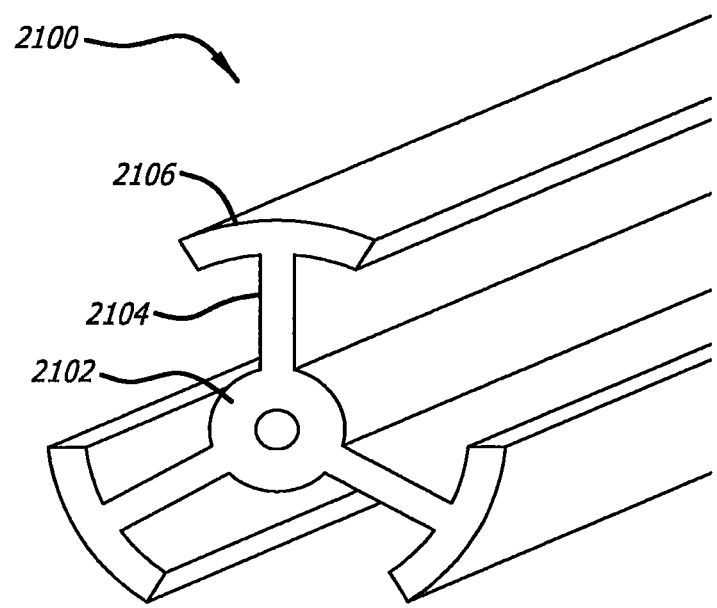
FIG. 21A shows a perspective view of an elongate insert for providing therapy to a Eustachian tube of a patient.
Figure 21B:
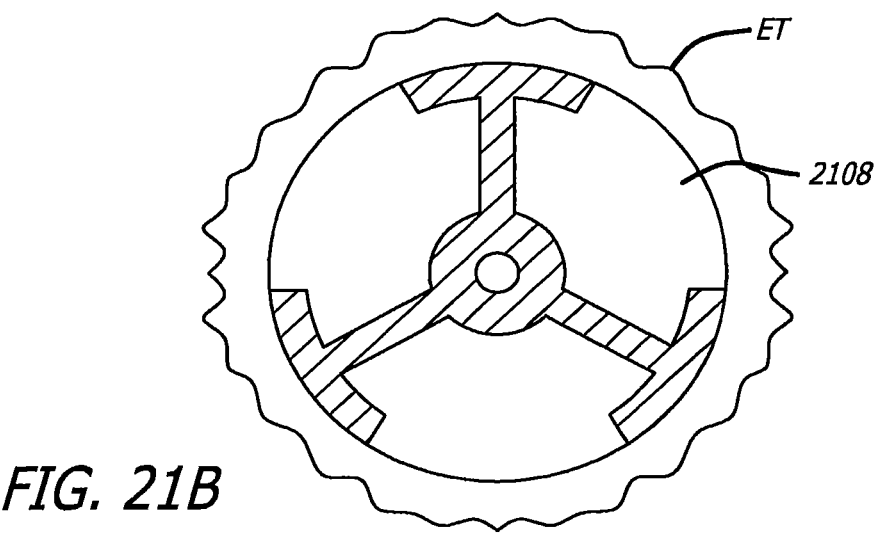
FIG. 21B shows a cross-sectional view of the elongate insert of FIG. 21A disposed in the Eustachian tube of a patient.

FIGS. 21A and 21B show an insert 2100 according to one embodiment. The insert includes a central elongate shaft 2102 with a plurality of braces 2104 circumferentially extending therefrom. Each brace 2104 is connected to an outer member 2106, which is rounded for placement against the Eustachian tube ET. The insert 2100 as shown includes three triangulated braces 2104, however, two or more braces 2104 may be used in alternative embodiments. The insert 2100 may be constructed from a flexible polymer extruded from a die. Alternatively, the insert 2100 may be constructed from a biodegradable polymer. The outer members 2106 may be configured to carry and deliver a substance, such as any of the therapeutic or diagnostic agents disclosed herein. The insert 2100 may be carried and delivered by a dilation catheter, such as any of the dilation catheters disclosed herein. The insert 2100 may be configured to self-expand upon removal from a constricting shaft. In use, the stent 1906 is delivered via a delivery catheter. Once in place, the insert 2100 maintains mechanical expansion of the Eustachian tube ET, as shown in FIG. 21B. The insert 2100 provides and maintains open spaces 2108 in the Eustachian tube ET to maintain pressure equalization therein. The insert 2100 may be placed in the Eustachian tube ET permanently or removed at a later time. It should be understood that, due to the open configuration provided by open spaces 2108 of insert 2100, insert 2100 may provide a substantially clear path for ventilation through the Eustachian tube ET while stent 1910 is positioned in the Eustachian tube ET.

Figure 22A:
FIG. 22A shows a side view of a string insert for providing therapy to a Eustachian tube of a patient.

FIG. 22A shows a string insert 2200 according to one embodiment. The string insert 2200 may be an elongate alloy or polymer string configured to carry and deliver a substance to the Eustachian tube ET, such as any of the therapeutic or diagnostic agents described herein. The string insert 2200 may be a biodegradable polymer based on lactic or glycolic acid, or on other materials, including poly (dioxanone), poly(trimethylene carbonate) copolymers, and poly (-caprolactone) homopolymers, copolymers polyanhydride, polyorthoester, or polyphosphazene. The string insert may be flexible to conform to the passage of the Eustachian tube ET. The string insert 2200 can be made from several strings in a braided configuration. The string insert can include a proximal loop 2201 to aid in removal from the Eustachian tube ET.

Figure 22B:
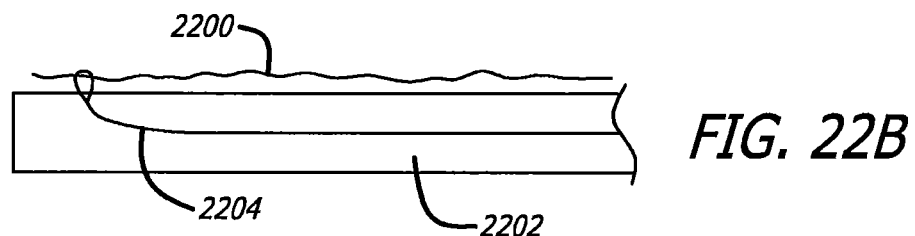
FIGS. 22B, 22C and 22D show partial cross-sectional views of delivery catheters for delivering the string insert of FIG. 22A.
Figure 22C:
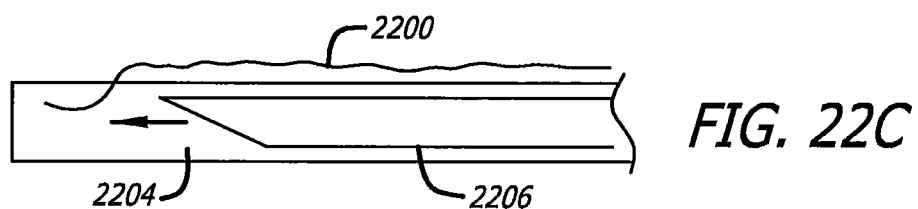
Figure 22D:
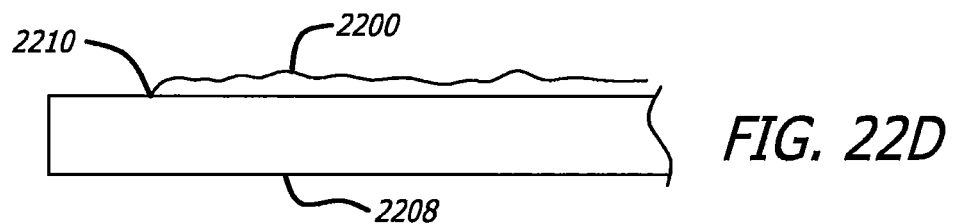

FIGS. 22B, 22C and 22D show delivery catheters for delivering the string insert 2200 to a Eustachian tube ET, according to various embodiments. Delivery catheter 2202 is configured as a shaft and includes a snare 2204 for externally holding the string insert 2200. The delivery catheter 2202 can be configured to be slid over the guidewire 1604. In use, the snare 2204 may be actuated to release tension on the string insert 2200 and allow the removal thereof from the delivery catheter 2202.

Delivery catheter 2204 is configured as a shaft which externally holds the string insert 2200, with a distal portion of the string insert 2200 being internally located. A slidable cutting member 2206 is moveably housed within the delivery catheter 2204. The delivery catheter 2204 can be configured to slide over the guidewire 1604. In use, the slidable cutting member 2206 moves in a distal direction to cut string insert 2200 for detachment from the delivery catheter 2204.

Delivery catheter 2208 is configured as a shaft which externally holds the string insert 2200 on an external surface of the delivery catheter 2208. The delivery catheter 2208 can be configured to slide over the guidewire 1604. A connection 2210 between the delivery catheter 2208 and the string insert 2200 can be electrically fused. In use, the connection 2210 breaks when a suitable electrical current is passed therethrough.

Figure 22E:
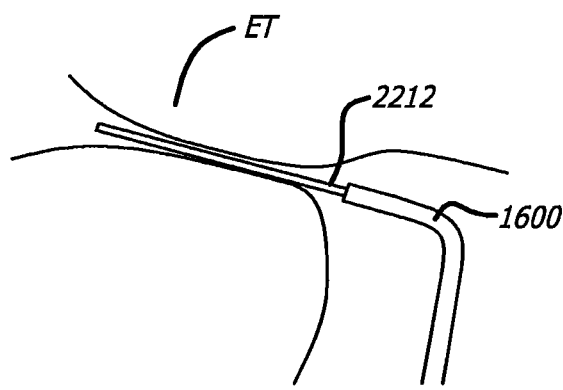
FIGS. 22E and 22F show partial cross-sectional views of the string insert of FIG. 22A being used in a method for providing therapy to a Eustachian tube of a patient.
Figure 22F:
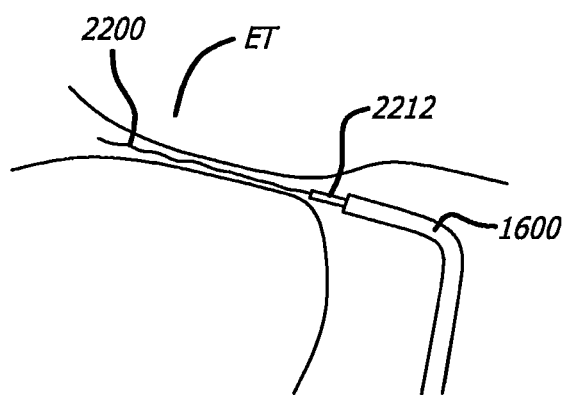

FIGS. 22E and 22F show the string insert 2200 in use, according to one embodiment. The string insert 2200 is delivered via a delivery catheter 2212 and the guide catheter 1600. The guidewire 1604 may also be used to assist delivery. The delivery catheter 2212 may be any of the delivery catheters described above. Once the string insert 2200 is placed within the Eustachian tube ET, it can deliver a substance over a sustained period of time. The string insert 2200 may be left in the Eustachian tube ET permanently or removed at a later time.

As mentioned previously, any implantable embodiment described herein, such as but not limited to those described in FIGS. 21 and 22, may optionally include one or more anchoring members for anchoring the implant in the Eustachian tube or the nasal cavity. Such anchoring members help prevent unwanted migration of an implant out of the Eustachian tube and may include, for example, a suture loop, barb or clip.

In various alternative embodiments, any of a number of different endoscopes may be included as part of the methods and systems described above. For example, a standard ENT endoscope may be used in some embodiments—either a zero degree endoscope, an angled endoscope or a combination of both. In another embodiment, a variable degree of view endoscope, such as a swing prism endoscope, may be used. In still another embodiment, a flexible endoscope such as a fiber optic or CMOS scope may be used.

Figure 23A:
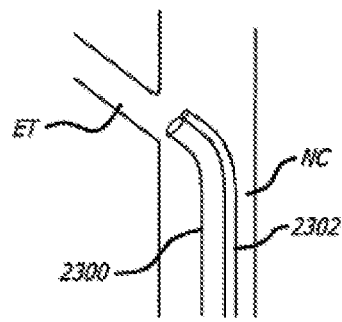
FIGS. 23A-23C are various views of two embodiments of a Eustachian tube access guide device coupled with an endoscope.
Figure 23B:
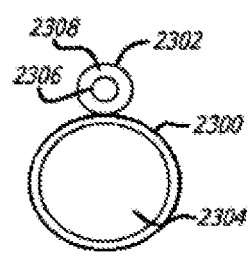
Figure 23C:
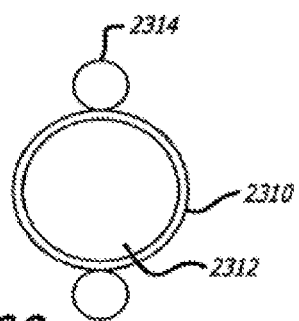

In some embodiments, an endoscope may be attached to or incorporated into a dilation catheter (or other treatment catheter) or a guide catheter. FIGS. 23A-23C show two embodiments of endoscopes attached to guide catheters. FIG. 23A shows a guide catheter 2300 disposed in a nasal cavity NC with its distal end near a Eustachian tube ET. The guide catheter 2300 includes a side-mounted endoscope channel 2302 through which an endoscope such as a flexible fiberscope may be advanced or permanently placed. FIG. 23B is a cross-sectional, end-on view of the guide catheter 2300, which includes an instrument channel 2304 and the endoscope channel 2302. The endoscope channel 2302 may include optical fibers (or alternatively a chip) in a central portion 2306 and illumination fibers in an outer portion 2308, or vice versa. FIG. 23C is a cross-sectional view of alternative embodiment of a guide catheter 2310, which also has an instrument channel 2312 but additionally has two side channels comprising a first channel 2314 for optical fibers or a chip and a second channel 2316 for illumination fibers (or vice versa). In various embodiments, any suitable combination and placement of channels may be used. In an alternative embodiment, illumination fibers and/or a fiber optic scope may be embedded into a wall of a guide catheter.

FIGS. 24A-24C demonstrate two alternative embodiments, in which an endoscope is incorporated into a balloon catheter. As shown in FIG. 24A, a balloon catheter 2400 may generally include a shaft 2402 and a balloon 2404. FIG. 24B shows the balloon catheter 2400 in cross-section from the perspective of the line A-A in FIG. 24A. In this embodiment, the outer ring is the balloon 2404, the middle ring 2406 is a channel through which illumination fibers pass, and the inner circle 2408 is a channel through which visualization fibers or a chip pass. In an alternative embodiment, shown in FIG. 24C, a balloon catheter 2410 may include an outer balloon 2414 surrounding a channel 2416 for passage of illumination fibers. Within the channel 2416 also reside a malleable support member 2418 (such as a wire or the like) and an inner channel 2412 through which the visualization fibers or chip pass. In various embodiments, any combination and configuration of channels may be used.

In yet another alternative embodiment (not pictured), any of the devices described herein may be coupled with an endoscope using a sheath, some of which are known in the art and some of which may be invented in the future. The sheath may be disposable and may cover a portion of any suitable endoscope, such as but not limited to a standard endoscope used by ENT physicians, a variable degree of view endoscope, an angled scope, or the like. The sheath may fit over the endoscope (or a portion of the endoscope) and include a side channel through which one or more working devices, such as a guide catheter, balloon dilation catheter, other treatment or diagnostic catheter, or the like may pass.

Figure 25:
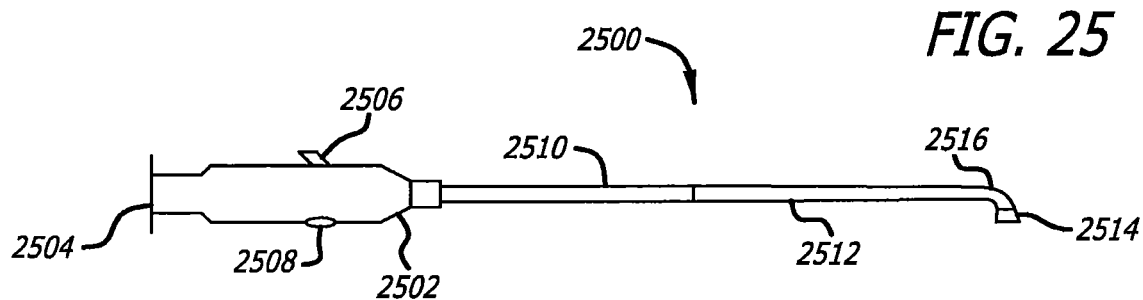
FIG. 25 is a side view of a Eustachian tube access guide according to one embodiment.

Referring now to FIG. 25, in one embodiment a Eustachian tube access guide 2500 may include a hub 2502, a proximal shaft portion 2510, and a distal shaft portion 2512. The hub 2502 may include a stop 2504 on the proximal end, a suction port 2506 for connecting a source of suction such as a suction tube (not shown), and a finger hole 2508 for applying a finger to apply suction through the device 2500. The distal shaft portion 2512 may include a bend 2516 and a distal tip 2514. In one embodiment, the Eustachian tube access guide 2500 may be configured and/or manufactured similarly to the Relieva Flex™ Sinus Guide Catheter (Acclarent, Inc., Menlo Park, Calif.).

The access guide 2500 may have any suitable length, diameter and angle of bend. For example, in various embodiments, the access guide 2500 may have an angle of between about 0 degrees and about 180 degrees, and more preferably between about 30 degrees and about 90 degrees. The proximal shaft portion 2510 may be made of a hypotube, the distal shaft portion 2512 may be made of Nylon, and the distal tip 2514 may be made of Pebax in one embodiment. In various embodiments, the distal portion 2512 may be between about 4 cm and about 8 cm and more preferably about 6 cm, and the proximal portion 2510 may be between about 5 cm and about 15 cm, and more preferably between about 8 cm and about 12 cm.

Figure 26:
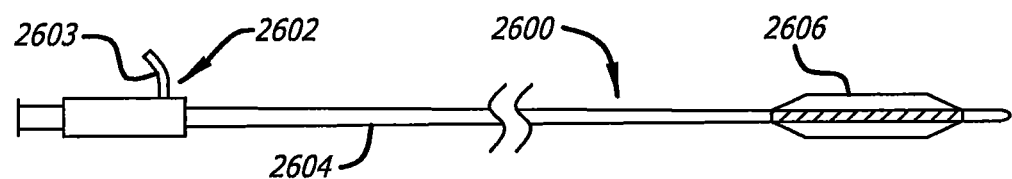
FIG. 26 is a side view of a Eustachian tube balloon dilation catheter according to one embodiment.

Referring now to FIG. 26, a balloon dilation catheter 2600 for dilating a Eustachian tube may in some embodiments include a proximal hub 2602, including a finger hold 2603, a shaft 2604 and a balloon 2606. The balloon dilation catheter 2600 may have many of the same features, dimensions and other properties of the Relieva Solo Pro™ Sinus Balloon Catheter or the Relieva Solo™ Sinus Balloon Catheter (Acclarent, Inc., Menlo Park, Calif.). In some embodiments, one or more feature, dimension or the like of such catheters may be altered to facilitate use of the balloon catheter 2600 in a Eustachian tube.

Figure 27:
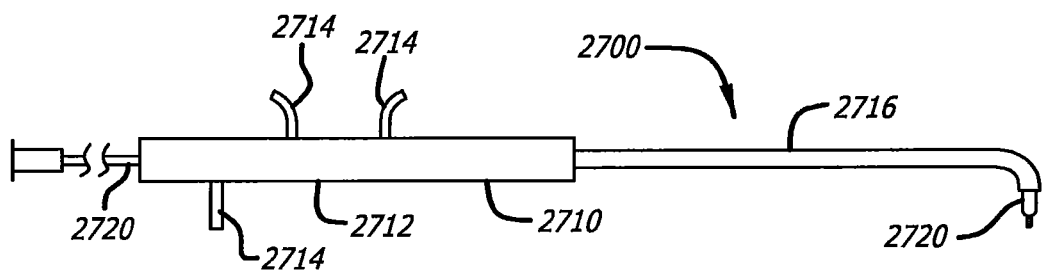
FIG. 27 is a side view of a Eustachian tube access guide and balloon dilation catheter disposed within the guide according to one embodiment.

With reference now to FIG. 27, in one embodiment a system for dilating a Eustachian tube 2700 may include a guide device 2710 and a balloon dilation catheter 2720. The guide device 2710 may have any of the features or characteristics discussed in relation to embodiments described above. In addition, the guide device 2710 may include a handle 2712 having finger holds 2714. The handle 2710 may be coupled with a shaft 2716, and the balloon catheter 2720 may pass through the handle 2712 and the shaft 2716.

Figure 28A:
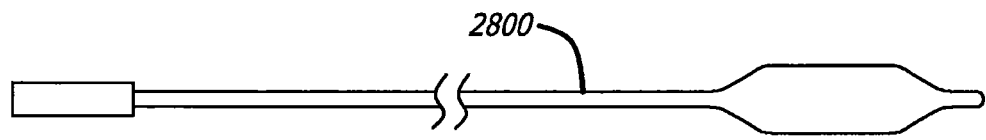
FIGS. 28A-28D are side views of a balloon catheter and a pre-shaped, curved stylet that curves the balloon catheter according to one embodiment.
Figure 28B:
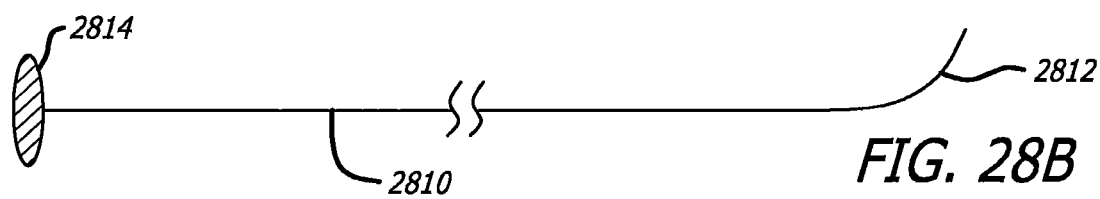
Figure 28C:
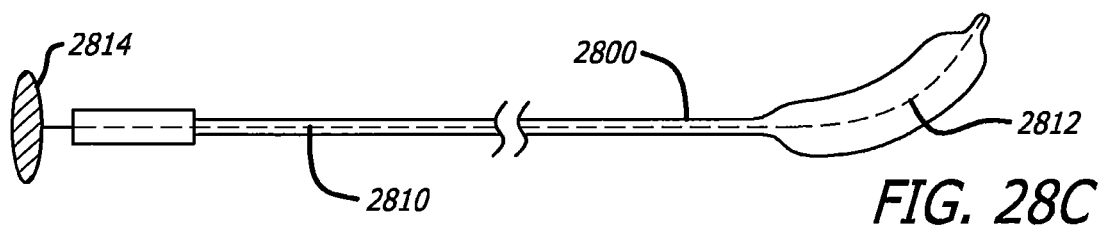
Figure 28D:
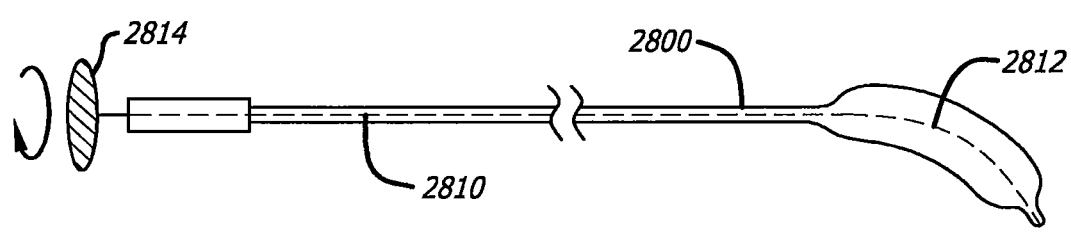

Referring now to FIGS. 28A-28D, in one embodiment a balloon dilation catheter 2800 (FIG. 28A) for dilating a Eustachian tube may be used with a stylet 2810 (FIG. 28B) having a curved portion 2812 and a handle 2814. As shown in FIG. 28C, when the stylet 2810 is advanced into the balloon catheter 2800, the stylet 2810 has sufficient rigidity to retain approximately its original shape, thus conferring the curve of the curved portion 2812 onto the balloon catheter 2800. As shown in FIG. 28D, by turning the handle 2814, the balloon catheter 2800 may be steered, as the curved portion 2812 of the stylet 2810 turns the distal portion of the balloon catheter 2800 in another direction. This is but one example of ways in which a balloon catheter 2800 may be steered in various embodiments.

Figure 29A:
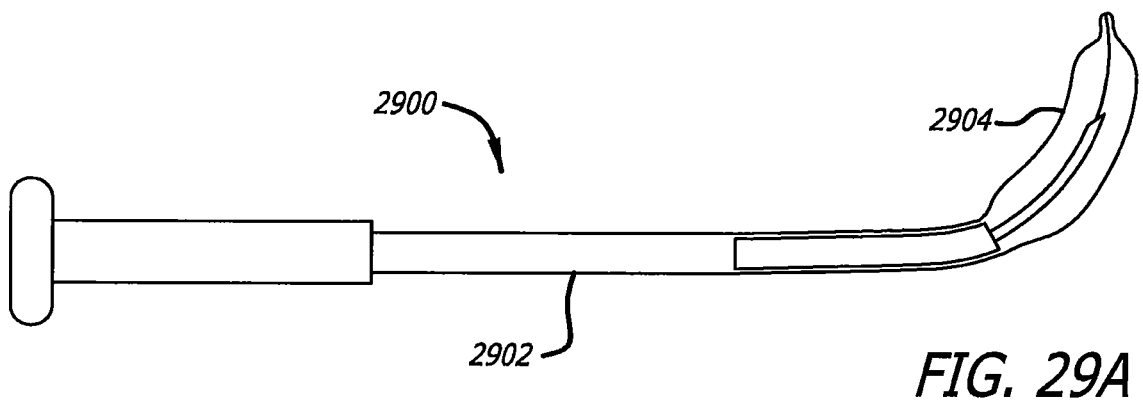
FIGS. 29A and 29B are side views of an extendable, telescoping balloon catheter with guide according to one embodiment.
Figure 29B:
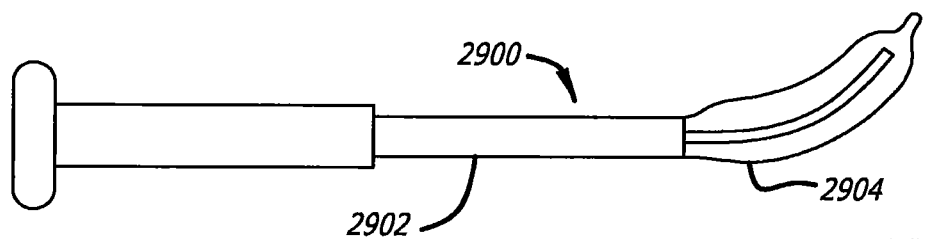

In another embodiment, and with reference now to FIGS. 29A and 29B, a balloon dilation device 2900 may include a telescoping shaft 2902 and an inflatable balloon portion 2904. As shown in FIG. 29A, in one configuration the telescoping shaft 2902 may be lengthened to advance the balloon portion 2904 into a Eustachian tube. As shown in FIG. 29B, in another configuration the telescoping shaft 2902 may be shortened to retract the balloon portion 2904 and/or for initially advancing the device 2900 into the nasal cavity. This embodiment is but one example of ways in which a dilation device may be advanced into a nasal cavity and subsequently a Eustachian tube to dilate the Eustachian tube.

Various examples herein include dilation instruments that rely on inflation of a balloon in order to provide dilation of the Eustachian tube ET (or some other anatomical passageway). However, it should be understood that various other kinds of instruments may be used to provide dilation of the Eustachian tube ET (or some other anatomical passageway). Such alternative instruments may rely on mechanical expansion of a mechanism in order to provide dilation, in addition to or in lieu of relying on inflation of a balloon or other inflatable member in order to provide dilation. By way of example only, mechanical dilation may be provided in accordance with at least some of the teachings of U.S. patent application Ser. No. 14/658,432, entitled "Mechanical Dilation of the Ostia of Paranasal Sinuses and Other Passageways of the Ear, Nose and Throat," filed Mar. 16, 2015, published as U.S. Pub. No. 2015/0250992 on Sep. 10, 2015, the disclosure of which is incorporated by reference herein. Other suitable ways in which mechanical dilation may be provided will be apparent to those of ordinary skill in the art in view of the teachings herein.

FIG. 30-31 show an exemplary guidewire 50 that can be used in conjunction with the procedures described above. Guidewire 50 comprises a coil 52 positioned about a core wire 54. An illumination fiber 56 extends along the interior of core wire 54 and terminates in an atraumatic lens 58. A connector 55 at the proximal end of guidewire 50 enables optical coupling between illumination fiber 56 and a light source. Illumination fiber 56 may comprise one or more optical fibers. Lens 58 is configured to project light when illumination fiber 56 is illuminated by the light source, such that illumination fiber 56 transmits light from the light source to the lens 58. In some versions, the distal end of guidewire 50 is more flexible than the proximal end of guidewire 50. By way of example only, guidewire 50 may be configured in accordance with at least some of the teachings of U.S. Pub. No. 2012/0078118, issued as U.S. Pat. No. 9,155,492 on Oct. 13, 2015, the disclosure of which is incorporated by reference herein. In some versions, guidewire 50 is configured similar to the Relieva Luma Sentry™ Sinus Illumination System by Acclarent, Inc. of Menlo Park, Calif. Other suitable forms that guidewire 50 may take will be apparent to those of ordinary skill in the art in view of the teachings herein.

Figure 32:
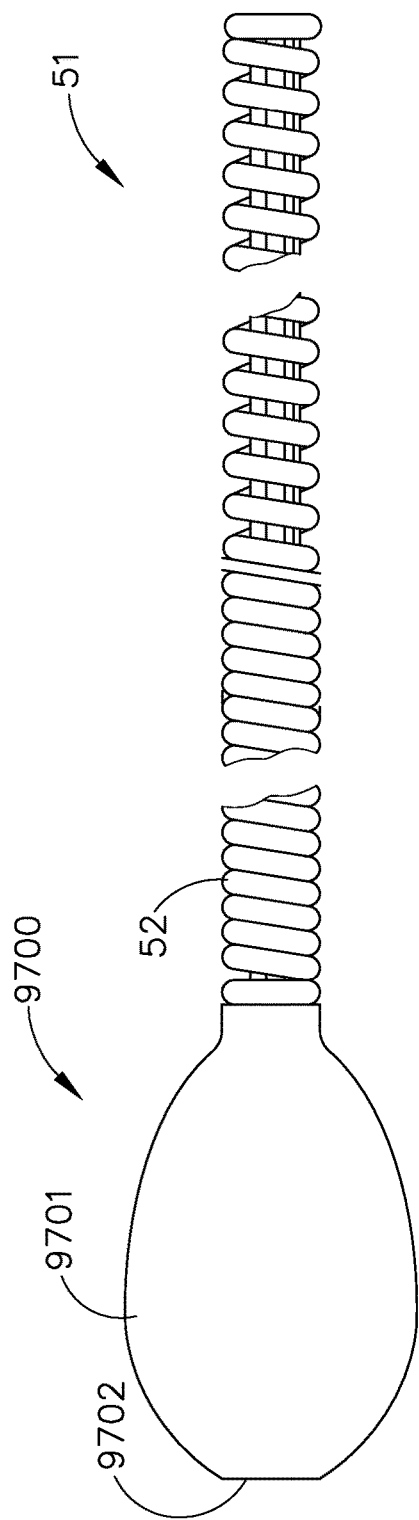
FIG. 32 shows a side elevation view of an exemplary illuminating guidewire suitable for use with a balloon dilation catheter with a widened distal tip.
Figure 33:
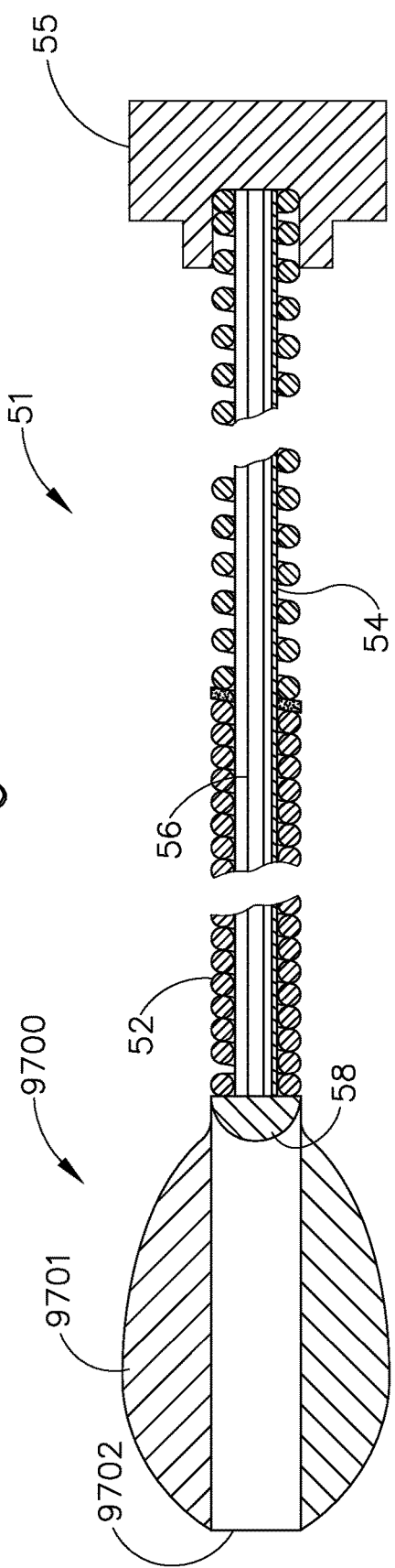
FIG. 33 shows a side cross-sectional view of the illuminating guidewire of FIG. 32.

In some circumstances, particularly when accessing the Eustachian tube ET, it might be beneficial to prevent guidewire 50 from passing through to the Isthmus of the Eustachian tube ET, thereby preventing guidewire 50 from entering middle ear 14 and potentially causing damage. This may be addressed by the exemplary alternative guidewire 51 shown in FIGS. 32-33. Guidewire 51 is similar to guidewire 50 in every way except for the addition of distal tip 9700. Distal tip 9700 is sized in such a way to stop guidewire 51 at the Isthmus before it advances further to middle ear 14. In the present example, the outer diameter of distal tip 9700 is about 2 mm. Alternatively, any other suitable outer diameter may be used. Distal tip 9700 comprises a channel 9702 in order to allow light projected by lens 58 to illuminate the Eustachian tube ET. The light illuminated through channel 9702 into Eustachian tube ET may act as an indicator that the Eustachian tube ET has been sufficiently dilated by transillumination of the tympanic membrane. Additionally or alternatively, distal tip 9700 can be made of material 9701 that is optically transmissive (e.g., transparent or translucent plastic or glass, etc.) such that material 9701 may itself illuminate when light is communicated through illumination fiber 56 and lens 58.

Figure 1:
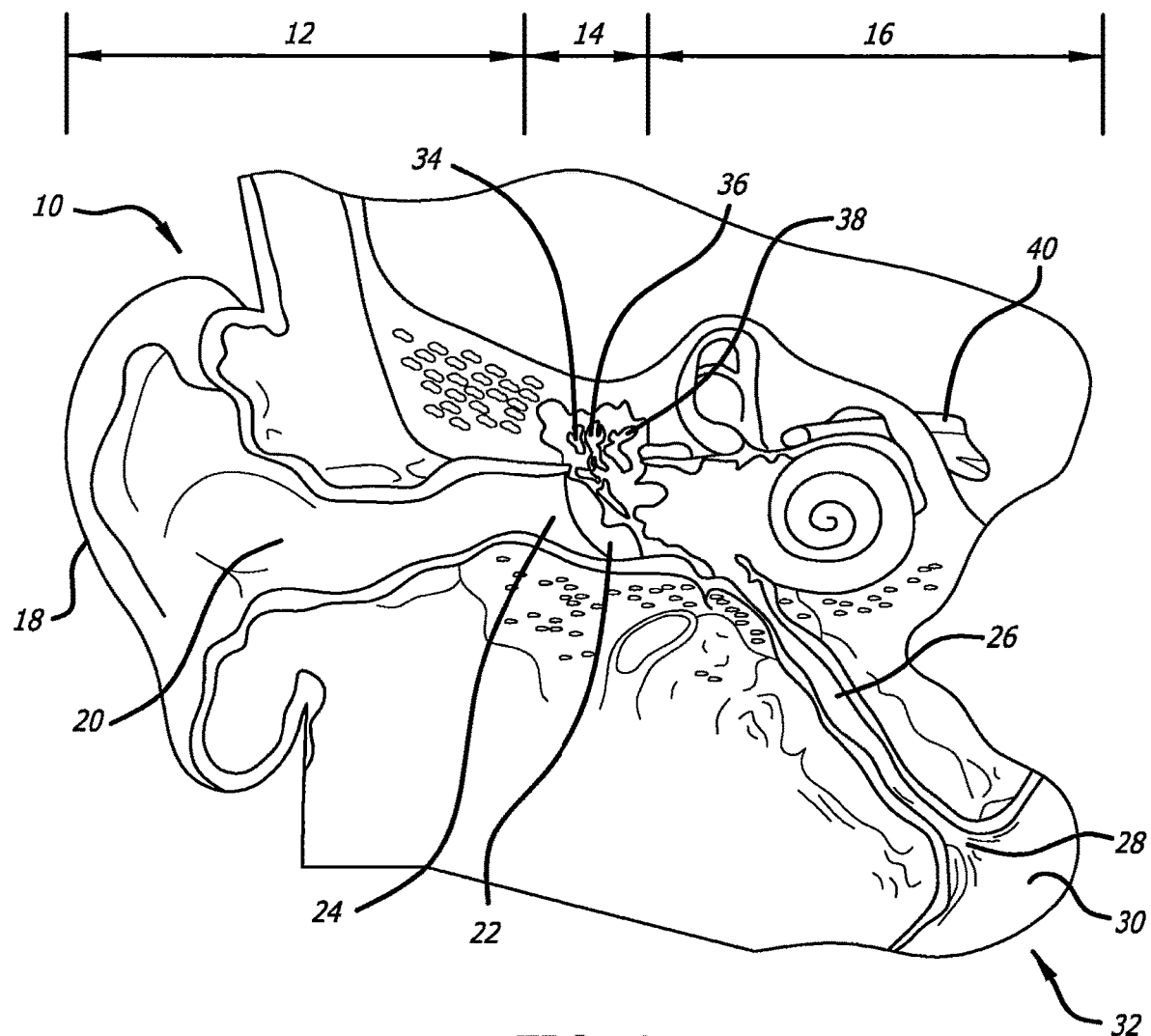
FIG. 1 is a cross-section of a human ear showing the inner, middle and outer ear portions and the Eustachian tube connecting the middle ear with the nasopharynx region of the throat via a distal opening thereof.
Figure 2:
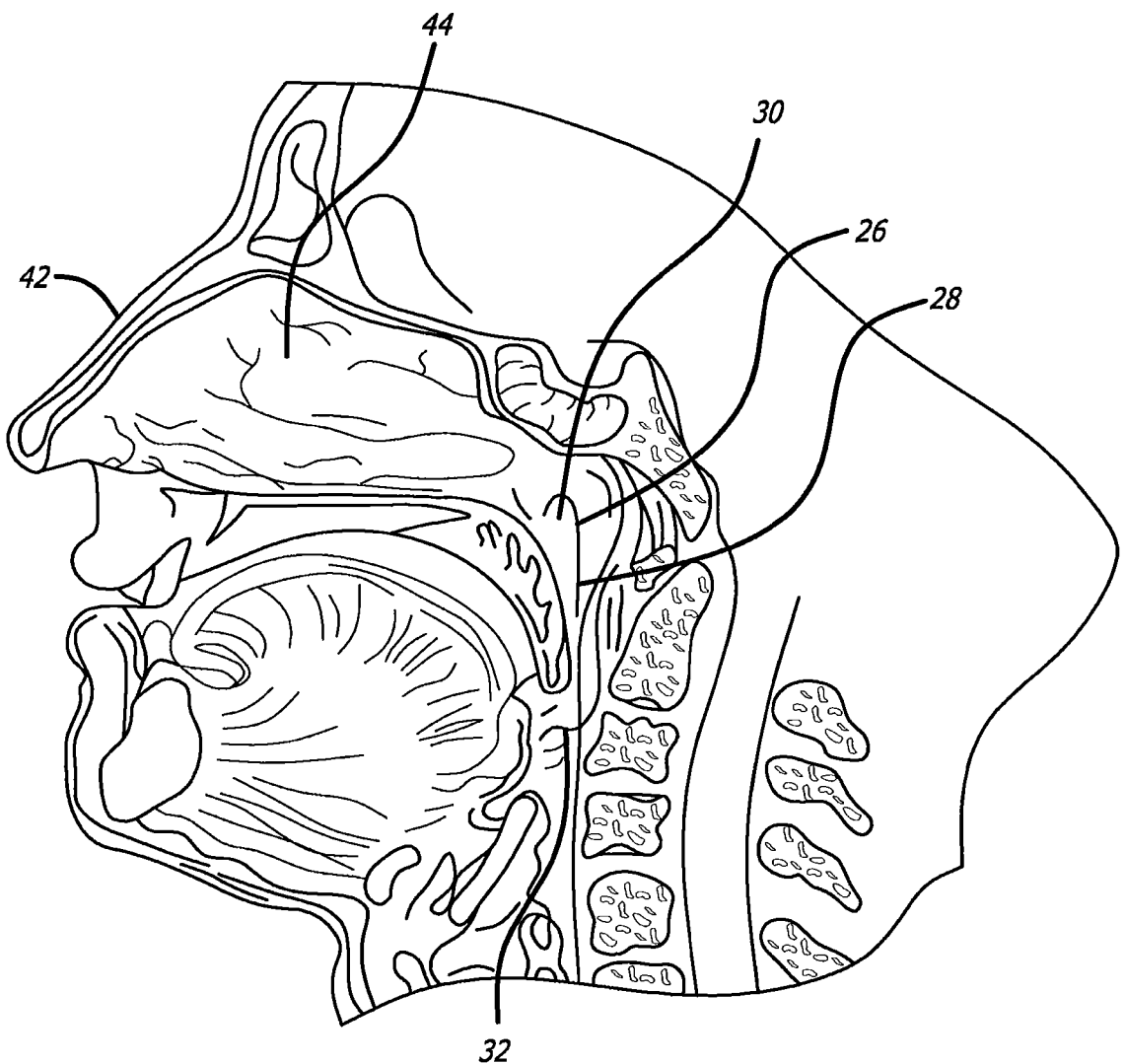
FIG. 2 is a cross-section of a human head showing the nasopharynx region of the throat illustrated in FIG. 1 containing the distal opening of the Eustachian tube illustrated in FIG. 1.
Figure 3:
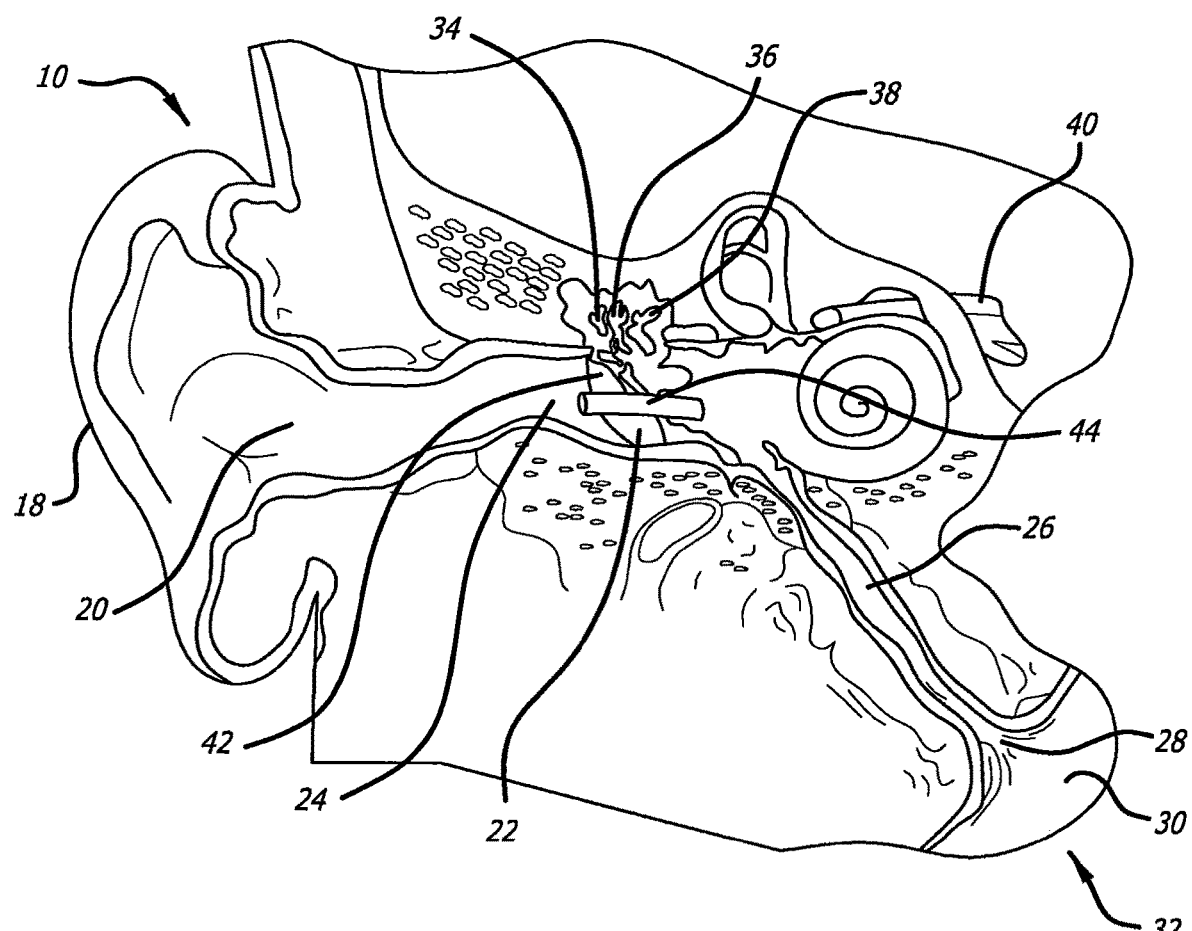
FIG. 3 is a cross-section of a human ear in the orientation shown in FIG. 1 showing a prior art surgical method for relieving fluid in the middle ear in which a ventilation tube is placed within an incision in the eardrum.
Figure 4:
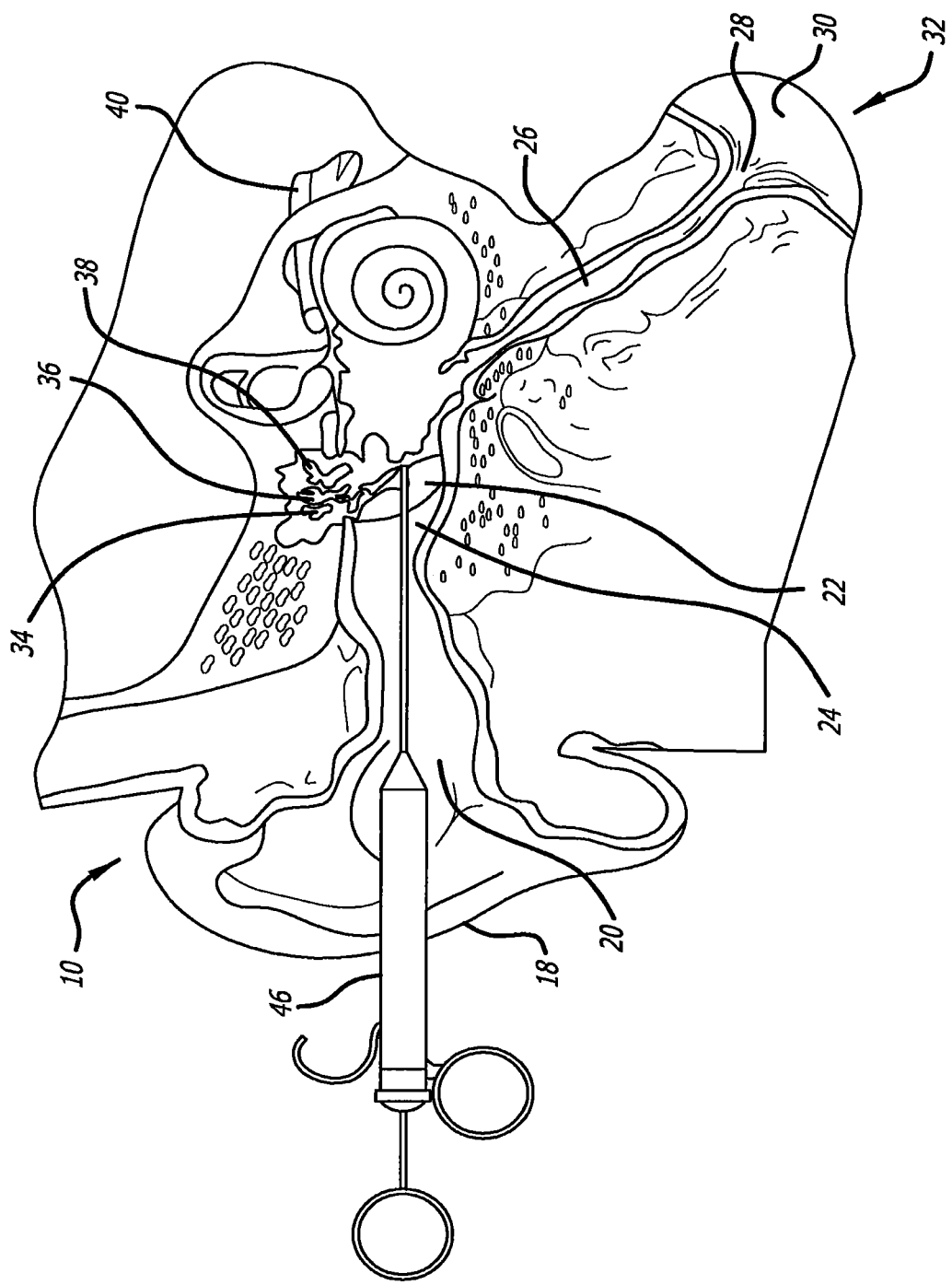
FIG. 4 is a cross-section of a human ear in the orientation shown in FIG. 1 showing a prior art surgical method for relieving fluid in the middle ear in which a syringe is shown having a needle perforating the eardrum.
Figure 5:
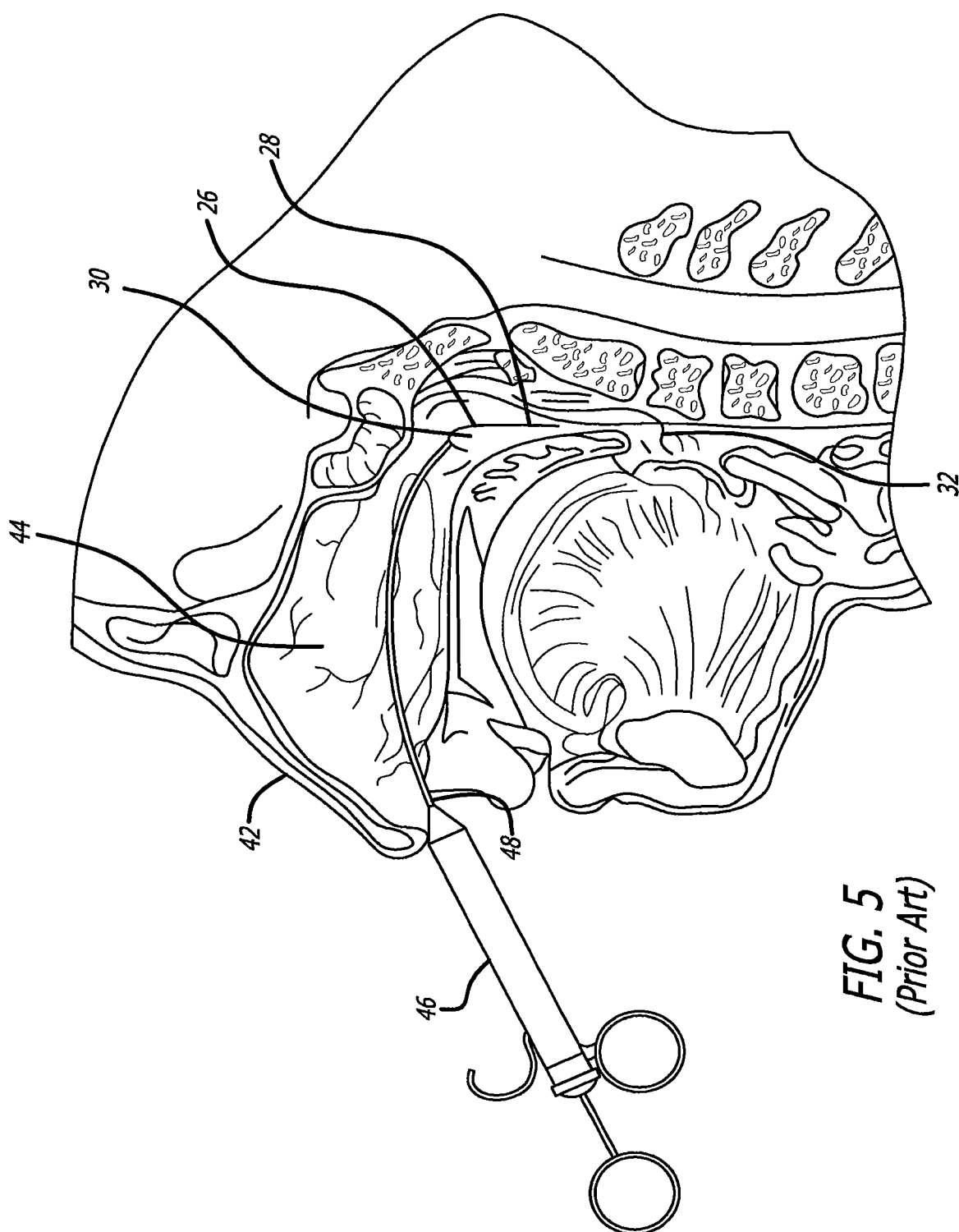
FIGS. 5-6 show a cross-section of a human head in the orientation shown in FIG. 2 showing a prior art politzerization method for relieving fluid in the middle ear in which a syringe is shown having a flexible tip extending into the nose and/or throat area so that the tip abuts the pharyngeal ostium of the Eustachian tube while the nose is plugged.
Figure 6:
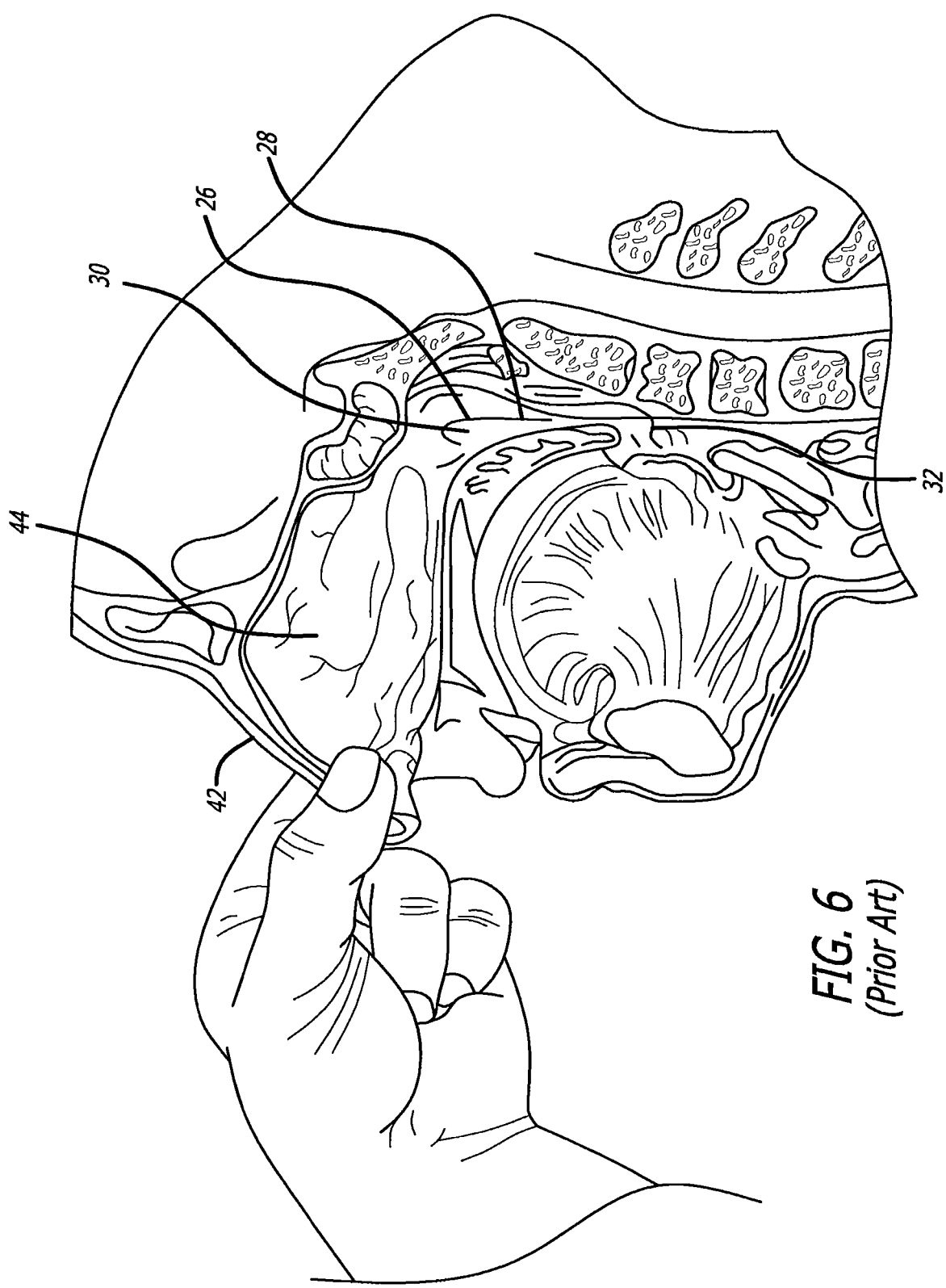

In any of the methods described herein, the operator may first pierce or perforate the eardrum 22 in order to provide a temporary ventilation path through the ear canal 20 via the middle ear 14. For instance, the operator may drive a needle (e.g., as shown in FIG. 4) or other piercing instrument through the eardrum 22 before inserting a dilator into the Eustachian tube ET 26. Alternatively, the operator may first insert the dilator into the Eustachian tube ET 26, then pierce the eardrum 22 before expanding the dilator. In any case, the opening formed through the eardrum 22 may be large enough to allow air to escape from the middle ear 14 via the ear canal 20 during insertion of the dilator in the Eustachian tube ET 26 and/or during expansion of the dilator in the Eustachian tube ET 26. However, the opening formed through the eardrum 22 may be small enough such that the opening may heal on its own without, requiring any kind of adhesives or sutures, etc., after the dilation process is complete. Various suitable ways in which the eardrum 22 may be pierced before insertion of the dilator in the Eustachian tube ET 26 or before expansion of the dilator in the Eustachian tube ET 26 will be apparent to those of ordinary skill in the art in view of the teachings herein.

The present invention may be embodied in other specific forms without departing from the essential characteristics thereof. These other embodiments are intended to be included within the scope of the present invention, which is set forth in the following claims.

We claim:

1. A dilator assembly, comprising:
 (a) a shaft defining a longitudinal axis, wherein the shaft comprises a first distal end and a first proximal end, wherein the shaft defines a first lumen;
 (b) a dilator located on the shaft between the first distal end and the first proximal end, wherein the dilator extends between a second proximal end and a second distal end, wherein the dilator comprises an inflatable body configured to transition between a contracted state and an expanded state; and
 (c) a venting body associated with, yet detached from, an exterior of the inflatable body, wherein the venting body extends at least along the exterior of the inflatable body, while parallel with the longitudinal axis, from the second proximal end and the second distal end, wherein a portion of the venting body is proximal to the dilator, wherein the venting body comprises an open proximal end located at a longitudinal position between the first proximal end of the shaft and the second proximal end of the dilator, wherein the portion of the venting body is laterally spaced away from the shaft and the dilator, wherein the venting body, while extending distally past the second distal end, is configured to define a venting pathway between the second proximal end and the second distal end of the inflatable body while the inflatable body is in the expanded state.

2. The dilator assembly of claim 1, wherein the inflatable body is configured to dilate a Eustachian tube of a patient in the expanded state.

3. The dilator assembly of claim 1, wherein the venting body comprises a tube.

4. The dilator assembly of claim 3, wherein the tube defines a second lumen, wherein at least a section of the second lumen defines the venting pathway.

5. The dilator assembly of claim 4, wherein the tube extends between a third proximal end and a third distal end, wherein the second lumen extends from the third proximal end to the third distal end.

6. The dilator assembly of claim 5, wherein the third distal end of the second lumen is distal in relation to the second distal end of the inflatable body.

7. The dilator assembly of claim 6, wherein the third proximal end of the second lumen is proximal in relation to the second proximal end of the inflatable body.

8. The dilator assembly of 1, wherein an exterior portion of the venting body and an exterior portion of the inflatable body define the venting pathway.

9. The dilator assembly of claim 1, wherein the first lumen extends distally past the inflatable body.

10. The dilator assembly of claim 1, wherein the venting body is non-coaxial relative to the inflatable body.

11. The dilator assembly of claim 1, wherein the inflatable body comprises a first outer diameter and a second outer diameter, wherein the first outer diameter and the second outer diameter are different sizes.

12. The dilator assembly of claim 1, wherein the first lumen terminates at the first distal end of the shaft.

13. A dilator assembly, comprising:
(a) a shaft comprising a first distal end and a first proximal end, wherein the shaft defines a first lumen;
(b) a dilator located on the shaft, wherein the dilator extends between a second proximal end and a second distal end, wherein the second distal end of the dilator is proximal relative to the first distal end of the shaft, wherein the dilator comprises an inflatable body configured to transition between a contracted state and an expanded state; and
(c) a venting body extending along an exterior of the inflatable body such that the venting body extends parallel with the dilator in the expanded state, wherein the venting body extends distally past the exterior of the inflatable body and the first distal end of the shaft, wherein the venting body, while extending distally past the inflatable body, is configured to define a venting pathway between the second proximal end and the second distal end of the inflatable body while the inflatable body is in the expanded state, wherein the venting body comprises an open proximal end located at a longitudinal position between the first proximal end of the shaft and the second proximal end of the dilator.

14. The dilator assembly of claim 13, wherein the venting body comprises a hollow tube.

15. The dilator assembly of claim 13, wherein the venting body extends proximally past the exterior of the inflatable body.

16. The dilator assembly of claim 13, wherein the venting body further defines a second lumen, wherein at least a portion of the second lumen defines the venting pathway.

17. A dilator assembly, comprising:
(a) a shaft defining a longitudinal axis, wherein the shaft comprises a first distal end and a first proximal end;
(b) a dilator located on the shaft extending along a dilator axis, wherein the dilator extends between a second proximal end and a second distal end, wherein the dilator comprises an inflatable body configured to transition between a contracted state and an expanded state; and
(c) a venting body associated with an exterior of the inflatable body while extending parallel with the dilator axis, wherein the venting body extends both proximally and distally past the exterior of the inflatable body into an open proximal end and an open distal end, respectively, wherein the open distal end of the venting body extends distally relative to the dilator along a path that is parallel with, yet laterally spaced away from, the shaft of the dilator assembly, wherein the venting body, while extending distally past the inflatable body, is configured to define a venting pathway between the second proximal end and the second distal end of the inflatable body while the inflatable body is in the expanded state, wherein the venting body comprises an open proximal end located at a longitudinal position between the first proximal end of the shaft and the second proximal end of the dilator.

18. The dilator assembly of claim 17, wherein the venting body further comprises a tube.

* * * * *